US012768836B2

(12) United States Patent
Dagher et al.

(10) Patent No.: US 12,768,836 B2
(45) **Date of Patent: *Oct. 20, 2026**

(54) MULTIPLEXED COLOCALIZATION-BY-LINKAGE ASSAYS FOR THE DETECTION AND ANALYSIS OF ANALYTES

(71) Applicant: Nomic Bio Inc., Montreal (CA)

(72) Inventors: Milad Dagher, Montreal (CA); Jeff Munzar, Montreal (CA); Jinglin Kong, Montreal (CA)

(73) Assignee: Nomic Bio Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/200,680

(22) Filed: Mar. 12, 2021

(65) Prior Publication Data

US 2021/0285937 A1 Sep. 16, 2021

Related U.S. Application Data

(60) Provisional application No. 62/989,571, filed on Mar. 13, 2020, provisional application No. 63/086,536, filed on Oct. 1, 2020.

(51) Int. Cl.
*G01N 33/53* (2006.01)
*C12Q 1/6818* (2018.01)
(Continued)

(52) U.S. Cl.
CPC ....... *G01N 33/5308* (2013.01); *C12Q 1/6818* (2013.01); *G01N 33/54306* (2013.01); *C12Q 1/6851* (2013.01); *G01N 2458/10* (2013.01)

(58) Field of Classification Search
CPC ...... C12Q 1/68; C12Q 1/6804; G01N 33/543; G01N 33/53; G01N 33/5308; G01N 33/54306; G01N 2458/10
See application file for complete search history.

(56) References Cited

U.S. PATENT DOCUMENTS 4,683,195 A 7/1987 Mullis et al.
4,683,202 A 7/1987 Mullis
(Continued)

FOREIGN PATENT DOCUMENTS

CA 2948547 A1 11/2015
CN 1902496 A 1/2007
(Continued)

OTHER PUBLICATIONS

Kumar et al. Point-of-care strategies for detection of wateborne pathogens. Sensors 2019, vol. 19, pp. 1-17. (Year: 2019).*
(Continued)

*Primary Examiner* — Shafiqul Haq
(74) *Attorney, Agent, or Firm* — Wilson Sonsini Goodrich & Rosati

(57) ABSTRACT

Provided herein are colocalization-by-linkage assay (CLA) compositions and methods for multiplexed analysis of an analyte or analytes. The CLA compositions and methods, as described herein, are engineered to detect multiple analytes using multiple detection reagents coupled to a single support. Readout or detection sensitivity is achieved through the use of release-dependent transduction (RDT) or displacer-dependent transduction. Further multiplexing can also be achieved through the use of barcoded elements used in the capture and detection of an analytes.

20 Claims, 15 Drawing Sheets

Specification includes a Sequence Listing.

(51) Int. Cl.
*G01N 33/543* (2006.01)
*C12Q 1/6851* (2018.01)

(56) References Cited

U.S. PATENT DOCUMENTS

| | | | |
|---|---|---|---|
| 4,800,159 A | 1/1989 | Mullis et al. | |
| 4,945,042 A | 7/1990 | Geiger et al. | |
| 4,965,188 A | 10/1990 | Mullis et al. | |
| 5,168,038 A | 12/1992 | Tecott et al. | |
| 5,210,015 A | 5/1993 | Gelfand et al. | |
| 5,399,491 A | 3/1995 | Kacian et al. | |
| 5,539,082 A | 7/1996 | Nielsen et al. | |
| 5,665,539 A | 9/1997 | Sano et al. | |
| 5,695,926 A | 12/1997 | Cros et al. | |
| 5,854,033 A | 12/1998 | Lizardi | |
| 5,925,517 A | 7/1999 | Tyagi et al. | |
| 6,174,670 B1 | 1/2001 | Wittwer et al. | |
| 6,569,627 B2 | 5/2003 | Wittwer et al. | |
| 6,670,461 B1 | 12/2003 | Wengel et al. | |
| 7,306,904 B2 | 12/2007 | Landegren et al. | |
| 8,268,554 B2 | 9/2012 | Schallmeiner | |
| 9,476,089 B2 | 10/2016 | Wu et al. | |
| 9,481,945 B2 | 11/2016 | Juncker et al. | |
| 11,493,505 B2 * | 11/2022 | Juncker | G01N 33/54306 |
| 12,560,595 B2 | 2/2026 | Juncker et al. | |
| 2002/0015962 A1 | 2/2002 | Nolan et al. | |
| 2003/0092901 A1 | 5/2003 | Farooqui et al. | |
| 2005/0026161 A1 | 2/2005 | Jablonski et al. | |
| 2007/0009914 A1 | 1/2007 | Wallace et al. | |
| 2007/0065809 A1 | 3/2007 | Friedman | |
| 2010/0081134 A1 | 4/2010 | Mirkin et al. | |
| 2010/0151472 A1 | 6/2010 | Nolan et al. | |
| 2016/0153973 A1 | 6/2016 | Smith | |
| 2018/0066303 A1 | 3/2018 | Husain et al. | |
| 2019/0237166 A1 | 8/2019 | Juncker et al. | |
| 2020/0191779 A1 | 6/2020 | Glezer et al. | |
| 2020/0319173 A1 * | 10/2020 | Juncker | C12Q 1/6804 |
| 2021/0278398 A1 * | 9/2021 | Luo | C12Q 1/6813 |
| 2023/0090326 A1 | 3/2023 | Juncker et al. | |
| 2023/0111239 A1 | 4/2023 | Juncker et al. | |
| 2023/0116205 A1 | 4/2023 | Dagher et al. | |

FOREIGN PATENT DOCUMENTS

| | | | |
|---|---|---|---|
| CN | 101374965 A | 2/2009 | |
| CN | 102549170 A | 7/2012 | |
| CN | 104245960 A | 12/2014 | |
| CN | 104812915 A | 7/2015 | |
| CN | 112236527 A | 1/2021 | |
| EP | 0168689 A2 | 1/1986 | |
| EP | 0168689 B1 | 9/1990 | |
| EP | 0703296 A1 | 3/1996 | |
| EP | 1767937 A1 | 3/2007 | |
| EP | 3102698 B1 | 1/2019 | |
| JP | H04262799 A | 9/1992 | |
| WO | WO-2004042030 A2 | 5/2004 | |
| WO | WO-2007044903 A2 | 4/2007 | |
| WO | WO-2015006503 A1 | 1/2015 | |
| WO | WO-2018058073 A2 | 3/2018 | |
| WO | WO-2019191838 A1 * | 10/2019 | C12Q 1/6804 |
| WO | WO-2019222708 A2 | 11/2019 | |
| WO | WO-2021064460 A1 | 4/2021 | |
| WO | WO-2021181161 A1 | 9/2021 | |

OTHER PUBLICATIONS

Becker-Andre, et al. Absolute mRNA quantification using the polymerase chain reaction (PCR). A novel approach by a PCR aided transcript titration assay (PATTY). Nucleic Acids Res. Nov. 25, 1989;17(22):9437-46.

Bernard et al., Color multiplexing hybridization probes using the apolipoprotein E locus as a model system for genotyping. Anal Biochem 273(2):221-228 (1999).

Dagher et al., Ensemble multicolour FRET model enables barcoding at extreme FRET levels. Nature Nanotechnology 13: 925-932 (2018).

Diviacco et al., A novel procedure for quantitative polymerase chain reaction by coamplification of competitive templates. Gene 122(2):313-320 (1992).

Freeman, et al. Quantitative RT-PCR: pitfalls and potential. Biotechniques. Jan. 1999;26(1):112-126.

Fu et al., Multiplex Assays for Biomarker Research and Clinical Application: Translational Science Coming of Age. Proteomics Clin Appl. 4(3):271-284 (2010).

Jani et al., Multiplexed immunoassays by flow cytometry for diagnosis and surveillance of infectious diseases in resource-poor settings. The Lancet 2(4): 243-250 (2002).

Krishhan et al., Multiplexed Microbead Immunoassays by Flow Cytometry for Molecular Profiling: Basic Concepts and Proteomics Applications. Crit Rev Biotechnol. 29(1): 29-43 (2009).

Leone, et al. Molecular beacon probes combined with amplification by NASBA enable homogeneous, real-time detection of RNA. Nucleic Acids Res. May 1, 1998;26(9):2150-5.

Li et al., Novel Antibody Microarray Technologies for Multiplex Protein Analysis in Complex Samples. Doctor of Philosophy Department of Biomedical Engineering. McGill University, Montreal, Quebec, Canada 180 pages (2011).

MacKay, et al. Real-time PCR in virology. Nucleic Acids Res. Mar. 15, 2002;30(6):1292-305.

Tighe, et al. ELISA in the multiplex era: Potentials and pitfalls. Proteomics—Clinical Applications. 9 (2015): 406-422.

Tighe et al., Utility, Reliability and Reproducibility of Immunoassay Multiplex Kits. Methods 61(1):23-29 (2013).

U.S. Appl. No. 16/898,338 First Action Interview dated Dec. 8, 2020.

U.S. Appl. No. 16/898,338 First Action Interview dated Sep. 4, 2020.

Zhang et al., Control of DNA strand displacement kinetics using toehold exchange. J Am Chem Soc 131(47):17303-17314 (2009).

Zimmerman et al., "Technical aspects of quantitative competitive PCR," Biotechniques, 21(2):268-279, 1996.

Blank et al., Double-chip protein arrays: force-based multiplex sandwich immunoassays with increased specificity. Analytical and bioanalytical chemistry 379(7): 974-981 (2004).

Boyle, M. Bacterial Immunoglobulin-Binding Proteins: Applications in Immunotechnology. Academic press (2014).

Dagher, M. Scalable affinity-proteomics on microparticles. Chapter IV (2019).

Huiyan, Novel antibody microarray technologies for multiplex protein analysis in complex samples. Doctor of Philosophy Department of Biomedical Engineering, McGill University. Montreal, Quebec, Canada (2014). 180 pages.

Juncker et al., Cross-reactivity in antibody microarrays and multiplexed sandwich assays: shedding light on the dark side of multiplexing. Current opinion in chemical biology 18: 29-37 (2014).

Laforte et al., Antibody colocalization microarray for cross-reactivity-free multiplexed protein analysis. Serum/Plasma Proteomics. Human Press 239-261 (2017).

Li et al., A new class of homogeneous nucleic acid probes based on specific displacement hybridization. Nucleic Acids Research 30(2): e5 (2002).

PCT/CA2019/050405 International Search Report and Written Opinion dated Jun. 17, 2019.

PCT/IB2021/000140 International Search Report and Written Opinion dated Jun. 17, 2021.

U.S. Appl. No. 16/898,338 Final Office Action dated Apr. 13, 2021.

Bunt, G. et al., "FRET from single to multiplexed signaling events", Biophys Rev, 2017, vol. 9, pp. 119-129.

Corry, B. et al., "A Flexible Approach to the Calculation of Resonance Energy Transfer Efficiency between Multiple Donors and Acceptors in Complex Geometries", Biophysical Journal, 2005, vol. 89, pp. 3822-3836.

Dagher et al., One-pot microsphere barcoding using fluorescent oligonucleotides. Biomedical Engineering Department and Genome Quebec, McGill University (2016).

(56) References Cited

OTHER PUBLICATIONS

Extended European Search Report dated Nov. 11, 2021 for European Application No. 19781762.0.
Galperin et al., Three-chromophore FRET microscopy to analyze multiprotein interactions in living cells. Nature Methods 1(3): 209-217 (2004).
Gerver et al., Programmable microfluidic synthesis of spectrally encoded microspheres. Lab on a Chip 12(22): 4716 (2012).
Indian Patent Application No. 202017043052 Office Action dated Apr. 22, 2022.
King et al., Understanding the FRET signatures of interacting membrane proteins. The Journal of Biological Chemistry 292(13): 5291-5310 (2017).
PCT/CA2019/050405 International Preliminary Report on Patentability dated Oct. 6, 2020.
PCT/IB2020/000813 International Preliminary Report on Patentability dated Apr. 5, 2022.
PCT/IB2020/000813 International Search Report and Written Opinion dated Jan. 15, 2021.
Stuchly et al., An automated analysis of highly complex flow cytometry-based proteomic data. Cytometry Part A 81A(2): 120-129 (2012).
U.S. Appl. No. 16/153,071 Office Action dated Jan. 25, 2023.
U.S. Appl. No. 16/153,071 Restriction Requirement dated Mar. 4, 2022.
Wagh et al., Polymeric nanoparticles with sequential and multiple FRET cascade mechanism for multicolor and multiplexed imaging. Small 9(12): 2129-2139 (2013).
Wang et al., Multicolor FRET silica nanoparticles by single wavelength excitation. Nano Letters 6(1): 84-88 (2006).
Wolber et al., An analytic solution to the Forster energy transfer problem in two dimensions. Biophysical Journal 28(2): 197-210 (1979).
Bioconjugation and Crosslinking Technical Handbook: Reagents for Bioconjugation, Crosslinking, Biotinylation, and Modification of Proteins and Peptides. Thermo Fisher Scientific, 64 pages. (2022).
CN202080084264.3 Office Action with Search Report dated Jul. 4, 2025, and an English translation.
Co-pending U.S. Appl. No. 18/606,823, inventors Dagher; Milad et al., filed Mar. 15, 2024.
Hein, Christopher D. et al., Click Chemistry, a Powerful Tool for Pharmaceutical Sciences. Pharmaceutical Research 25(10):2216-2230 (2008).
Kolb, Hartmuth C. et al., Click Chemistry: Diverse Chemical Function from a Few Good Reactions. Angewandte Chemie 40(11):2004-2021 (2001).
Li, Jingjing, and Jun-Jie Zhu., Quantum dots for fluorescent biosensing and bio-imaging applications. Analyst 138(9):2506-2515 (2013).
Li, Yougen et al., Controlled Assembly of Dendrimer-like DNA. Nature Materials 3(1):38-42 (2004).
Li, Yougen et al., Multiplexed Detection of Pathogen DNA with DNA-based Fluorescence Nanobarcodes. Nature Biotechnology 23(7):885-889 (2005).
Reyes-Garces, Nathaly et al., Solid Phase Microextraction Devices Prepared on Plastic Support as Potential Single-Use Samplers for Bioanalytical Applications. Analytical Chemistry 87(19):9722-9730 (2015).
Shelbourne, Montserrat et al. Fast Copper-free Click DNA Ligation by the Ring-strain Promoted Alkyne-Azide Cycloaddition Reaction. Chemical Communications 47(22):6257-6259 (2011).
Spitale, Robert C. et al., Structural Imprints in Vivo Decode RNA Regulatory Mechanisms. Nature 519(7544):486-490 (2015).
Sun, Wei et al., Casting Inorganic Structures With DNA Molds. Science 346(6210):1258361, 1-13 (2014).
U.S. Appl. No. 16/153,071 Office Action dated Aug. 7, 2023.
U.S. Appl. No. 16/153,071 Office Action dated Jul. 8, 2024.
U.S. Appl. No. 16/153,071 Office Action dated Mar. 26, 2025.
U.S. Appl. No. 17/711,731 Office Action dated Apr. 23, 2025.
Zhang, Shuaihua et al., Zeolitic imidazole framework templated synthesis of nanoporous carbon as a novel fiber coating for solid-phase microextraction Analyst 141(3):1127-1135 (2016). Published Online Dec. 24, 2015.
Olivier, Michael. The Invader assay for SNP genotyping. Mutation research 573(1-2):103-110 (2005).
Sano, Takeshi. et al. Immuno-PCR: Very Sensitive Antigen Detection by Means of Specific Antibody-DNA Conjugates. Science 258(5079):120-122 (1992).
U.S. Appl. No. 16/153,071 Office Action dated Nov. 13, 2025.
U.S. Appl. No. 17/711,731 Notice of Allowance dated Oct. 22, 2025.
U.S. Appl. No. 17/906,183 Office Action dated Nov. 20, 2025.
U.S. Appl. No. 17/937,724 Office Action dated Dec. 30, 2025.
Yu, Zhi-gang, and Rebecca Y Lai. Effect of signaling probe conformation on sensor performance of a displacement-based electrochemical DNA sensor. Analytical chemistry 85(6): 3340-3346 (2013).

* cited by examiner

Posterior Colocalization-by-linkage Assays (pCLA)

MULTIPLEXED COLOCALIZATION-BY-LINKAGE ASSAYS FOR THE DETECTION AND ANALYSIS OF ANALYTES

CROSS-REFERENCE

This application claims the benefit of U.S. Provisional Application No. 62/989,571 filed on Mar. 13, 2020, and U.S. Provisional Application No. 63/086,536 filed on Oct. 1, 2020, which applications are incorporated herein by reference.

INCORPORATION-BY-REFERENCE OF MATERIAL SUBMITTED ELECTRONICALLY

The instant application contains a Sequence Listing which has been submitted in ASCII text format via EFS-Web and is hereby incorporated by reference in its entirety. Said ASCII text copy, created on Jul. 8, 2026, is named 57392-703.201_ST25.txt and is 9,430 bytes in size.

BACKGROUND

Rapid and specific detection of biological cells and biomolecules, such as red blood cells, white blood cells, platelets, proteins, DNA, and RNA, has become increasingly important in diverse fields such as genomics, proteomics, diagnostics, therapeutics, and pathological studies. For example, the rapid and accurate detection of specific antigens and viruses is critical for combating pandemic diseases such as AIDS, flu, and other infectious diseases. The maturation of genomic technologies and advances in personalized medicine will require faster and more sensitive assays for detecting and quantifying large numbers of cells and biomolecules. Advances in medical research will increasingly rely on the accurate, timely, and cost-effective assessment of multiple proteins through proteomics. However, current automated, highly-sensitive and low-cost assays cannot be multiplexed efficiently or effectively.

SUMMARY

Provided herein are compositions and methods for the high resolution detecting and/or quantifying an analyte within a sample. The provided compositions and methods described herein, provide, in part, advantages that enable the high resolution and multiplexed detection analytes in a sample. Accordingly, provided herein are methods of detecting and/or quantifying an analyte in a sample, the method comprising: (a) contacting the sample with a complex comprising: (i) a support, (ii) a capture reagent releasably coupled to the support, (iii) a detection reagent releasably coupled to the support, wherein the capture reagent and detection reagents are configured to simultaneously bind to the analyte; (b) decoupling the detection reagent from the support; (c) decoupling the capture reagent from the support; and (d) detecting one or both of the released detection reagent or capture reagent.

In some embodiments, provided is a method of any of the preceding embodiments, wherein the support further comprises a first anchor element and second anchor element coupled thereto, and wherein the capture reagent is releasably coupled to the support via the first anchor element and the detection reagent is releasably coupled to the support via the second anchor element. In some embodiments, provided is a method of any of the preceding embodiments, wherein the capture reagent comprises a first hook element coupled thereto, and wherein the first hook element is releasably coupled to the first anchor element. In some embodiments, provided is a method of any of the preceding embodiments, wherein the detection reagent comprises a second hook element coupled thereto, and wherein the second hook element is releasably coupled to the second anchor element. In some embodiments, provided is a method of any of the preceding embodiments, wherein (1) the capture reagent comprises a first hook element coupled thereto, and wherein the first hook element is releasably coupled to the first anchor element, and (2) the detection reagent comprises a second hook element coupled thereto, and wherein the second hook element is releasably coupled to the second anchor element.

In some embodiments, provided is a method of any of the preceding embodiments, wherein the support further comprises an anchor element coupled thereto, and wherein the capture reagent is releasably coupled to the support via the anchor element and the detection reagent is releasably coupled to the support via the anchor element. In some embodiments, provided is a method of any of the preceding embodiments, wherein (1) the capture reagent comprises a first hook element coupled thereto, and wherein the first hook element is releasably coupled to the anchor element, and (2) the detection reagent comprises a second hook element coupled thereto, and wherein the second hook element is releasably coupled to the anchor element. In some embodiments, provided is a method of any of the preceding embodiments, wherein (b), decoupling comprises applying a stimulus that decouples the detection reagent from the support. In some embodiments, provided is a method of any of the preceding embodiments, wherein (c), decoupling comprises applying a stimulus that decouples the capture reagent from the support. In some embodiments, provided is a method of any of the preceding embodiments, wherein the stimulus is a thermal stimulus, photo-stimulus, chemical stimulus, a mechanical stimulus, a radiation stimulus, a biological stimulus, or any combination thereof.

In some embodiments, provided is a method of any of the preceding embodiments, wherein (b), decoupling comprises providing a displacer agent that decouples the detection reagent from the support. In some embodiments, provided is a method of any of the preceding embodiments, wherein (c), decoupling comprises providing a displacer agent that decouples the capture reagent from the support. In some embodiments, provided is a method of any of the preceding embodiments, wherein (d), detecting comprises identifying a nucleic acid molecule corresponding to the detection reagent or capture reagent. In some embodiments, provided is a method of any of the preceding embodiments, wherein identifying the nucleic acid molecule comprises performing a sequencing reaction, a PCR, a qPCR, or nucleic acid probe-based assay. In some embodiments, provided is a method of any of the preceding embodiments, wherein the nucleic acid molecule comprises a barcode sequence, unique molecular identifier sequence, a primer binding sequence, or a combination thereof.

In some embodiments, provided is a method of any of the preceding embodiments, wherein (b), decoupling comprises providing a detectable displacer agent that decouples the detection reagent from the support. In some embodiments, provided is a method of any of the preceding embodiments, wherein the detectable displacer agent is an oligonucleotide. In some embodiments, provided is a method of any of the preceding embodiments, wherein the oligonucleotide comprises a barcode sequence, unique molecular identifier sequence, a primer binding sequence, or a combination thereof. In some embodiments, provided is a method of any of the preceding embodiments, wherein (c), decoupling comprises providing a detectable displacer agent that decouples the capture reagent from the support. In some embodiments, provided is a method of any of the preceding embodiments, wherein the detectable displacer agent is an oligonucleotide. In some embodiments, provided is a method of any of the preceding embodiments, wherein the oligonucleotide comprises a barcode sequence, unique molecular identifier sequence, a primer binding sequence, or a combination thereof. In some embodiments, provided is a method of any of the preceding embodiments, wherein (e), detecting comprises detecting the displacer agent.

In some embodiments, provided is a method of any of the preceding embodiments, wherein subsequent to (d), the method comprises capturing the detection reagent and/or the capture reagent on a second support.

Also provided are methods of processing an analyte for the detection and quantification of the analyte, the method comprising: (a) contacting a sample comprising the analyte with a complex comprising: (i) a support, (ii) a capture reagent attached to the support, (iii) a detection reagent attached to the support, thereby generating an analyte bound complex comprising the analyte coupled to the capture reagent and the detection reagent; (b) decoupling the detection reagent from the support; and (c) decoupling the capture reagent from the support, wherein the detection reagent comprises a detectable element.

In some embodiments, provided is a method of any of the preceding embodiments, wherein the detectable element is a nucleic acid sequence configured to be detected by a sequencing reaction, a nucleic acid amplification reaction, or couple to a labeled probe (e.g. a detectable displacer agent). In some embodiments, provided is a method of any of the preceding embodiments, wherein the support further comprises a first anchor element and second anchor element coupled thereto, and wherein the capture reagent is releasably coupled to the support via the first anchor element and the detection reagent is releasably coupled to the support via the second anchor element. In some embodiments, provided is a method of any of the preceding embodiments, wherein the first anchor element comprises a first anchor oligonucleotide and the second anchor element comprise a second anchor oligonucleotide. In some embodiments, provided is a method of any of the preceding embodiments, wherein the capture reagent comprises a first hook element coupled thereto, and wherein the first hook element is releasably coupled to the first anchor element. In some embodiments, provided is a method of any of the preceding embodiments, wherein the detection reagent comprises a second hook element coupled thereto, and wherein the second hook element is releasably coupled to the second anchor element. In some embodiments, provided is a method of any of the preceding embodiments, wherein (1) the capture reagent comprises a first hook element coupled thereto, and wherein the first hook element is releasably coupled to the first anchor element, and (2) the detection reagent comprises a second hook element coupled thereto, and wherein the second hook element is releasably coupled to the second anchor element. In some embodiments, provided is a method of any of the preceding embodiments, wherein the support further comprises an anchor element coupled thereto, and wherein the capture reagent is releasably coupled to the support via the anchor element and the detection reagent is releasably coupled to the support via the anchor element. In some embodiments, provided is a method of any of the preceding embodiments, wherein (1) the capture reagent comprises a first hook element coupled thereto, and wherein the first hook element is releasably coupled to the anchor element, and (2) the detection reagent comprises a second hook element coupled thereto, and wherein the second hook element is releasably coupled to the anchor element.

In some embodiments, provided is a method of any of the preceding embodiments, wherein the first hook element comprises a first hook oligonucleotide and the second hook element comprises a second hook oligonucleotide. In some embodiments, provided is a method of any of the preceding embodiments, wherein one or both of the first hook oligonucleotide and the second hook oligonucleotide comprise a barcode sequence, unique molecular identifier sequence, a primer binding sequence, or a combination thereof. In some embodiments, provided is a method of any of the preceding embodiments, wherein the method further comprises (e) detecting the detection reagent. In some embodiments, provided is a method of any of the preceding embodiments, wherein (e), detecting comprises identifying a nucleic acid molecule corresponding to the detection reagent. In some embodiments, provided is a method of any of the preceding embodiments, wherein identifying the nucleic acid molecule comprises performing a sequencing reaction, a PCR, a qPCR, or nucleic acid probe-based assay. In some embodiments, provided is a method of any of the preceding embodiments, wherein the nucleic acid molecule comprises a barcode sequence, unique molecular identifier sequence, a primer binding sequence, or a combination thereof.

In some embodiments, provided is a method of any of the preceding embodiments, wherein (b), decoupling comprises providing a detectable displacer agent that decouples the detection reagent from the support. In some embodiments, provided is a method of any of the preceding embodiments, wherein the detectable displacer agent is an oligonucleotide. In some embodiments, provided is a method of any of the preceding embodiments, wherein the oligonucleotide comprises a barcode sequence, unique molecular identifier sequence, a primer binding sequence, or a combination thereof.

In some embodiments, provided is a method of any of the preceding embodiments, wherein (b) or (c), decoupling comprises providing a detectable displacer agent that decouples the capture reagent or detection reagent from the support. In some embodiments, provided is a method of any of the preceding embodiments, wherein the detectable displacer agent is an oligonucleotide. In some embodiments, provided is a method of any of the preceding embodiments, wherein the oligonucleotide comprises a barcode sequence, unique molecular identifier sequence, a primer binding sequence, or a combination thereof. In some embodiments, provided is a method of any of the preceding embodiments, wherein subsequent to (d), the method comprises capturing the detection reagent and/or the capture reagent on a second support.

Further provided are methods of detecting and/or quantifying an analyte in a sample, the method comprising: (a) contacting the sample with a complex comprising: (i) a support, and (ii) a capture reagent releasably coupled to the support; (b) providing a detection reagent, wherein the capture reagent and detection reagent are configured to simultaneously bind to the analyte; (c) decoupling the detection reagent from the support; (d) decoupling the capture reagent from the support; and (e) detecting one or both of the released detection reagent or capture reagent. Also provided are methods of processing an analyte for the detection and quantification of the analyte, the method comprising: (a)

contacting a sample comprising the analyte with a complex comprising: (i) a support, and (ii) a capture reagent attached to the support, thereby generating the analyte coupled to the capture reagent; (b) contacting the analyte bound complex with a detection reagent configured to couple to the analyte and couple to the support, thereby generating an analyte bound complex comprising the analyte coupled to the capture reagent and the detection reagent; and (c) decoupling at least one of the capture reagent and the detection reagent from the support, wherein at least one of the detection reagent comprises a detectable element. In some embodiments, provided is a method of any of the preceding embodiments, wherein at least one of the capture reagent and the detection reagent are configured to be detected by a sequencing reaction, a nucleic acid amplification reaction (e.g. PCR), or coupling to labeling agent (e.g. a displacer reagent). In some embodiments, provided is a method of any of the preceding embodiments, wherein the method further comprises (d) detecting at least one of the capture reagent and the detection reagent.

In some embodiments, provided is a method of any of the preceding embodiments, wherein the support further comprises a first anchor element and second anchor element coupled thereto, and wherein the capture reagent is releasably coupled to the support via the first anchor element and the detection reagent is releasably coupled to the support via the second anchor element. In some embodiments, provided is a method of any of the preceding embodiments, wherein the first anchor element comprises a first anchor oligonucleotide and the second anchor element comprise a second anchor oligonucleotide. In some embodiments, provided is a method of any of the preceding embodiments, wherein the capture reagent comprises a first hook element coupled thereto, and wherein the first hook element is releasably coupled to the first anchor element. In some embodiments, provided is a method of any of the preceding embodiments, wherein the detection reagent comprises a second hook element coupled thereto, and wherein the second hook element is configured to releasably couple to the second anchor element. In some embodiments, provided is a method of any of the preceding embodiments, wherein (i) the capture reagent comprises a first hook element coupled thereto, and wherein the first hook element is releasably coupled to the first anchor element, and (ii) the detection reagent comprises a second hook element coupled thereto, and wherein the second hook element is configured to releasably couple to the second anchor element.

In some embodiments, provided is a method of any of the preceding embodiments, wherein the support further comprises an anchor element coupled thereto, and wherein the capture reagent is releasably coupled to the support via the anchor element is releasably coupled to the support via the anchor element and the detection reagent is configured to releasably couple to the support via the anchor element. In some embodiments, provided is a method of any of the preceding embodiments, wherein (i) the capture reagent comprises a first hook element coupled thereto, and wherein the first hook element is releasably coupled to the anchor element, and (ii) the detection reagent comprises a second hook element coupled thereto, and wherein the second hook element is releasably coupled to the anchor element. In some embodiments, provided is a method of any of the preceding embodiments, wherein the first hook element comprises a first hook oligonucleotide and the second hook element comprises a second hook oligonucleotide. In some embodiments, provided is a method of any of the preceding embodiments, wherein one or both of the first hook oligonucleotide and the second hook oligonucleotide comprise a barcode sequence, unique molecular identifier sequence, a primer binding sequence, or a combination thereof.

In some embodiments, provided is a method of any of the preceding embodiments, wherein (c), decoupling comprises providing a detectable displacer agent that decouples the detection reagent from the support. In some embodiments, provided is a method of any of the preceding embodiments, wherein the detectable displacer agent is an oligonucleotide. In some embodiments, provided is a method of any of the preceding embodiments, wherein the oligonucleotide comprises a barcode sequence, unique molecular identifier sequence, a primer binding sequence, or a combination thereof. In some embodiments, provided is a method of any of the preceding embodiments, wherein (c), decoupling comprises providing a detectable displacer agent that decouples the capture reagent from the support. In some embodiments, provided is a method of any of the preceding embodiments, wherein the detectable displacer agent is an oligonucleotide. In some embodiments, provided is a method of any of the preceding embodiments, wherein the oligonucleotide comprises a barcode sequence, unique molecular identifier sequence, a primer binding sequence, or a combination thereof.

In some embodiments, provided is a method of any of the preceding embodiments, wherein (i) the analyte is an antibody molecule, (ii) the capture reagent is an antigen, and (iii) the detection reagent is specific for an immunoglobulin class IgG, IgM, IgA, IgD, or IgE. In some embodiments, provided is a method of any of the preceding embodiments, wherein detection reagent comprises an anti-IgG, -IgM, -IgA, -IgD, or -IgE antibody. In some embodiments, provided is a method of any of the preceding embodiments, wherein detection reagent comprises an protein A, protein G, or protein M. In some embodiments, provided is a method of any of the preceding embodiments, wherein (i) the analyte is protein comprising posttranslational modification, (ii) the capture reagent binds the protein, and (iii) the detection reagent is specific for the posttranslational modification or the protein comprising the posttranslational modification.

Provided herein are methods of detecting analytes in a sample, the method comprising: (a) contacting the sample with a the complex comprising: (i) a support, (ii) a first capture reagent and a first detection reagent coupled to the support, wherein the first capture reagent and first detection reagent are configured to simultaneously couple to a first analyte in said sample, and (iii) a second capture reagent and a second detection reagent coupled to the support, wherein the second capture reagent and second detection reagent are configured to simultaneously couple to the second analyte; (b) providing a first displacer reagent configured to decouple the first detection reagent and/or second detection reagent from the support; (c) providing a second displacer reagent configured to decouple the first capture reagent and/or second capture reagent from the support; and (d) detecting at least one of the (i) decoupled first capture reagent and decoupled first detection reagent, and/or (ii) decoupled second capture reagent and decoupled second detection reagent. Also provided are methods of processing an analyte for the detection and quantification of the analyte, the method comprising: (a) contacting the sample with a the complex comprising: (i) a support, (ii) a first capture reagent and a first detection reagent coupled to the support, wherein the first capture reagent and first detection reagent are configured to simultaneously couple to a first analyte in said sample, and (iii) a second capture reagent and a second detection reagent coupled to the support, wherein the second capture reagent and second detection reagent are configured to simultaneously couple to the second analyte; (b) contacting the analyte bound complex with a detection reagent configured to couple to the analyte and couple to the support, thereby generating an analyte bound complex comprising the analyte coupled to the capture reagent and the detection reagent; and (c) decoupling at least one of the capture reagent and the detection reagent from the support; and wherein at least one of (i) the first capture reagent and second capture reagent, and/or (ii) the first detection reagent and second detection reagent comprise a detectable element. In some embodiments, provided is a method of any of the preceding embodiments, wherein at least one of (i) the first capture reagent and second capture reagent, and/or (ii) the first detection reagent and second detection reagent are configured to be detected by a sequencing reaction, a nucleic acid amplification reaction (e.g. PCR), or coupling to labeling agent (e.g. a displacer reagent). In some embodiments, provided is a method of any of the preceding embodiments, wherein the method further comprises (d) detecting at least one of the (i) decoupled first capture reagent and decoupled first detection reagent, and/or (ii) decoupled second capture reagent and decoupled second detection reagent.

In some embodiments, provided is a method of any of the preceding embodiments, wherein the support further comprises a first anchor element, second anchor element, a third anchor element, and a fourth anchor element coupled thereto, and wherein (i) the first capture reagent is releasably coupled to the support via the first anchor element and the first detection reagent is releasably coupled to the support via the second anchor element, and (ii) the second capture reagent is releasably coupled to the support via the third anchor element and the second detection reagent is releasably coupled to the support via the fourth anchor element. In some embodiments, provided is a method of any of the preceding embodiments, wherein the first anchor element comprises a first anchor oligonucleotide, the second anchor element comprise a second anchor oligonucleotide, the second anchor element comprise a second anchor oligonucleotide. In some embodiments, provided is a method of any of the preceding embodiments, wherein (i) the first capture reagent comprises a first hook element coupled thereto and the second capture reagent comprises a third hook element coupled thereto, and (ii) the first hook element is releasably coupled to the first anchor element and the second hook element is releasably coupled to the third anchor element. In some embodiments, provided is a method of any of the preceding embodiments, wherein (i) the first detection reagent comprises a second hook element coupled thereto and the fourth detection hook element coupled thereto, and (ii) the second hook element is configured to releasably couple to the second anchor element and the fourth hook element is configured to releasably couple to the fourth anchor element.

In some embodiments, provided is a method of any of the preceding embodiments, wherein (i) the first capture reagent comprises a first hook element coupled thereto and the second capture reagent comprises a third hook element coupled thereto, and (ii) the first hook element is releasably coupled to the first anchor element and the second hook element is releasably coupled to the third anchor element; and wherein (iii) the first detection reagent comprises a second hook element coupled thereto and the fourth detection hook element coupled thereto, and (iv) the second hook element is configured to releasably couple to the second anchor element and the fourth hook element is configured to releasably couple to the fourth anchor element. In some embodiments, provided is a method of any of the preceding embodiments, wherein the support further comprises a first anchor element coupled thereto and a second anchor element coupled thereto, and wherein (i) the first capture reagent is releasably coupled to the support via the first anchor element and the first detection reagent is configured to releasably couple to the support via the first anchor element, and (ii) the second capture reagent is releasably coupled to the support via the second anchor element and the second detection reagent is configured to releasably couple to the support via the second anchor element.

In some embodiments, provided is a method of any of the preceding embodiments, wherein the first hook element comprises a first hook oligonucleotide, the second hook element comprises a second hook oligonucleotide, the third hook element comprises a third hook oligonucleotide, and/or fourth hook element comprises a fourth hook oligonucleotide. In some embodiments, provided is a method of any of the preceding embodiments, wherein at least one of the first hook oligonucleotide, the second hook oligonucleotide, the third hook oligonucleotide, and the fourth hook oligonucleotide comprise a barcode sequence, unique molecular identifier sequence, a primer binding sequence, or a combination thereof. In some embodiments, provided is a method of any of the preceding embodiments, wherein (c), decoupling comprises providing a displacer agent that decouples the capture reagent from the support. In some embodiments, provided is a method of any of the preceding embodiments, wherein the detectable displacer agent is an oligonucleotide. In some embodiments, provided is a method of any of the preceding embodiments, wherein the oligonucleotide is configured to be detected. In some embodiments, provided is a method of any of the preceding embodiments, wherein the oligonucleotide comprises a barcode sequence, unique molecular identifier sequence, a primer binding sequence, or a combination thereof. In some embodiments, provided is a method of any of the preceding embodiments, wherein the oligonucleotide comprises a fluorescent label.

Further provided are co-localization by linkage assay compositions comprising: a complex comprising (i) a support, (ii) a capture reagent releasably coupled to the support, (iii) a detection reagent releasably coupled to the support, wherein the capture reagent and detection reagent are configured to simultaneously bind to the analyte. In some embodiments, provided is a method of any of the preceding embodiments wherein for use in any one of the preceding methods. Also provided are co-localization by linkage assay compositions comprising a complex comprising: (i) a support, (ii) a first capture reagent and a first detection reagent coupled to the support, wherein the first capture reagent and first detection reagent are configured to simultaneously couple to a first analyte in said sample, and (iii) a second capture reagent and a second detection reagent coupled to the support, wherein the second capture reagent and second detection reagent are configured to simultaneously couple to the second analyte.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
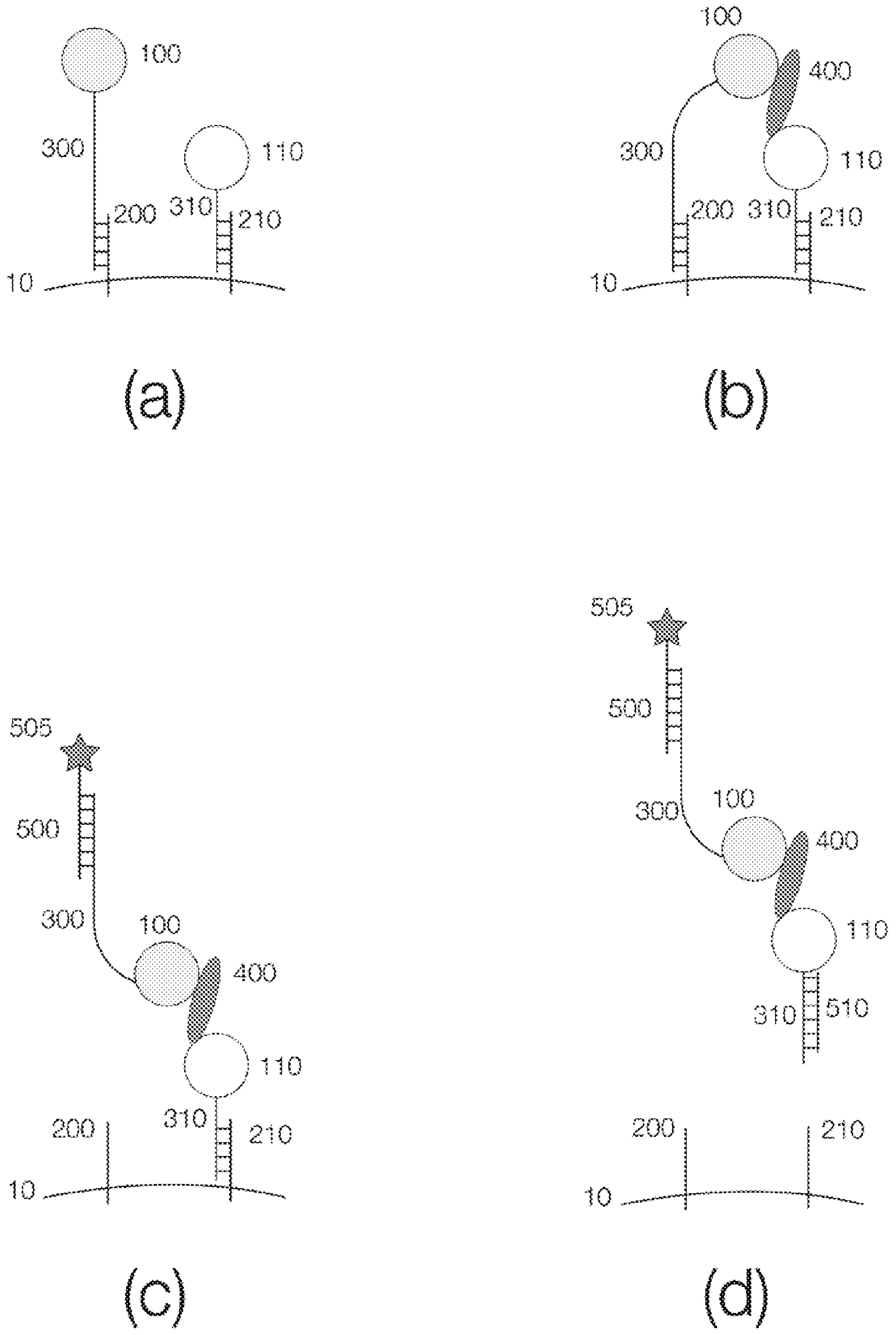
FIG. 1(*a*)-1(*d*) show a schematic of one embodiment of a 1-plex stochastic addCLAMP, wherein two displacer reagents are used to displace the detection and capture reagent from the support.

The sandwich assay is one of the most popular formats for biological assays. In this format, a capture probe molecule is immobilized on a surface. A biological sample containing a target cell or biomolecule of interest is then applied to the surface. The target binds in a concentration dependent manner to the capture probe molecule immobilized on the surface. In a subsequent step, a detection probe molecule is applied to the surface. The detection probe molecule binds to the target biomolecule which is thus “sandwiched” between the capture probe and the detection probe molecules. In some assays, a secondary probe which can bind the detection probe molecule is also applied to the surface. The secondary probe can be conjugated to a label such as a fluorophore, in which case the binding can be detected using a fluorescence scanner or a fluorescence microscope. In some cases, the secondary probe is conjugated to a radioactive element, in which case the radioactivity is detected to read out the assay result. In some cases, the secondary probe is conjugated to an enzyme, in which case a solution containing a substrate is added to the surface and the conversion of the substrate by the enzyme is detected. In all cases the intensity of the signal detected is proportional to the concentration of the target in the biological sample. The requirement of dual recognition in a sandwich assay provides a highly-fidelity signal with low background signal and/or noise and, as a result, high sensitivity detection.

The enzyme-linked immunosorbent assay (ELISA) is a well-known example of a sandwich assay. The ELISA typically uses antibodies and a color change reaction to identify a biomolecule in a biological sample. For example, an ELISA can use a solid-phase enzyme immunoassay (EIA) to detect the presence of a biomolecule, such as an antigen, in a liquid or wet biological sample applied to the solid-phase. ELISAs are often performed in 96-well or 384-well polystyrene plates, which passively bind antibodies and proteins. It is this binding and immobilization of reagents on a solid surface that makes ELISAs so easy to design and perform. Immobilizing the reagents on the microplate surface makes it easy to separate the bound target biomolecules from unbound materials during the assay and to wash away non-specifically bound materials. In addition, the requirement for dual recognition by both capture and detection probe molecules provides high specificity. The ELISA is thus a powerful tool for measuring specific target biomolecules within a crude preparation.

However, current sandwich assays have poor performance when used to measure multiple biomolecules in a sample at the same time (multiplexing). Multiplexed ELISAs are limited by cross-reactivity between reagents such as antibodies, proteins, etc., and are prone to nonspecific signaling as a result. In conventional multiplexed sandwich assays in both array and bead formats, detection antibodies are typically applied as a mixture, but this method gives rise to interactions among reagents that constitute a liability for cross-reactivity. The application of detection antibody mixtures hence leads to spurious binding and generates false-positive signals from non-specific binding events, for example, between a capture and a non-targeted analyte (illustrated in FIG. 4 herein) that can be difficult to distinguish from the real target protein-binding signal. Such reagent-driven cross-reactivity is an inherent problem in MSAs and scales quadratically with the number of targets, severely limiting the scale of multiplexing. Due to problems with cross-reactivity, current MSAs are generally limited to 30-40 targets. Even then, lengthy and costly optimization protocols are needed to uncover and remove cross-reactive reagents (e.g., antibodies), which severely limits the applicability of these assays and increases their cost.

Cross-reactivity also hinders other types of multiplexed assays. For example, accurate protein phosphorylation analysis can be used to reveal cellular signaling events not evident from protein expression levels. For example, current methods and workflows for quantifying the fraction of post-translational modification (PTM) of a specific protein are severely limited in multiplexing because PTM-specific antibodies often possess inadequate specificity for the protein itself (that is, a phosphor-specific antibody is highly susceptible to the problem of reagent-driven cross-reactivity). As a result, conventional PTM panels are not multiplexed.

Conventional sandwich immunoassays are also not suitable for analyzing protein-protein interactions. Protein-protein interactions are a key part of cellular processes and understanding modulators of these interactions is extremely important to address correlating diseases. However, the use of detection antibody mixtures allows unwanted interactions and leads to spurious binding that can obfuscate the interaction signals. Current multiplexed sandwich assays are also costly because expensive reagents such as antibodies are used inefficiently during manufacturing and performance of the assays. For example, the addition of antibody mixtures in solution necessitates high concentrations (nanomolar), whereas the amount needed to bind to proteins to quantitate for microarrays or microbeads is 3 orders of magnitude less, which corresponds to a 99.9% loss of antibodies. Further, the sensitivity of a given sandwich immunoassay is highly affected by background signal which is often due to non-specific binding and/or incomplete washing of labeled detection antibodies. Methods to reduce incomplete washing by increasing washing cycles and including additive reagents have been used, however these methods result in increased assay times and assay complexity.

The compositions and methods described herein (i.e. addCLAMP, posterior-CLAMP, and poly-CLAMP compositions and methods) provide solutions to the limitations and challenges associated with such immunoassays because the compositions and the methods described enable, in part, high resolution detection of analytes (e.g. characterized by highly sensitive readouts and reduced background) and the highly multiplexed (e.g. the parallel or high throughput detection and/or quantification of multiple analytes). The compositions and methods described herein therefore, in an aspect, increase the efficiency of detection of analytes in a sample (e.g. the detection of a number of analytes over time). For example, the compositions and methods of certain embodiments described herein utilize detection and capture reagents that can be decoupled from a support Co-Localization by Linkage Assay The colocalization-by-linkage (CL) sandwich assay (CLA) allows multiplexed measurement of antibodies while also overcoming the detectable non-specific binding issue. Generally, in CLA, a support is provided that is coated with multiple binders and flexible tethers that together form a fully integrated sensor. More specifically, capture binders (e.g. capture reagents) (CB) and detection binders (e.g. detection reagents) (DB) are provided pre-assembled to the support before contacting with the sample. The binders can bind simultaneously to the analyte of interest and one or both of the binders are tethered by a flexible linker so as to allow formation of sandwich complex with the analyte when the sample is provided. Detection of the analyte presence proceeds using the "release-dependent transduction" (RDT) principle, which relies on simultaneously labeling the detection binder (e.g. detection reagent) and displacing it from the support. This step can be performed using DNA oligonucleotide displacement, among other strategies. Importantly, detection binders (e.g. detection reagents) (DB) only become detectably labeled upon correct displacement, and remains on the support if it is bound to the analyte which itself is bound to the support via the CB. If on the other hand the analyte is not present, the displaced and labeled detection binders (e.g. detection reagents) (DB) will be washed from the support. Importantly, non-displaced detection binders (e.g. detection reagents) (DB) do not yield a detectable background signal because they are only detectable if they have indeed been displaced.

In general, sandwich assays can be designed and fabricated to measure or detect multiple analytes in parallel (also called multiplexing). Multiplexed sandwich assays (MSAs) can be carried out using microarrays, such as DNA microarrays, protein microarrays or antibody microarrays. A microarray is a collection of microscopic spots containing biomolecules attached to a substrate surface, such as a glass, plastic or silicon, which thereby form a "microscopic" array. Such microarrays can be used for example to measure the expression levels of large numbers of genes or proteins simultaneously. The biomolecules, such as DNAs, proteins or antibodies, on a microarray chip are typically detected through optical readout of fluorescent labels attached to a target molecule that is specifically attached or hybridized to a probe molecule. The labels used can consist for example of an enzyme, radioisotopes, or a fluorophore.

MSAs can also be conducted on particles. In this case, particles suspended in solution are attached to biomolecules necessary to capture the targets of interest, such as proteins or specific DNA molecules. To conduct assays in multiplex, the particles must be encoded to allow the different assays in solution to be distinguished. A popular format is spectrally-encoded microparticles, which are encoded using fluorescent or luminescent dyes. Particles can also be encoded graphically-hence they are often referred to as "barcoded particles". Particle sizes can range in size from nanometer (nanoparticles) to micrometer (microparticles). Of these, fluorescently-encoded microparticles can be read-out rapidly and with high-throughput on cytometers.

In some embodiments, there is provided a dual-AB or sandwich assay that can avoid cross-reactivity by colocalizing two ABs (a capture AB (e.g. capture reagent) and a detection AB) on a support prior to exposure to a biological sample containing an analyte of interest. Colocalization on the support does not permit any mixing of different AB pairs (e.g. pairs of affinity reagents) prior to exposure to the analyte, and can thus reduce or eliminate cross-reactivity between reagents and/or background. In an embodiment, there is provided a support attached to a mixture of capture and detection ABs (e.g. detection reagents), where each set of capture and detection ABs (e.g. detection reagents) is capable of binding with an analyte of interest, with the detection AB (e.g. detection reagent) attached to the support, optionally via a releasable linker. In an embodiment, there is provided a support attached to a mixture of capture and detection ABs (e.g. detection reagents), wherein each analyte is capable of binding simultaneously to both a capture AB (e.g. capture reagent) and a detection AB, and wherein the detection AB (e.g. detection reagent) is releasably attached to the support, optionally via a releasable hook strand. Upon release of the detection reagent and/or the hook strand, the corresponding detection AB (e.g. detection reagent) remains on the support only if bound to the analyte in a tertiary complex with a capture AB (e.g. capture reagent).

These embodiments can also be referred to herein as a "colocalization-by-linkage assay" or "CLA". In some embodiments of CLA, the detection AB (e.g. detection reagent) is labeled (i.e., attached to a label). In some embodiments of CLA, the hook strand linking the detection AB (e.g. detection reagent) to the anchoring element or the anchor strand or the anchor strand is labeled (i.e., attached to a label). Generally, the label attached to the detection AB (e.g. detection reagent) or the hook strand is inactive or undetectable, such that the label can be detected after release of the detection AB (e.g. detection reagent) from the support (i.e., after the hook strand is released from the anchoring element or the anchor strand). Signal detection from the label is thus release-dependent (also referred to, in some embodiments, as "displacement-dependent"). In this way, only detection ABs (e.g. detection reagents) bound to the analyte in a tertiary complex with a capture AB (e.g. capture reagent) and released from the anchoring element or the anchor strand will be detected, as unbound detection AB (e.g. detection reagent) will be released from the support (and can be removed e.g., by washing). Background signal can also be reduced since the label is inactive or undetectable prior to release, or if a given hook strand is not released (i.e., due to the release-dependent or displacement-dependent nature of the signal). In some embodiments, therefore, methods and systems provided herein can be referred to as "release-dependent transduction" (or "RDT") or "displacement-dependent detection", to reflect the release-dependent (or displacement-dependent) signal transduction.

In some embodiments, therefore, systems and methods provided herein include an additional level of redundancy to reduce background signal and/or increase sensitivity by the use of release-dependent transduction (RDT). In RDT (release-dependent transduction), signal transduction occurs only if both of the following conditions are satisfied: (i) formation of a tertiary capture AB (e.g. capture reagent)-analyte-detection AB (e.g. detection reagent) complex, and (ii) release of the corresponding detection AB (e.g. detection reagent) and/or hook strand from the anchor strand. In such cases, a non-released detection AB (e.g. detection reagent) and/or hook strand will not contribute to the background signal. This signal transduction mechanism, which we herein refer to as "release-dependent transduction (RDT)", can be achieved through various means. For example, some embodiments can include a label on the hook strand, wherein the label is inactive or undetectable until after the release from the anchoring element or the anchor strand, such that a non-released (e.g., non-displaced) hook strand and/or detection AB) will not contribute to or transduce the signal. In some embodiments of RDT (release-dependent transduction), a hook strand is labeled with a fluorescent dye quenched by a quencher on the anchoring element or the anchor strand or another proximal strand, such that release results in unquenching or activation of the fluorescent dye.

In some embodiments of RDT (release-dependent transduction), the detection reagent and the hook strand are not labeled, and instead the displacer agent is labeled. In this case, the displacer agent hybridizes to the hook strand, displacing it from the anchoring element or the anchor strand, and simultaneously labeling it. If the detection AB (e.g. detection reagent) is not bound to analyte and capture AB (e.g. capture reagent) in a tertiary complex, then the hook strand, the displacer agent, and the label are washed off the support. Since the label is attached to the displacer agent, the label is only present on the support when both conditions are met: (i) release or displacement from the anchoring element or the anchor strand has occurred, and (ii) analyte has bound to both capture and detection ABs (e.g. detection reagents). It will be appreciated that other embodiments of RDT (release-dependent transduction) are possible, and the mechanism of RDT (release-dependent transduction) is not meant to be particularly limited.

As encompassed herein, many ABs targeting many different analytes can be mixed in the same assay volume (i.e., multiplexing); interaction between different ABs on different supports (or between different ABs on different locations/positions on the same support) are limited by the linkages to the support(s), so that interaction between ABs from different supports/locations is avoided. This is in contrast to conventional multiplexing technologies that can not limit interactions between ABs when all ABs are mixed in solution. Further, with methods and systems described herein, different microparticle populations can be fabricated separately in large batches, each containing a different AB capture-detection pair needed to detect a specific antigen, ensuring that cross-reactivity does not occur during manufacturing.

Figure 16:
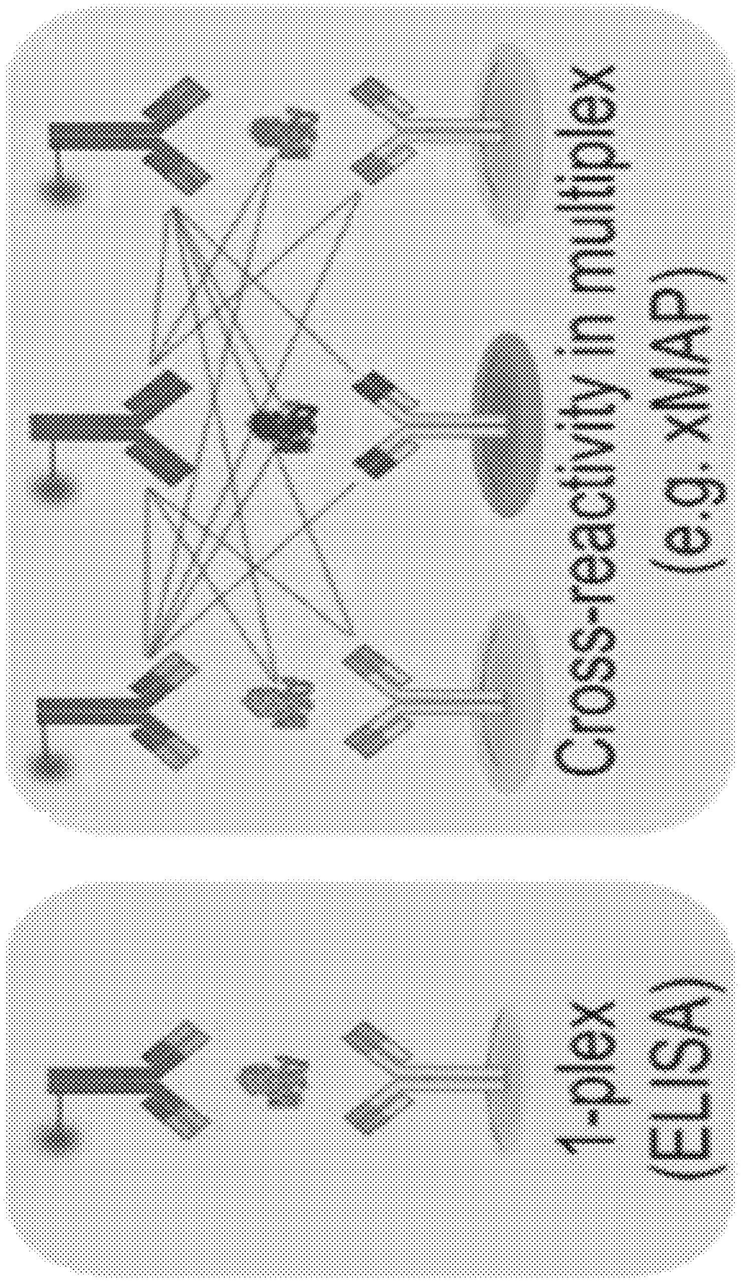
FIG. 16 shows a schematic representing cross reactivity and multiplexing problems associated with traditional sandwich ELISA assays.

In some embodiments, multiplexed CLA methods and systems can thus avoid the cross-reactivity scenarios shown in FIG. 16. For example, as will be appreciated by those skilled in the art, the colocalization of cognate capture and detection ABs (e.g. detection reagents) on their respective supports (e.g., microparticles) will eliminate unwanted interactions such as, for example, binding between non-cognate detection and detection ABs (e.g. detection reagents). In addition, those skilled in the art will recognize that, as opposed to conventional multiplexed sandwich assays, analytes that indiscriminately bind, or stick, to off-target supports cannot be detected by their cognate detection AB (e.g. detection reagent) in methods and systems provided herein, and hence do not contribute to increase the background signal.

Analyte-Dependent Displacement CLA (Add-CLA) Compositions and Methods

Conventional sandwich assays generally rely on the presence of labeled detection ABs (e.g. detection reagents) to transduce a signal and detect the presence of an analyte. However, in contrast to conventional assays, in systems and methods provided by the colocalization-by-linkage (CLA) sandwich assay previously described in U.S. Pre-Grant Publication No. US20200319173, the detection AB (e.g. detection reagent) is unlabeled and detection proceeds instead using the "release-dependent transduction" (RDT) principle. In CLA, a support is provided that is coated with multiple binders and flexible tethers that together form a fully integrated sensor. More specifically, capture binders (e.g. capture reagents) (CB) and detection binders (e.g. detection reagents) (DB) are provided pre-assembled to the support before contacting with the sample. In CLA, the detection AB (e.g. detection reagent) v and/or the hook strand optionally linked thereto can remain on the support only when a tertiary complex is formed with the analyte and the capture AB (e.g. capture reagent). It will be appreciated that, if the detection reagent and/or the hook strand is not successfully or completely released from the anchor strand, then it can remain on the support even in the absence of the analyte. Importantly, the detection binders (e.g. detection reagents) (DB) only become detectably labeled upon correct displacement, and remains on the support if it is bound to the analyte which itself is bound to the support via the CB. If on the other hand the analyte is not present, the displaced and labeled detection binder (e.g. detection reagent) (e.g. detection reagent) (DB) will be washed from the support. Importantly, non-displaced detection binder (e.g. detection reagent) (e.g. detection reagent) (DB) do not yield a detectable background signal because they are only detectable if they have indeed been displaced.

The use of detectably-labeled displacers in the RDT (release-dependent transduction) principle in CLA facilitates readout with reduced background signal and increased detection sensitivity. The RDT (release-dependent transduction) reduces background signal compared to CLA embodiments where the detection reagent, such as detection antibody, is labeled and assembled on the surface ahead of the assay. In such cases where the detection antibody is detectably labeled, achieving a minimal background signal requires a full release.

On the other hand, the methods and systems utilizing CLA principle for analyte detection are not favorable for situations when the detection binders (e.g. detection reagents) (DB), such as an IgG antibody, is "sticky" and non-specifically binds to the surface. In such cases, sticky antibodies used as the detection binder (e.g. detection reagent) result in increased background signal. More specifically, even when the hook oligo is successfully released, and when the analyte is not present, the detection binders (e.g. detection reagents) (DB)-hook oligo-displacer oligo complex remains on the surface, and since the displacer oligo is detectably labeled, results in increased background signals. It will be appreciated by those skilled in the art, detection antibody sticking to surfaces are a major component of background signal and assay noise in an assay.

The analyte-dependent displacement CLA (add-CLA) compositions and methods described herein are based, at least in part, on the design and implementation of new assay mechanics, including releasable or reversible linkages between reagents and supports, and various signal transduction and read-out methods. In certain instances, the analyte-dependent displacement CLA (add-CLA) compositions and methods provided herein reduce or eliminate one more sources of background signal in CLA and, more generally, highly multiplexed assays. In some embodiments, the methods and systems provided in this disclosure relate to a modified CLA with additional levels of redundancy to avoid false positive signals and further improve sensitivity.

In some analyte-dependent displacement CLA (add-CLA) embodiments, a support is provided with a capture binder (e.g. capture reagent) and a detection binder (e.g. detection reagent) configured to binder to bind an analyte simultaneously. After contacting the support with the sample, the detection binder (e.g. detection reagent) is selectively displaced from the support. Subsequently, the capture binder (e.g. capture reagent) is selectively displaced from the support, and the presence of the detection binder (e.g. detection reagent) in solution is measured or characterized. This signal transduction mechanism provides an additional level of redundancy wherein the presence of the detection binder (e.g. detection reagent) in solution is only possible when the analyte is bound to capture and detection binders (e.g. detection reagents). After the capture binders (e.g. capture reagents) are selectively displaced from the support, the only capture binders (e.g. capture reagents) remaining on the support are (i) capture binders (e.g. capture reagents) bound to the analyte, and (ii) capture binders (e.g. capture reagents) non-specifically sticking on the support. After the detection binders (e.g. detection reagents) are selectively displaced from the support, the only detection binders (e.g. detection reagents) that get displaced to the solution are those bound to the capture binder (e.g. capture reagent) via a tertiary capture binder (e.g. capture reagent)-analyte-detection binder (e.g. detection reagent) complex. In other words, in the instance where a capture or detection binder (e.g. detection reagent) is sticking to the surface, no signal will be generated. As such, this "analyte-dependent displacement" colocalization-by-linkage assay (add-CLA) reduces background compared to CLA.

In some add-CLA embodiments, a support is provided with a capture binder (e.g. capture reagent) and a detection binder (e.g. detection reagent) each coupled to the surface via a capture linker and detection linker, respectively, wherein the capture and detection binders (e.g. detection reagents) are configured to bind an analyte simultaneously. A first displacer is provided, wherein the first displacer is configured to bind to the detection linker and displace the detection linker from the support. A second displacer is provided thereafter, wherein the second displacer is configured to bind to the capture linker and displace the capture linker from the support. If the analyte was present and was simultaneously bound by the capture and detection binders (e.g. detection reagents), the addition of the second displacer would release the entire tertiary complex composed of first binder-analyte-second binder. Thereafter, the presence of (1) the detection binder, (2) the detection linker, and/or (3) the first displacer in solution is detected and quantified. This signal transduction mechanism provides an additional level of redundancy wherein the presence of the detection binder, detection linker, or first displacer is only measured in solution when all of the following is true: (i) analyte binds to capture and detection binders (e.g. detection reagents), (ii) first displacer displaces the detection binder (e.g. detection reagent) from the support but the detection binder (e.g. detection reagent) remains bound on the analyte, (iii) the second displacer releases the entire complex comprising of: capture binder, capture linker, analyte, detection binder, detection linker and first displacer. In other words, in the instance where capture or detection binders are sticking to the surface, no signal will be generated. As such, this "analyte-dependent displacement" colocalization-by-linkage assay (add-CLA) reduces background compared to CLA.

[[BZ to Reference New Figures]]

Exemplifying the compositions and methods described herein, FIG. 1 demonstrates an analyte-dependent displacement colocalization-by-linkage on microparticles (add-CLAMP) assay composition. As shown in FIG. 1*a*, the colocalization-by-linkage assay composition is assembled on a microparticle support (10) and comprises (1) a detection reagent (100), and (2) a capture reagent (110). Each of the detection and capture reagents comprise a hook oligonucleotide (300, 310 respectively). In this embodiment, the detection reagent hook oligonucleotide (300) is hybridized to a first anchor oligonucleotide (200) which is attached to the support, and the capture reagent hook oligonucleotide (310) is hybridized to a second anchor oligonucleotide (210) which is attached to the support. The detection and capture reagents are specific for an analyte and are configured to be capable of binding said analyte. After incubation with a sample comprising a plurality of analytes (FIG. 1*b*), a complex between an analyte (400) and the detection and capture reagents is generated. A first detectably labeled displacer reagent (500), labeled with a fluorophore (505), is provided (FIG. 1*c*), and the first detectably labeled displacer reagent specifically binds to the detection reagent hook element, displacing the detection reagent from the first anchor oligonucleotide. Any unbound detection reagent is displaced from the detection complex and removed. A second detectably labeled displacer reagent (510) is provided (FIG. 1*d*), and the second displacer reagent specifically binds to the capture reagent hook element, displacing the capture reagent from the first anchor oligonucleotide, releasing the detection complex. The released detection reagent hook element can then be processed, and/or the first detectably labeled displacer reagent can be analyzed, to identify the detection reagent and hence quantify the analyte.

Figure 2:
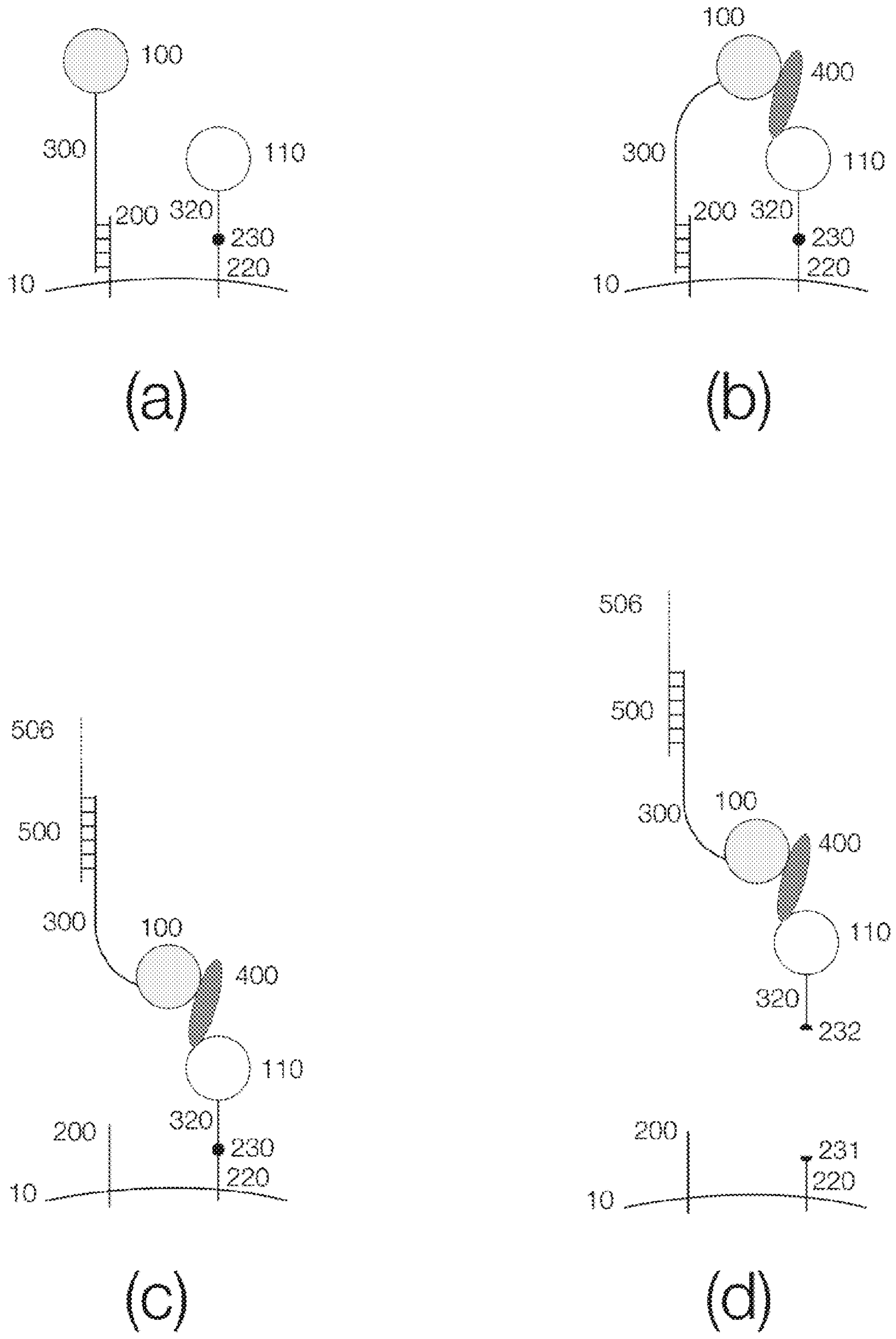
FIG. 2(*a*)-2(*d*) show a schematic of one embodiment of a 1-plex stochastic addCLAMP, wherein a displacer reagent is used to displace the detection reagent from the support and a cleaving agent is used to displace the capture reagent from the support.

Exemplifying the compositions and methods described herein, FIG. 2 demonstrates an analyte-dependent displacement colocalization-by-linkage on microparticles (add-CLAMP) assay composition. As shown in FIG. 2*a*, the colocalization-by-linkage assay composition is assembled on a microparticle support (10) and comprises (1) a detection reagent (100), and (2) a capture reagent (110). Each of the detection and capture reagents comprise a hook oligonucleotide (300, 320 respectively). In this embodiment, the detection reagent hook oligonucleotide (300) is hybridized to a first anchor oligonucleotide (200) which is attached to the support. In this embodiment, the capture reagent hook oligonucleotide (320) is releasably coupled via a cleavable linker element (230) to a second anchor oligonucleotide (220) which is attached to the support. The detection and capture reagents are specific for an analyte and are configured to be capable of binding said analyte. After incubation with a sample comprising a plurality of analytes (FIG. 2*b*), a complex between an analyte (400) and the detection and capture reagents is generated. A detectably labeled displacer reagent (500), labeled with an identifiable DNA sequence (506), is provided (FIG. 2*c*), and the detectably labeled displacer reagent specifically binds to the detection reagent hook element, displacing the detection reagent from the first anchor oligonucleotide. Any displaced detection reagent that is not coupled to the support via the detection complex is removed. A cleaving agent specific for the cleavable linker element (230) cleaves the cleavable linker element so that the capture reagent hook element is released from the support (FIG. 2*d*). Some or none of the cleaved cleavable linker element (232) remains coupled to capture reagent hook element, and some or none of the cleaved cleavable linker element (231) remains coupled to the second anchor oligonucleotide. The released detection reagent hook element and/or the detectably labeled displacer reagent can then be further processed and/or analyzed to identify the detection reagent and hence quantify the analyte.

Accordingly, in provided are methods for detecting and quantifying analyte in a sample, the method comprising: (a) contacting the sample with a complex comprising: (i) a support; (ii) a capture reagent attached to the support; (iii) a detection reagent attached to the support, wherein the capture reagent and detection reagents are configured to simultaneously bind to the analyte; (b) decoupling the detection reagent from the support, (c) decoupling the capture reagent from the support, and (d) detecting the detection reagent in solution. Further provided are colocalization-by-linkage assay compositions comprising: (a) a detection complex comprising (i) a support, (ii) a capture reagent and a detection reagent configured to bind simultaneously to the analyte; and (b) detectably-labeled binders and/or hook oligos are released from the support at the end of the CLA assay.

In some embodiments, released products off the surface are then detected using various post-release methods. In some embodiments, detectably-labeled hook oligos are detected using qPCR or other DNA read-out approaches such as next-gen sequencing.

Also provided herein are methods of processing an analyte for the detection the analyte, comprising: (a) contacting a sample comprising the analyte with a complex comprising: (i) a support, (ii) a capture reagent coupled to the support, and (iii) a detection reagent coupled to the support, thereby generating an analyte bound complex comprising the analyte coupled to the capture reagent and the detection reagent; (b) decoupling the detection reagent from the support; and (c) decoupling the capture reagent from the support; the detection reagent comprises a detectable element. Provided are also methods of processing an analyte for the detection the analyte, comprising: (a) providing an analyte couple to a detection reagent and a capture reagent, wherein the capture reagent is coupled to a support, and the detection reagent is coupled to the support; (b) decoupling the detection reagent from the support; and (c) decoupling the capture reagent from the support; wherein the detection reagent comprises a detectable element.

In some embodiments, provided is a method as in any one of the preceding embodiments, wherein the detectable element is a nucleic acid sequence configured to be detected by a sequencing reaction, a nucleic acid amplification reaction, or couple to a labeled probe. In some embodiments, provided is a method as in any one of the preceding embodiments, wherein the method further comprises (d) detecting the detection reagent.

Also provided are methods of detecting and/or quantifying an analyte in a sample, the method comprising: (a) contacting the sample with a complex comprising: (i) a support, (ii) a capture reagent releasably coupled to the support, (iii) a detection reagent releasably coupled to the support, wherein the capture reagent and detection reagents are configured to simultaneously bind to the analyte; (b) decoupling the detection reagent from the support; (c) decoupling the capture reagent from the support; and (d) detecting one or both of the released detection reagent or capture reagent. Further provided are methods for detecting and/or quantifying an analyte in a sample, the method comprising: (a) contacting the sample with a complex comprising: (i) a support; (ii) a capture reagent attached to the support; (iii) a detection reagent attached to the support, wherein the capture reagent and detection reagents are configured to simultaneously bind to the analyte; (b) decoupling the detection reagent from the support; and (c) decoupling the capture reagent from the support, wherein in either (b), (c), or both (b) and (c), comprises using a displacer reagent to decouple the detection reagent from the support, the capture reagent from the support, or both. In some embodiments, the method further comprises detecting the detectable reagent.

In some embodiments, provided is a method as in any one of the preceding embodiments, wherein the decoupled complex comprising the detection reagent, capture reagent, and analyte are captured on a second support. For example, provided are methods for detecting and/or quantifying analyte in a sample, the method comprising: (a) contacting the sample with a complex comprising: (i) a support; (ii) a capture reagent attached to the support; (iii) a detection reagent attached to the support, wherein the capture reagent and detection reagents are configured to simultaneously bind to the analyte; (b) decoupling the detection reagent from the support, (c) decoupling the capture reagent from the support;

(d) capturing the released detection reagent on a second support; and (e) detecting the capture reagent on the second support.

Further provided are colocalization-by-linkage assay composition for analysis of an analyte in a sample, the colocalization-by-linkage assay composition comprising: (a) a detection complex comprising (i) a support, (ii) a capture reagent releasably complexed with the support, and (iii) a detection reagent releasably complexed with the support via an anchoring element; and (b) a displacer reagent configured to displace the detection reagent from the anchoring element.

Figure 3:
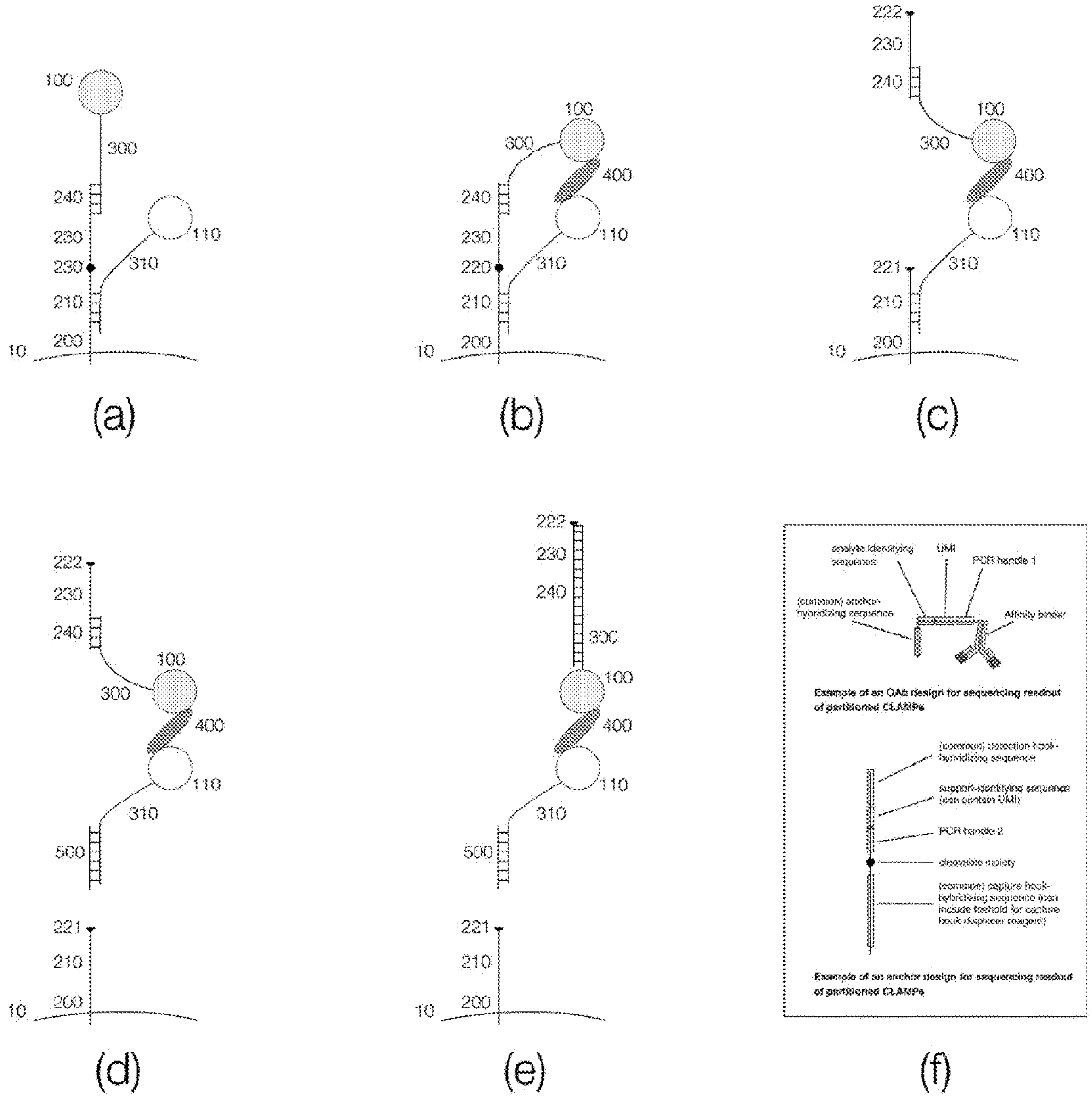
FIG. 3(*a*)-3(*f*) show a schematic of one embodiment of a 1-plex deterministic addCLAMP, wherein a cleaving agent is used to displace the detection reagent from the support and a displacing reagent is used to displace the capture reagent from the support. An example of the generation of an extended DNA oligonucleotide comprising elements from the support-specific anchor element and the detection reagent is shown.

Exemplifying the compositions and methods described herein, FIG. 3 demonstrates an analyte-dependent displacement colocalization-by-linkage on microparticles (add-CLAMP) assay composition. As shown in FIG. 3*a*, a microparticle support (10) comprises (1) a detection reagent (100), and (2) a capture reagent (110). Each of the detection and capture reagents comprise a hook oligonucleotide (300, 310 respectively). In this embodiment, the anchor oligonucleotide consists of multiple sequences (240, 230, 210, 200), contains a cleavable linker element (220), and is attached to the support. In this embodiment, the detection reagent hook oligonucleotide (300) is hybridized to a portion of the anchor oligonucleotide (240). In this embodiment, the capture reagent hook oligonucleotide (310) is hybridized to a portion of the anchor oligonucleotide (210). The detection and capture reagents are specific for an analyte and are configured to be capable of binding said analyte. After incubation with a sample comprising a plurality of analytes (FIG. 3*b*), a complex between an analyte (400) and the detection and capture reagents is generated. A cleaving agent specific for the cleavable linker element (220) cleaves the anchor oligonucleotide. Some elements of the cleaved cleavable linker element (222) and anchor oligonucleotide (230, 240) remain coupled to the capture reagent hook element, and some elements of the cleaved cleavable linker element (221) and anchor oligonucleotide (221, 210) remains coupled to the support. Cleaving the cleavable linker element in the anchor oligonucleotide thereby displaces the detection reagent from a cleaved portion of the anchor oligonucleotide (FIG. 3*c*). Any displaced detection reagent that is not coupled to the support via the detection complex is removed. A displacer reagent (500) is provided (FIG. 3*d*), and the detectably labeled displacer reagent specifically binds to the capture reagent hook element, displacing the capture reagent from the anchor oligonucleotide. The released detection reagent hook element and/or the detectably labeled displacer reagent can then be further processed and/or analyzed to identify the detection reagent and hence quantify the analyte. In one embodiment shown here (FIG. 3*e*, 3*f*), the released detection reagent hook element is an oligonucleotide that is extended so as to include the complementary sequences that are present on the anchor oligonucleotide elements, thereby ensuring that analyte-specific information from a CLAMP can be linked to the capture support that was used to introduce the CLAMP to the sample.

Figure 4:
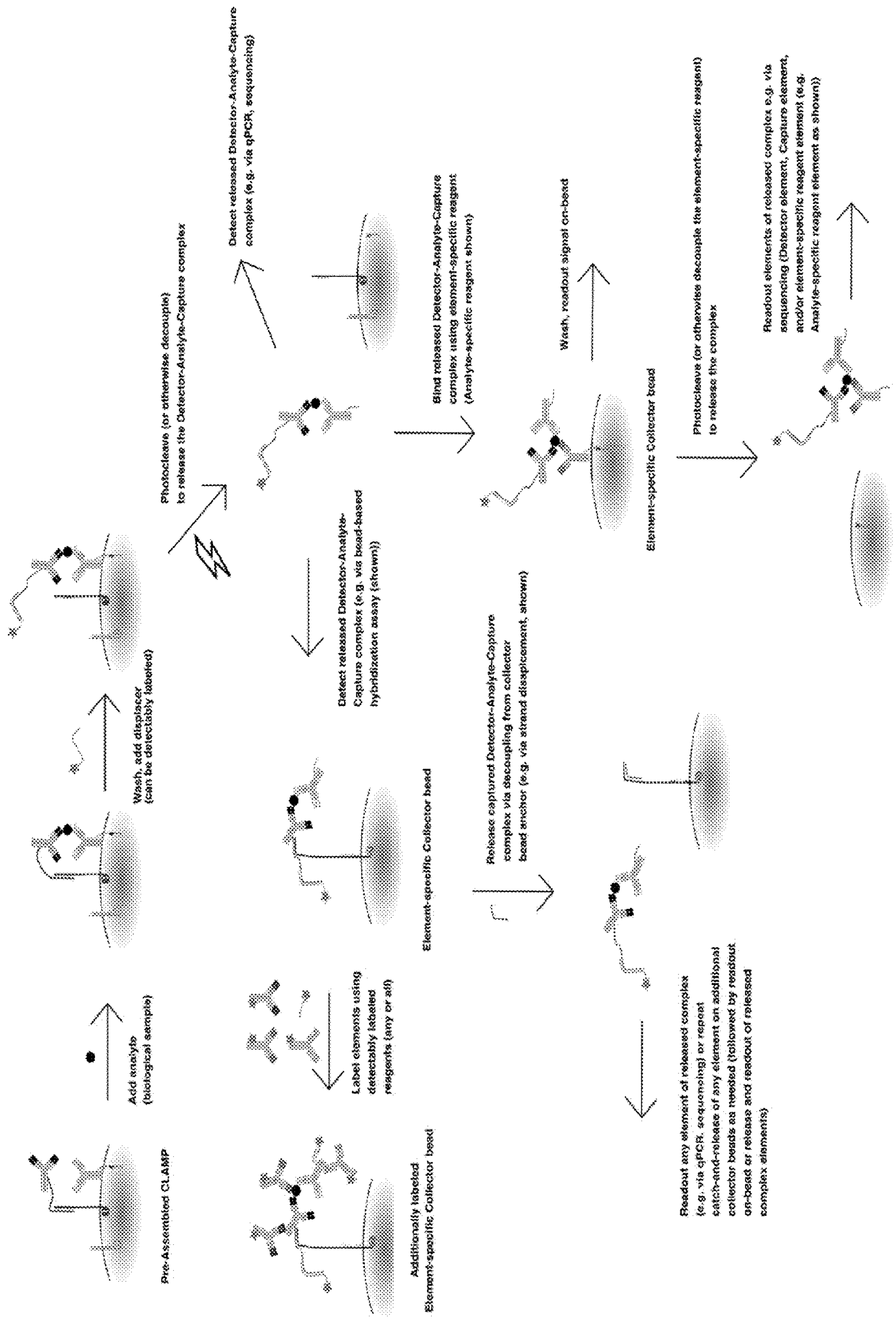
FIG. 4 shows a multistep workflow for one embodiment of a 1-plex stochastic addCLAMP, wherein a displacer reagent is used to displace the detection reagent from the support and a cleaving agent is used to displace the capture reagent from the support. Multiple release and capture steps, collector beads, and various readout methods are illustrated.

Exemplifying the compositions and methods described herein, FIG. 4 demonstrates an analyte-dependent displacement colocalization-by-linkage on microparticles (add-CLAMP) assay composition. An assembled CLAMP complex, consisting of a barcoded microparticle, upon which is stochastically assembled (1) a detection reagent consisting of a detection antibody conjugated to a hook oligonucleotide, which is hybridized to an anchor oligonucleotide that is attached to the support, and (2) a capture reagent consisting of a capture antibody conjugated to the support using a photo cleavable anchor element. The detection antibody and capture antibody are specific for the same analyte and are configured to be capable of binding said analyte to form a sandwich complex. After the support containing the CLA complex is added to a sample comprising a plurality of analytes, a complex between an analyte and the detection antibody and the capture antibody is generated. After (optionally) removing the complexed support from the bulk of the sample by washing, an (optionally) labelled displacer reagent, consisting of a Cy5-labeled displacer oligonucleotide in this example, is added. The Cy5-labeled displacer oligonucleotide is complementary to a toe-hold sequence on the detection antibody hook oligonucleotide, as well as the portion of the hook oligonucleotide that is hybridized to the anchor oligonucleotide, and hence displaces the hook oligonucleotide from the anchor oligonucleotide. Any displaced detection antibodies and/or hook oligonucleotides that are not coupled to the support via the detection complex can be removed via washing. Next, a UV light source is used to photo-cleave the photo-cleavable anchor element, thereby releasing the capture antibody from the support, and in doing so releasing the sandwich complex from the support. The released sandwich complex, consisting of a detection antibody, detection antibody hook element, labeled displacer oligonucleotide, analyte, capture antibody, and the photo-cleaved capture antibody anchor element, can then be further processed and/or analyzed to identify the detection reagent and/or displacer reagent and/or detection antibody hook oligonucleotide, and hence quantify the analyte using a variety of techniques, including via PCR, qPCR, next-generation DNA sequencing, molecular tweezers, a nanostring/ncounter assay, and/or DNA hybridization assays. The released sandwich complex can also be detected using a range of collector bead assays. In some embodiments, the released sandwich complex is bound using a third analyte-specific antibody that is releasably attached to a collector bead. In some embodiments, after an optional wash, the Cy5-labeled displacer oligonucleotide in this example can then be detected on the collector bead. In some embodiments, after a wash, the third analyte-specific antibody is decoupled from the collector bead support, for example using UV light. The re-released sandwich complex can then be further processed and/or analyzed to identify the detection reagent and/or displacer reagent and/or detection antibody hook oligonucleotide, the analyte, the capture reagent and/or cleaved capture antibody anchor element, and hence quantify the analyte using a variety of techniques, including via PCR, qPCR, next-generation DNA sequencing, molecular tweezers, a nanostring/ncounter assay, and/or DNA hybridization assays.

In some embodiments, the released sandwich complex is bound using a detection antibody hook oligonucleotide-complementary DNA oligonucleotide attached to a collector bead. The captured sandwich complex can be read on-bead following an optional wash. The captured sandwich complex can also be further labeled using labeling elements that are specific for any element of the captured sandwich complex, which includes e.g. fluorescently-labeled antibodies against the detection antibody and/or capture antibody and/or analyte, or a fluorescently-labeled DNA probe complementary to a portion of the detection antibody hook element.

In some embodiments, after a released sandwich complex has been bound using a detection antibody hook oligonucleotide-complementary DNA oligonucleotide attached to a collector bead, the sandwich complex is re-released using a displacer oligonucleotide complementary to the DNA oligonucleotide attached to a collector bead. The re-released sandwich complex can then be further processed and/or analyzed to identify the detection reagent and/or displacer reagent and/or detection antibody hook oligonucleotide, the analyte, the capture reagent and/or cleaved capture antibody anchor element, and hence quantify the analyte using a variety of techniques, including via PCR, qPCR, next-generation DNA sequencing, molecular tweezers, a nanostring/ncounter assay, and/or DNA hybridization assays. The catch-and-release steps describe here can be repeated multiple times to continue introducing complex-specific binding reagents into the final sandwich complex that is read out.

Figure 5:
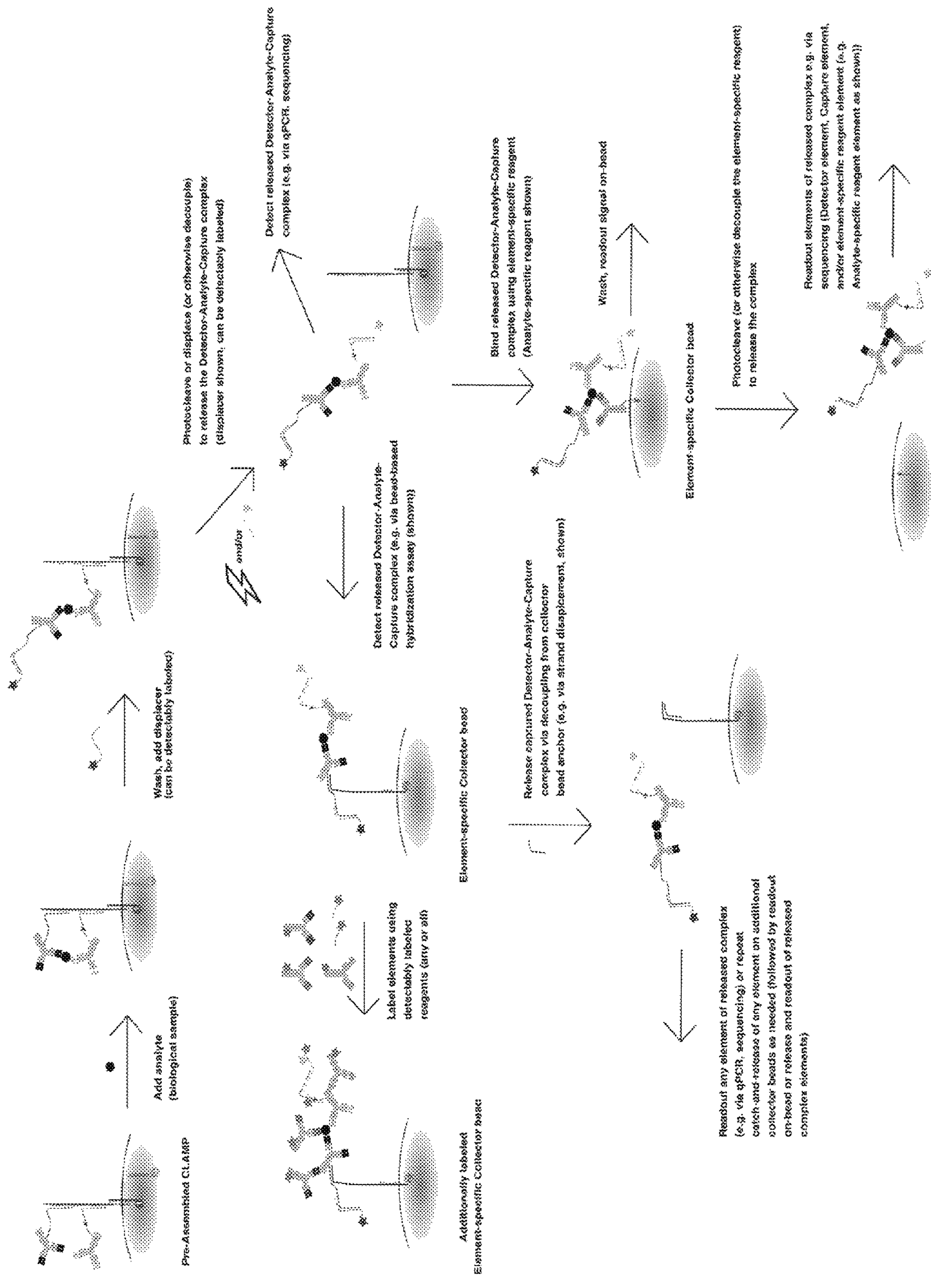
FIG. 5 shows a multistep workflow for one embodiment of a 1-plex deterministic addCLAMP, wherein a displacer reagent is used to displace the detection reagent from the support and a cleaving agent is used to displace the capture reagent from the support. Multiple release and capture steps, collector beads, and various readout methods are illustrated.

Exemplifying the compositions and methods described herein, FIG. 5 demonstrates an analyte-dependent displacement colocalization-by-linkage on microparticles (add-CLAMP) assay composition and workflow for detecting an analyte in a sample. An assembled CLAMP complex, consisting of a barcoded microparticle, upon which is deterministically assembled (1) a detection reagent consisting of a detection antibody conjugated to a detection hook oligonucleotide, which is hybridized to an anchor oligonucleotide that is attached to the support, and (2) a capture reagent consisting of a capture antibody conjugated to a capture hook oligonucleotide with is hybridized to the same anchor oligonucleotide. The detection antibody and capture antibody are specific for the same analyte and are configured to be capable of binding said analyte to form a sandwich complex. After the support containing the CLA complex is added to a sample comprising a plurality of analytes, a complex between an analyte and the detection antibody and the capture antibody is generated. After (optionally) removing the complexed support from the bulk of the sample by washing, a first (optionally) labelled displacer reagent, consisting of a Cy5-labeled first displacer oligonucleotide in this example, is added. The Cy5-labeled first displacer oligonucleotide is complementary to a toe-hold sequence on the detection antibody hook oligonucleotide, as well as the portion of the detection antibody hook oligonucleotide that is hybridized to the anchor oligonucleotide, and hence displaces the detection antibody hook oligonucleotide from the anchor oligonucleotide. Any displaced detection antibodies and/or detection antibody hook oligonucleotides that are not coupled to the support via the detection complex can be removed via washing. Next, an (optionally) second labelled displacer reagent, consisting of a Cy3-labeled second displacer oligonucleotide in this example, is added. The second labeled displacer oligonucleotide is complementary to a toe-hold sequence on the capture antibody hook oligonucleotide, as well as the portion of the capture antibody hook oligonucleotide that is hybridized to the anchor oligonucleotide, and hence displaces the capture antibody hook oligonucleotide from the anchor oligonucleotide, thereby releasing the capture antibody from the support, and in doing so releasing the sandwich complex from the support. The released sandwich complex, consisting of a detection antibody, detection antibody hook element, labeled first displacer oligonucleotide, analyte, capture antibody, capture antibody hook element, and labeled second displacer oligonucleotide, can then be further processed and/or analyzed to identify the detection reagent and/or first displacer reagent and/or detection antibody hook oligonucleotide, and hence quantify the analyte using a variety of techniques, including via PCR, qPCR, next-generation DNA sequencing, molecular tweezers, a nanostring/ncounter assay, and/or DNA hybridization assays.

The released sandwich complex can also be detected using a range of collector bead assays. In some embodiments, the released sandwich complex is bound using a third analyte-specific antibody that is releasably attached to a collector bead. In some embodiments, after an optional wash, the Cy5-labeled first displacer oligonucleotide in this example can then be detected on the collector bead, and/or the Cy3-labeled second displacer oligonucleotide in this example can then be detected on the collector bead. In some embodiments, after a wash, the third analyte-specific antibody is decoupled from the collector bead support, for example using UV light. The re-released sandwich complex can then be further processed and/or analyzed to identify the detection reagent and/or first displacer reagent and/or detection antibody hook oligonucleotide, the analyte, the capture reagent, the second displacer reagent and/or capture antibody hook oligonucleotide, and hence quantify the analyte using a variety of techniques, including via PCR, qPCR, next-generation DNA sequencing, molecular tweezers, a nanostring/ncounter assay, and/or DNA hybridization assays.

In some embodiments, the released sandwich complex is bound using a detection antibody hook oligonucleotide-complementary DNA oligonucleotide attached to a collector bead. The captured sandwich complex can be read on-bead following an optional wash. The captured sandwich complex can also be further labeled using labeling elements that are specific for any element of the captured sandwich complex, which includes e.g. fluorescently-labeled antibodies against the detection antibody and/or capture antibody and/or analyte, or a fluorescently-labeled DNA probe complementary to a portion of the detection antibody hook element and/or capture antibody hook element and/or first displacer reagent and/or second displacer reagent.

In some embodiments, after a released sandwich complex has been bound using a detection antibody hook oligonucleotide-complementary DNA oligonucleotide attached to a collector bead, the sandwich complex is re-released using a displacer oligonucleotide complementary to the DNA oligonucleotide attached to a collector bead. The re-released sandwich complex can then be further processed and/or analyzed to identify the detection reagent and/or first displacer reagent and/or detection antibody hook oligonucleotide, the analyte, the capture reagent, the second displacer reagent and/or capture antibody hook oligonucleotide, and hence quantify the analyte using a variety of techniques, including via PCR, qPCR, next-generation DNA sequencing, molecular tweezers, a nanostring/ncounter assay, and/or DNA hybridization assays. The catch-and-release steps describe here can be repeated multiple times to continue introducing complex-specific binding reagents into the final sandwich complex that is read out.

In some embodiments, provided is a method as in any one of the preceding embodiments, wherein the support further comprises a first anchor element and second anchor element coupled thereto, and wherein the capture reagent is releasably coupled to the support via the first anchor element and the detection reagent is releasably coupled to the support via the second anchor element.

In some embodiments, provided is a method as in any one of the preceding embodiments, wherein first anchor element comprises a first anchor oligonucleotide and the second anchor element comprise a second anchor oligonucleotide.

In some embodiments, provided is a method as in any one of the preceding embodiments, wherein the capture reagent comprises a first hook element coupled thereto, and wherein the first hook element is releasably coupled to the first anchor element.

In some embodiments, provided is a method as in any one of the preceding embodiments, wherein the detection reagent comprises a second hook element coupled thereto, and wherein the second hook element is releasably coupled to the second anchor element.

In some embodiments, provided is a method as in any one of the preceding embodiments, wherein (i) the capture reagent comprises a first hook element coupled thereto, and wherein the first hook element is releasably coupled to the first anchor element, and (ii) the detection reagent comprises a second hook element coupled thereto, and wherein the second hook element is releasably coupled to the second anchor element.

In some embodiments, provided is a method as in any one of the preceding embodiments, wherein the support further comprises an anchor element coupled thereto, and wherein the capture reagent is releasably coupled to the support via the anchor element and the detection reagent is releasably coupled to the support via the anchor element.

In some embodiments, provided is a method as in any one of the preceding embodiments, wherein (i) the capture reagent comprises a first hook element coupled thereto, and wherein the first hook element is releasably coupled to the anchor element, and (ii) the detection reagent comprises a second hook element coupled thereto, and wherein the second hook element is releasably coupled to the anchor element.

In some embodiments, provided is a method as in any one of the preceding embodiments, wherein the first hook element comprises a first hook oligonucleotide and the second hook element comprises a second hook oligonucleotide.

In some embodiments, provided is a method as in any one of the preceding embodiments, wherein one or both of the first hook oligonucleotide and the second hook oligonucleotide comprise a barcode sequence, unique molecular identifier sequence, a primer binding sequence, or a combination thereof.

In some embodiments, provided is a method as in any one of the preceding embodiments, wherein the method further comprises (e) detecting at least one of the capture reagent and the detection reagent.

In some embodiments, provided is a method as in any one of the preceding embodiments, wherein (e), detecting comprises identifying a nucleic acid molecule corresponding to the detection reagent.

In some embodiments, provided is a method as in any one of the preceding embodiments, wherein identifying the nucleic acid molecule comprises performing a sequencing reaction, a PCR, a qPCR, or nucleic acid probe-based assay. In some embodiments, provided is a method as in any one of the preceding embodiments, wherein the nucleic acid molecule comprises a barcode sequence, unique molecular identifier sequence, a primer binding sequence, or a combination thereof.

In some embodiments, provided is a method as in any one of the preceding embodiments, wherein (b), decoupling comprises providing a detectable displacer agent that decouples the detection reagent from the support. In some embodiments, provided is a method as in any one of the preceding embodiments, wherein the detectable displacer agent is an oligonucleotide. In some embodiments, provided is a method as in any one of the preceding embodiments, wherein the oligonucleotide comprises a barcode sequence, unique molecular identifier sequence, a primer binding sequence, or a combination thereof. In some embodiments, provided is a method as in any one of the preceding embodiments, wherein (c), decoupling comprises providing a displacer agent or applying a stimulus that decouples the capture reagent from the support. In some embodiments, provided is a method as in any one of the preceding embodiments, wherein the displacer agent is an oligonucleotide. In some embodiments, provided is a method as in any one of the preceding embodiments, wherein the oligonucleotide comprises a barcode sequence, unique molecular identifier sequence, a primer binding sequence, or a combination thereof. In some embodiments, provided is a method as in any one of the preceding embodiments, wherein subsequent to (d), the method comprises capturing the detection reagent and/or the capture reagent on a second support. In some embodiments, provided is a method as in any one of the preceding embodiments, wherein the method comprises a washing step after any of the steps provided.

In some embodiments, provided is a method as in any one of the preceding embodiments, wherein the capture reagent is an antibody, an antibody fragment, an aptamer, a modified aptamer, a somamer, an affimer, an antigen, a protein, a polypeptide, a multi-protein complex, an exosome, an oligonucleotide, or a low molecular weight compound. In some embodiments, provided is a method as in any one of the preceding embodiments, wherein the detection reagent is an antibody, an antibody fragment, an aptamer, a modified aptamer, a somamer, an affimer, an antigen, a protein, a polypeptide, a multi-protein complex, an exosome, an oligonucleotide, or a low molecular weight compound.

In some embodiments, provided is a method as in any one of the preceding embodiments, wherein the analyte is an antigen, an antibody, an affimer, an aptamer, a modified aptamer, a somamer, an antibody fragment, a protein, a polypeptide, a multi-protein complex, an exosome, an oligonucleotide, a hormone, a modified oligonucleotide, or a low molecular weight compound. In some embodiments, provided is a method as in any one of the preceding embodiments, wherein the sample is a biological sample, as described herein.

In some embodiments, provided is a method as in any one of the preceding embodiments, wherein the sample is a bodily fluid, an extract, a solution containing proteins and/or DNA, a cell extract, a cell lysate, a single cell lysate, or a tissue lysate. In some embodiments, the sample is present within a partition (e.g. a well, a tube, a droplet, etc.) In some embodiments, the sample is a bodily fluid comprising an extract, a solution containing proteins and/or DNA, a cell extract, a cell lysate, or a tissue lysate.

Posterior CLA Compositions and Methods

The same CLA principle can be applied for the measurement of antibodies when the binders used are identical antigens specific to the antibody to be determined. Since the detection proceeds through RDT (release-dependent transduction), as opposed to species-specific anti-Ig antibodies, the assay does not suffer from a detectable non-specific signal. Additionally, CLA and CLAMP additionally enable multiplexed measurement of antibodies while maintaining sensitivity and specificity of a single-plex assay.

On the other hand, the methods and systems utilizing CLA principle for antibody measurement are not favorable to concurrent detection or classification of antibody class or iso-type. The detection of antibody iso-type necessitates the use of anti-species antibodies (eg. Anti human-IgG or anti human-IgA) but the pre-assembly of such anti-species antibodies on the support, as per CLA, would result in spurious capture of off-target antibodies and yield a severely reduced signal (false negative).

In certain instances, shortcoming of CLA and CLAMP can be understood even more broadly when considering that the iso-type classification is challenging in multiplex due to the requirement of a "common epitope" recognition. That is to say, this becomes a challenge whenever the detection or measurement of an analyte requires, at least partially, the recognition of an epitope that is common to many analytes in a sample (eg. Species- and iso-type specific Fc region or a post-translational modification on a protein such as phosphorylation). In those cases, the pre-assembly of common-epitope binder to a support before incubation with the sample, as in CLA, will result in spurious binding, and "false negative" detection.

The co-localization of sandwich binders to the support before sample incubation is advantageous for multiplexing, as demonstrated by the CLA assays. In a preferred embodiment, the signalling binders against different targets are pre-assembled on different barcoded microparticles, which avoids their mixing and interaction and avoids assay cross-reactivity. However, the application of the methods and systems described in U.S. Pre-Grant Publication No. US20200319173, wherein both binders are pre-assembled on the support before a sample is introduced, is not advantageous for isotype-specific detection of antibodies. The requirement of an isotype-specific reagents, such as an anti-IgG antibody, and their pre-assembly on the surface means that non-antigen specific IgG antibodies in the sample will bind to the support and interfere with the assay, significantly reducing its performance. More broadly, this is a challenge for any analyte being recognized by at least one binder via a common epitope, wherein the epitope is shared by many other proteins or analytes in the biological sample; for example, a phospho-protein sandwich assay wherein the detection binder (e.g. detection reagent) is directed at the phosphorylated portion of the protein.

Different methods for identifying and quantifying antibodies are described in the prior art. The detection of a certain class of antigen-specific antibodies in a sample is often performed by binding specific antibodies to a solid phase coated with the specific antigen. The immunoglobulins (Ig), which are specific for the antigen and are now bound to the solid phase, are detected by the binding of antibodies, which are specifically directed against human Ig of a certain class, to the Ig molecules to be detected. The antibodies directed against human Ig are provided with a label by means of which the detection takes place. However, such a test procedure (indirect test format) is only possible if, before the reaction with the class-specific labelled antibodies directed against human Ig, all unspecific, non-bound Ig is removed by washing.

Furthermore, washing is rarely efficient, and in certain cases is especially problematic, resulting in high background signals. It is a disadvantage of this process that falsely positive values are obtained due to nonspecific binding of non-specific antibodies contained in the sample. A further test for the detection and for the quantitative determination of an antibody consists in that antigens against the antibodies to be determined are fixed on a solid phase. Subsequently, there is added thereto a patient's serum, together with a predetermined amount of the antibody to be determined but which carries a label and subsequently the label bound to the solid phase is measured. It is thus a competitive test, the sensitivity of which leaves something to be desired. A further possibility is to bind an anti-Ig antibody to a solid phase and then to react it with the test solution. Subsequently, there is added an antigen specific for the antibodies to be determined, which antigen carries a label. A disadvantage of this method is the limited binding capacity of the solid phase since, apart from the antibody to be determined, other antibodies of the same globulin class are also bound.

The so-called bridge test opens up a possibility for carrying out an antibody detection and overcome the detectably-high non-specific binding problem of the indirect test format. In this method, a first binding partner, which is capable of specific binding to the antibody to be determined such as, for example, an antigen, is bound to a solid phase. The antibody to be determined binds to the solid phase-bound antigen. A second specific antigen, which is provided with a label, is also present in the test mixture. The antibody is detected by means of the label attached to the second specific antigen. The bridge test avoids the detectable non-specific signal because detection occurs via specific binding to the antibody paratope, as opposed to the Fc region. However, by avoiding this problem the bridge test is unable to classify the antibody class: if immunoglobulins of different classes but of the same specificity are present in the sample, the test does not distinguish between them.

In both cases, the methods are directed against all Ig specific to one antigen. They are not amenable to isotype-specific detection, and indeed distinguishing and quantifying different classes. Even more importantly, due to the use of a labeled antigen, both methods are not amenable to multiplexing, or the detection of multiple antibodies against multiple antigens. There thus lacks a for the multiplexed and iso-type detection of antibodies, that is, the ability to detect and measure antibodies against different targets while maintaining isotype classification.

Protein post-translational modifications (PTMs) increase the functional diversity of the proteome by the covalent addition of functional groups or proteins, proteolytic cleavage of regulatory subunits, or degradation of entire proteins. These modifications include phosphorylation, glycosylation, ubiquitination, nitrosylation, methylation, acetylation, lipidation and proteolysis and influence almost all aspects of normal cell biology and pathogenesis. Therefore, identifying and understanding PTMs is critical in the study of cell biology and disease treatment and prevention.

Mass spectrometry is arguably the most robust technology capable of direct PTM measurement for many proteins simultaneously. It has provided transformative insight into the roles phosphorylation, acetylation, ubiquitylation have on cell biology. However, mass spectrometry remains too slow and expensive to measure PTM at high-throughput and large scale, and is particularly not amenable to broad deployment in clinical pipelines.

The posterior-CLAMP compositions and methods described herein, ins come instances, resolve the challenges associated with the detection of common or substantially similar epitopes. The methods and compositions described herein are based, at least in part, on the design and construction of linkages between reagents and supports, wherein the linkages enable addressable and programmable topology and function. In certain instances, the compositions and methods provided herein can reduce or eliminate one or more sources of background noise in multiplexed protein assays, and enable the measurement of historically challenging targets with common epitopes.

In some embodiments, the methods and systems provided herein enables the multiplexed measurement of target- and iso-type specific antibodies. In other embodiments, the methods and systems provided herein enables the multiplexed measurement of post-translationally modified proteins using minimal reagents. More generally, the present disclosure provides methods for detecting and quantitating multiple protein analytes that include common epitopes which typically result in assay cross-reactivity.

In the present disclosure, a first analyte-specific binder is releasably linked to the support, wherein this first binder binds to the analyte at an epitope that is unique to the protein. A second binder is provided that is directed against the same analyte. Furthermore, the second binder can be linked to the same support using a linker. Importantly, the second binder is only added after the sample is incubated with the support and washed. If the analyte was in the sample and bound to the first binder, then at least some of second binders will simultaneously link to the support and bind to the analyte, forming a bridge. To detect the presence of the analyte, the first binder is displaced from the support as well as detectably-labeled.

A first general class of embodiments provides a method for detecting an analyte of interest using posterior co-localization by linkage assays (pCLA). The methods include (1) mixing an analyte-containing sample with a support containing a first analyte-specific binder that is conjugated to a first linker oligonucleotide that is releasably attached to the support via a first anchor oligonucleotide, wherein the support also includes a second anchor oligonucleotide; (2) the addition of a second binder specific to the analyte, conjugated to a second linker oligonucleotide. The second linker oligo hybridizes to the second anchor oligo linked on to the same support, thereby securely linking the second binder to the support. If the analyte is present in the sample and has been captured by the first binder, then at least some of the second binders will bind to the other epitope on the analyte; and (3) the addition of a labeled displacer oligo that hybridizes preferentially to the first linker oligo, displacing it from the first anchor oligo. The first hook oligo, now labeled with a dye, will thus only remain on the surface if the analyte is bound to both binders and if the displacement was successful.

As noted above, when the analyte of interest includes a common epitope (eg. Fc region of a human IgG) which must to be recognized for accurately classifying the analyte, the second binder is then used to target said common epitope whereas the first binder is used to target the more specific epitope (eg. paratope of an IgG). In that way, the first step is used to capture the analyte specifically followed by washing non-specific analytes that can contain the common epitope (eg. non-specific IgG molecules).

Importantly, the present disclosure overcomes the non-specific binding background signal issue. As those skilled in the art will appreciate, non-specific adsorption of molecules containing such common epitopes (e.g. non-specific IgG molecules) often results in high background signals in assays that rely on these common epitopes for detection, as in indirect ELISAs that label antibodies using secondary antibodies. In the present disclosure, detection proceeds using CLA's RDT (release-dependent transduction) which relies simply on labeling the first hook oligo.

Furthermore, the methods in the present disclosure can be multiplexed to enable the detection of a multiplicity of analytes. In one embodiment, the methods in the present disclosure enable the detection and quantitation of antibodies detecting multiple targets and having a multiplicity of isotypes.

Accordingly provided herein are compositions for detecting and/or quantifying an analyte using a composition comprising: (i) a support, (ii) a capture reagent attached to a first oligo, wherein the first oligo is hybridized to a second oligo, wherein the second oligo is attached to the support, (iii) a third oligo attached to the support; a detection reagent attached to a fourth oligo, wherein the fourth oligo is complementary to the third oligo; and a detectable displacer reagent, wherein the detectable displacer reagent is configured to hybridize to the first oligo, and displace it from the second oligo and the support. For example, also provided herein are methods for detecting and/or quantifying an analyte using a composition comprising: delivering a sample to a support comprising (i) a capture reagent attached to a first oligo, wherein the first oligo is hybridized to a second oligo, wherein the second oligo is attached to the support, (iii) a third oligo attached to the support; providing a detection reagent attached to a fourth oligo and contacting it with the support, wherein the fourth oligo is complementary to the third oligo, thereby tethering the detection reagent to the support; and providing a detectable displacer reagent and contacting it with the support, wherein the detectable displacer reagent is configured to hybridize to the first oligo, and displace it from the second oligo and the support; and detecting the presence of the detectable displacer agent.

Also provided are methods for detecting and quantifying an analyte within a sample, comprising: (a) contacting the sample with a colocalization by linkage assay (CLA) complex comprising: (i) a support; (ii) a first anchor element attached to the support; (iii) a second anchor element attached to the support; (iv) a capture agent reversibly coupled with the first anchor element, wherein the capture agent is configured to bind the analyte; (b) providing a detection agent configured to bind the analyte and couple with the second anchor element; (c) providing a detectable displacer agent configured to couple with the capture agent and release the capture agent from the first anchor element; and (d) detecting a presence or absence of the detectable displacer agent; thereby indicating the presence or absence of the analyte. Further provided are methods for detecting an antibody in a sample, comprising: (a) contacting the sample with a colocalization by linkage assay (CLA) complex comprising: (i) a support; (ii) a first anchor element attached to the support; (iii) a second anchor element attached to the support; (iv) an antigen, wherein the antigen is releasably coupled to the first anchor element; (b) providing an isotype-specific binding agent, wherein the isotype-specific binding agent is configured to bind an isotype of the antibody and couple to the second anchor element; (c) providing a detectable displacer agent configured to couple to the antigen and release the antigen from the first anchor element; and (d) detecting a presence or absence of the detectable displacer agent; thereby indicating (1) the presence or absence of the antibody bound to the antigen, and (2) the isotype of the antibody. Provided are methods for characterizing an analyte in a sample, comprising: (a) contacting the sample with a colocalization by linkage assay (CLA) complex comprising: (i) a support; (ii) a first anchor element attached to the support; (iii) a second anchor element attached to the support; (iv) a capture agent releasably coupled to the first anchor element, wherein the capture agent is configured to bind the analyte; (b) providing a detection agent, wherein the detection agent binds a post-translational modification of the analyte and couple to the second anchor element; (c) providing a detectable displacer agent configured to couple to the capture agent and release the capture agent from the first anchor element; and (d) detecting a presence or absence of the detectable displacer agent; thereby indicating (1) the presence or absence of the analyte, and (2) the post-translational modification.

Also provided are methods for detecting and/or characterizing an analyte in a sample, comprising: (a) contacting the sample with a colocalization by linkage assay (CLA) complex comprising: (i) a support; (ii) a first anchor element attached to the support; (iii) a second anchor element attached to the support; (iv) a capture agent releasably coupled to the first anchor element, wherein the capture agent is configured to bind the analyte; (b) providing a detection agent, wherein the detection agent binds a post-translational modification of the analyte and couples to the second anchor element; (c) providing a detectable displacer agent configured to couple to the detection agent and release the detection agent from the second anchor element; and (d) detecting a presence or absence of the detectable displacer agent; thereby indicating (1) the presence or absence of the analyte, and (2) the post-translational modification.

Also provided are methods of detecting and/or quantifying an analyte in a sample, the method comprising: (a) contacting the sample with a complex comprising: (i) a support, and (ii) a capture reagent releasably coupled to the support; (b) providing a detection reagent, wherein the capture reagent and detection reagent are configured to simultaneously bind to the analyte; (b) decoupling the detection reagent from the support; (c) decoupling the capture reagent from the support; and (d) detecting one or both of the released detection reagent or capture reagent.

Further provided are methods of processing an analyte for the detection and quantification of the analyte, the method comprising: (a) contacting a sample comprising the analyte with a complex comprising: (i) a support, and (ii) a capture reagent attached to the support, thereby generating the analyte coupled to the capture reagent; (b) contacting the analyte bound complex with a detection reagent configured to couple to the analyte and couple to the support, thereby generating an analyte bound complex comprising the analyte coupled to the capture reagent and the detection reagent; and (c) decoupling at least one of the capture reagent and the detection reagent from the support, wherein the detection reagent is configured to be detected.

In some embodiments, provided is a method of any one of the preceding embodiments, wherein the detection reagent are configured to be detected (e.g. comprise a detectable element) by a sequencing reaction, a nucleic acid amplification reaction (e.g. PCR), or coupling to labeling agent (e.g. a displacer reagent). In some embodiments, provided is a method of any one of the preceding embodiments, wherein the method further comprises (d) detecting at least one of the capture reagent and the detection reagent. In some embodiments, provided is a method of any one of the preceding embodiments, wherein the support further comprises a first anchor element and second anchor element coupled thereto, and wherein the capture reagent is releasably coupled to the support via the first anchor element and the detection reagent is releasably coupled to the support via the second anchor element. In some embodiments, provided is a method of any one of the preceding embodiments, wherein the first anchor element comprises a first anchor oligonucleotide and the second anchor element comprise a second anchor oligonucleotide. In some embodiments, provided is a method of any one of the preceding embodiments, wherein the capture reagent comprises a first hook element coupled thereto, and wherein the first hook element is releasably coupled to the first anchor element.

In some embodiments, the detection reagent comprises a second hook element coupled thereto, and wherein the second hook element is configured to releasably couple to the second anchor element. In some embodiments, provided is a method of any one of the preceding embodiments, wherein (i) the capture reagent comprises a first hook element coupled thereto, and wherein the first hook element is releasably coupled to the first anchor element, and (ii) the detection reagent comprises a second hook element coupled thereto, and wherein the second hook element is configured to releasably couple to the second anchor element. In some embodiments, provided is a method of any one of the preceding embodiments, wherein the support further comprises an anchor element coupled thereto, and wherein the capture reagent is releasably coupled to the support via the anchor element is releasably coupled to the support via the anchor element and the detection reagent is configured to releasably couple to the support via the anchor element. In some embodiments, provided is a method of any one of the preceding embodiments, wherein (i) the capture reagent comprises a first hook element coupled thereto, and wherein the first hook element is releasably coupled to the anchor element, and (ii) the detection reagent comprises a second hook element coupled thereto, and wherein the second hook element is releasably coupled to the anchor element. In some embodiments, provided is a method of any one of the preceding embodiments, wherein the first hook element comprises a first hook oligonucleotide and the second hook element comprises a second hook oligonucleotide. In some embodiments, provided is a method of any one of the preceding embodiments, wherein one or both of the first hook oligonucleotide and the second hook oligonucleotide comprise a barcode sequence, unique molecular identifier sequence, a primer binding sequence, or a combination thereof.

In some embodiments, provided is a method of any one of the preceding embodiments, wherein (c), decoupling comprises providing a detectable displacer agent that decouples the detection reagent from the support. In some embodiments, provided is a method of any one of the preceding embodiments, wherein the detectable displacer agent is an oligonucleotide. In some embodiments, provided is a method of any one of the preceding embodiments, wherein the oligonucleotide comprises a barcode sequence, unique molecular identifier sequence, a primer binding sequence, or a combination thereof. In some embodiments, provided is a method of any one of the preceding embodiments, wherein (c), decoupling comprises providing a detectable displacer agent that decouples the capture reagent from the support. In some embodiments, provided is a method of any one of the preceding embodiments, wherein the detectable displacer agent is an oligonucleotide. In some embodiments, provided is a method of any one of the preceding embodiments, wherein the oligonucleotide comprises a barcode sequence, unique molecular identifier sequence, a primer binding sequence, or a combination thereof. In some embodiments, provided is a method of any one of the preceding embodiments, wherein (i) the analyte is an antibody molecule, (ii) the capture reagent is an antigen, and (iii) the detection reagent is specific for an immunoglobulin class IgG, IgM, IgA, IgD, or IgE. In some embodiments, provided is a method of any one of the preceding embodiments, wherein detection reagent comprises an anti-IgG, -IgM, -IgA, -IgD, or -IgE antibody. In some embodiments, provided is a method of any one of the preceding embodiments, wherein detection reagent comprises an protein A, protein G, or protein M. In some embodiments, provided is a method of any one of the preceding embodiments, wherein (i) the analyte is protein comprising posttranslational modification, (ii) the capture reagent binds the protein, and (iii) the detection reagent is specific for the posttranslational modification or the protein comprising the posttranslation modification.

In some embodiments, provided is a method as in any one of the preceding embodiments, wherein the method comprises a washing step after any of the steps provided.

In some embodiments, provided is a method as in any one of the preceding embodiments, wherein the capture reagent is an antibody, an antibody fragment, an aptamer, a modified aptamer, a somamer, an affimer, an antigen, a protein, a polypeptide, a multi-protein complex, an exosome, an oligonucleotide, or a low molecular weight compound. In some embodiments, provided is a method as in any one of the preceding embodiments, wherein the detection reagent is an antibody, an antibody fragment, an aptamer, a modified aptamer, a somamer, an affimer, an antigen, a protein, a polypeptide, a multi-protein complex, an exosome, an oligonucleotide, or a low molecular weight compound.

In some embodiments, provided is a method as in any one of the preceding embodiments, wherein the analyte is an antigen, an antibody, an affimer, an aptamer, a modified aptamer, a somamer, an antibody fragment, a protein, a polypeptide, a multi-protein complex, an exosome, an oligonucleotide, a hormone, a modified oligonucleotide, or a low molecular weight compound. In some embodiments, provided is a method as in any one of the preceding embodiments, wherein the sample is a biological sample, as described herein.

In some embodiments, provided is a method as in any one of the preceding embodiments, wherein the sample is a bodily fluid, an extract, a solution containing proteins and/or DNA, a cell extract, a cell lysate, a single cell lysate, or a tissue lysate. In some embodiments, the sample is present within a partition (e.g. a well, a tube, a droplet, etc.) In some embodiments, the sample is a bodily fluid comprising an extract, a solution containing proteins and/or DNA, a cell extract, a cell lysate, or a tissue lysate.

Provided herein are methods for detecting and quantifying an analyte within a sample, comprising: (a) contacting the sample with a colocalization by linkage assay (CLA) complex comprising: (i) a support; (ii) a first anchor element attached to the support; (iii) a second anchor element attached to the support; (iv) a capture agent releasable coupled reversibly coupled with the first anchor element, wherein the capture agent is configured to bind the analyte; (b) providing a detection agent configured to bind the analyte and couple with the second anchor element; (c) providing a detectable displacer agent configured to couple with the capture agent and release the capture agent from the first anchor element; and (d) detecting a presence or absence of the detectable displacer agent; thereby indicating the presence or absence of the analyte. Also provided are methods for detecting and quantifying an analyte within a sample, comprising: (a) contacting the sample with a colocalization by linkage assay (CLA) complex comprising: (i) a support; (ii) a first anchor element attached to the support; (iii) a second anchor element attached to the support; (iv) a capture agent releasable coupled with the first anchor element, wherein the capture agent is configured to bind the analyte; (b) providing a detection agent configured to bind the analyte and couple with the second anchor element; (c) providing a detectable displacer agent configured to couple with the detection agent and release the detection agent from the second anchor element; and (d) detecting a presence or absence of the detectable displacer agent; thereby indicating the presence or absence of the analyte.

In some embodiments, the detectable displacer agent is detected when the analyte is bound to the capture agent and the detection agent. In some embodiments, the detectable displacer agent is not detected when the analyte is not bound to capture agent, the detection agent, or both. In some embodiments, the first anchor element comprises a first polynucleotide comprising a first anchoring nucleic acid sequence. In some embodiments, the second anchor element comprises a second polynucleotide comprising a second anchoring nucleic acid sequence. In some embodiments, the capture agent is coupled to a third polynucleotide comprising a third nucleic acid sequence complementary to the first anchoring nucleic acid sequence. In some embodiments, in (a), the third nucleic acid sequence is hybridized to the first anchor nucleic acid sequence. In some embodiments, the detection agent is coupled to a fourth polynucleotide comprising a fourth nucleic acid sequence complementary to the second anchoring nucleic acid sequence. In some embodiments, (b) further comprises hybridizing the fourth nucleic acid sequence to the second anchor nucleic acid sequence, thereby coupling the detection agent to the support. In some embodiments, the detectable displacer agent comprises a fifth polynucleotide comprising a fifth nucleic acid sequence complementary a region of the third nucleic acid sequence or a region of the fourth nucleic acid sequence. In some embodiments, the fifth polynucleotide comprises fifth nucleic acid sequence complementary the region of the third nucleic acid sequence, and wherein (c) further comprises hybridizing the fifth polynucleotide to the third polynucleotide, thereby releasing the capture agent from the support. In some embodiments, the fifth polynucleotide comprises fifth nucleic acid sequence complementary the region of the fourth nucleic acid sequence, and wherein (c) further comprises hybridizing the fifth polynucleotide to the fourth polynucleotide, thereby releasing the capture agent from the support. In some embodiments, the one or both of the capture agent and detection agent is an antibody, an antibody fragment, an aptamer, a modified aptamer, a somamer, an affimer, an antigen, a protein, a polypeptide, a multi-protein complex, an exosome, an oligonucleotide, or a low molecular weight compound.

In some embodiments, the capture agent and detection agent are an antibody, an antibody fragment, an aptamer, a modified aptamer, a somamer, an affimer, an antigen, a protein, a polypeptide, a multi-protein complex, an exosome, an oligonucleotide, or a low molecular weight compound. In some embodiments, the capture agent and detection agent are an antibody or an antibody fragment.

In some embodiments, the capture agent and the detection agent bind different epitopes on the analyte. In some embodiments, the analyte is an antigen, an antibody, an affimer, an aptamer, a modified aptamer, a somamer, an antibody fragment, a protein, a polypeptide, a multi-protein complex, an exosome, an oligonucleotide, a hormone, a modified oligonucleotide, or a low molecular weight compound. In some embodiments, the capture agent and the detection agent are both antigens, and the analyte is an antibody. In some embodiments, the capture agent and the detection agent are different antigens, and the antibody is a bispecific antibody or multi-specific antibody. In some embodiments, the sample is a biological sample. In some embodiments, the sample is wherein the sample is a bodily fluid, an extract, a solution containing proteins and/or DNA, a cell extract, a cell lysate, or a tissue lysate. In some embodiments, the sample is a bodily fluid, wherein the bodily fluid is urine, saliva, blood, serum, plasma, cerebrospinal fluid, tears, semen, or sweat. In some embodiments, the detectable displacer agent comprises a fluorophore, a nucleic acid barcode sequence, an enzyme, or a biotin moiety. In some embodiments, detecting comprises quantifying fluorescence of the detectable displacer agent. In some embodiments, detecting comprises sequencing a nucleic acid sequence of the detectable displacer agent, a nucleic acid sequence of the capture agent, a nucleic acid sequence of the detection agent, or a combination thereof.

Further disclosed are methods for detecting an antibody in a sample, comprising: (a) contacting the sample with a colocalization by linkage assay (CLA) complex comprising: (i) a support; (ii) a first anchor element attached to the support; (iii) a second anchor element attached to the support; (iv) an antigen, wherein the antigen is coupled to the first anchor element; (b) providing an isotype-specific binding agent, wherein the isotype-specific binding agent is configured to bind an isotype of the antibody and couple to the second anchor element; (c) providing a detectable displacer agent configured to couple to the antigen and release the antigen from the first anchor element; and (d) detecting a presence or absence of the detectable displacer agent; thereby indicating (1) the presence or absence of the antibody bound to the antigen, and (2) the isotype of the antibody.

In some embodiments, the detectable displacer agent is detected when the antibody is bound to the antigen and the isotype-specific binding agent. In some embodiments, the detectable displacer agent is not detected when the antibody is not bound to antigen, the isotype-specific binding agent, or both. In some embodiments, the first anchor element comprises a first polynucleotide comprising a first anchoring nucleic acid sequence. In some embodiments, the second anchor element comprises a second polynucleotide comprising a second anchoring nucleic acid sequence. In some embodiments, the antigen is coupled to a third polynucleotide comprising a third nucleic acid sequence complementary to the first anchoring nucleic acid sequence. In some embodiments, (a) the third nucleic acid sequence is hybridized to the first anchor nucleic acid sequence.

In some embodiments, the isotype-specific binding agent is coupled to a fourth polynucleotide comprising a fourth nucleic acid sequence complementary to the second anchoring nucleic acid sequence. In some embodiments, (b) further comprises hybridizing the fourth nucleic acid sequence to the second anchor nucleic acid sequence, thereby coupling the isotype-specific binding agent to the support. In some embodiments, the detectable displacer agent comprises a fifth polynucleotide comprising a fifth nucleic acid sequence complementary a region of the third nucleic acid sequence or a region of the fourth nucleic acid sequence. In some embodiments, the fifth polynucleotide comprises fifth nucleic acid sequence complementary the region of the third nucleic acid sequence, and wherein (c) further comprises hybridizing the fifth polynucleotide to the third polynucleotide, thereby releasing the antigen from the support. In some embodiments, the fifth polynucleotide comprises fifth nucleic acid sequence complementary the region of the fourth nucleic acid sequence, and wherein (c) further comprises hybridizing the fifth polynucleotide to the fourth polynucleotide, thereby releasing the antigen from the support. In some embodiments, the isotype-specific binding agent is an antibody.

Also provided are methods of any one of embodiments 27 to 39, wherein the isotype is IgM, IgD, IgG, IgA, or IgE. In some embodiments, isotype-specific binding agent is configured to bind an isotype subclass. In some embodiments, wherein the subclass is IgG1, IgG2, IgG3, or IgG4. In some embodiments, the sample is a biological sample. In some embodiments, the sample is wherein the sample is a bodily fluid, an extract, a solution containing proteins and/or DNA, a cell extract, a cell lysate, or a tissue lysate. In some embodiments, the sample is a bodily fluid, wherein the bodily fluid is urine, saliva, blood, serum, plasma, cerebrospinal fluid, tears, semen, or sweat. In some embodiments, the detectable displacer agent comprises a fluorophore, a nucleic acid barcode sequence, an enzyme, or a biotin moiety. In some embodiments, detecting comprises quantifying fluorescence of the detectable displacer agent. In some embodiments, detecting comprises sequencing a nucleic acid sequence of the detectable displacer agent, a nucleic acid sequence of the capture agent, a nucleic acid sequence of the detection agent, or a combination thereof.

Also provided are methods for characterizing an analyte in a sample, comprising: (a) contacting the sample with a colocalization by linkage assay (CLA) complex comprising: (i) a support; (ii) a first anchor element attached to the support; (iii) a second anchor element attached to the support; (iv) a capture agent releasably coupled to the first anchor element, wherein the capture agent is configured to bind the analyte; (b) providing a detection agent, wherein the detection agent binds a post-translational modification of the analyte and releasably couple to the second anchor element; (c) providing a detectable displacer agent configured to couple to the capture agent and release the capture agent from the first anchor element; and (d) detecting a presence or absence of the detectable displacer agent; thereby indicating (1) the presence or absence of the analyte, and (2) the post-translational modification. Provided are methods for characterizing an analyte in a sample, comprising: (a) contacting the sample with a colocalization by linkage assay (CLA) complex comprising: (i) a support; (ii) a first anchor element attached to the support; (iii) a second anchor element attached to the support; (iv) a capture agent releasably coupled to the first anchor element, wherein the capture agent is configured to bind the analyte; (b) providing a detection agent, wherein the detection agent binds a post-translational modification of the analyte and couple to the second anchor element; (c) providing a detectable displacer agent configured to couple to the detection agent and release the detection agent from the second anchor element; and (d) detecting a presence or absence of the detectable displacer agent; thereby indicating (1) the presence or absence of the analyte, and (2) the post-translational modification.

In some embodiments, the detectable displacer agent is detected when the analyte is bound to the capture agent and the detection agent. In some embodiments, the detectable displacer agent is not detected when the analyte is not bound to capture agent, the detection agent, or both. In some embodiments, the first anchor element comprises a first polynucleotide comprising a first anchoring nucleic acid sequence. In some embodiments, the second anchor element comprises a second polynucleotide comprising a second anchoring nucleic acid sequence. In some embodiments, the capture agent is coupled to a third polynucleotide comprising a third nucleic acid sequence complementary to the first anchoring nucleic acid sequence. In some embodiments, (a) the third nucleic acid sequence is hybridized to the first anchor nucleic acid sequence. In some embodiments, the detection agent is coupled to a fourth polynucleotide comprising a fourth nucleic acid sequence complementary to the second anchoring nucleic acid sequence. In some embodiments, (b) further comprises hybridizing the fourth nucleic acid sequence to the second anchor nucleic acid sequence, thereby coupling the detection agent to the support.

In some embodiments, the detectable displacer agent comprises a fifth polynucleotide comprising a fifth nucleic acid sequence complementary a region of the third nucleic acid In some embodiments, the fifth polynucleotide comprises fifth nucleic acid sequence complementary the region of the third nucleic acid sequence, and wherein (c) further comprises hybridizing the fifth polynucleotide to the third polynucleotide, thereby releasing the capture agent from the support. In some embodiments, the fifth polynucleotide comprises fifth nucleic acid sequence complementary the region of the fourth nucleic acid sequence, and wherein (c) further comprises hybridizing the fifth polynucleotide to the fourth polynucleotide, thereby releasing the capture agent from the support.

In some embodiments, one or both of the capture agent and detection agent is an antibody, an antibody fragment, an aptamer, a modified aptamer, a somamer, an affimer, an antigen, a protein, a polypeptide, a multi-protein complex, an exosome, an oligonucleotide, or a low molecular weight compound. In some embodiments, the capture agent and detection agent are an antibody, an antibody fragment, an aptamer, a modified aptamer, a somamer, an affimer, an antigen, a protein, a polypeptide, a multi-protein complex, an exosome, an oligonucleotide, or a low molecular weight compound In some embodiments, the capture agent and detection agent are an antibody or an antibody fragment. In some embodiments, the analyte is an antigen, an antibody, an affimer, an aptamer, a modified aptamer, a somamer, an antibody fragment, a protein, a polypeptide, a multi-protein complex, an exosome, an oligonucleotide, a hormone, a modified oligonucleotide, or a low molecular weight compound. In some embodiments, the post-translation modification comprises phosphorylation, glycosylation, ubiquitination, nitrosylation, methylation, acetylation, lipidation, or a combination thereof. In some embodiments, the sample is a biological sample. In some embodiments, the sample is wherein the sample is a bodily fluid, an extract, a solution containing proteins and/or DNA, a cell extract, a cell lysate, or a tissue lysate.

In some embodiments, detecting comprises quantifying fluorescence of the detectable displacer agent.

In some embodiments, detecting comprises sequencing a nucleic acid sequence of the detectable displacer agent, a nucleic acid sequence of the capture agent, a nucleic acid sequence of the detection agent, or a combination thereof.

Further provided are colocalization by linkage assay (CLA) compositions for the characterization of an antibody, comprising: a CLA complex comprising: (i) a support; (ii) a first anchor element attached to the support; (iii) a second anchor element attached to the support; (iv) an antigen, wherein the antigen is releasably coupled to the first anchor element; and (b) an isotype-specific binding agent, wherein the isotype-specific binding agent is configured to bind an isotype of the antibody and couple to the second anchor element. In some embodiments, the isotype-specific binding agent is an antibody. In some embodiments, the isotype is IgM, IgD, IgG, IgA, or IgE. In some embodiments, the isotype-specific binding agent is configured to bind an isotype subclass. In some embodiments, the subclass is IgG1, IgG2, IgG3, or IgG4. Also provided ae colocalization by linkage assay (CLA) compositions for the characterization of an analyte, comprising: a CLA complex comprising: (i) a support; (ii) a first anchor element attached to the support; (iii) a second anchor element attached to the support; (iv) a capture agent releasably coupled to the first anchor element, wherein the capture agent is configured to bind the analyte; and (b) a detection agent, wherein the detection agent binds a post-translational modification of the analyte and couple to the second anchor element.

In some embodiments, the capture agent and the detection agent binding agent is an antibody. In some embodiments, the post-translation modification comprises phosphorylation, glycosylation, ubiquitination, nitrosylation, methylation, acetylation, lipidation, or a combination thereof.

Further provided are methods for detecting and quantifying an analyte within a sample, comprising: (a) contacting the sample with a capture agent configured to bind the analyte and couple with a support, thereby generating a first complex comprising the analyte bound to the capture agent; (b) contacting the first complex with a detection agent configured to bind the analyte and releasably couple with the support, thereby generating a second complex comprising (i) the analyte bound to the capture agent and the detection agent, and (ii) the detection agent coupled with the support, wherein the detection agent is releasably coupled with the support; (c) providing a detectable displacer agent configured to bind the capture agent and release the capture agent from the support; thereby releasing the capture agent from the support; and (d) detecting a presence of the detectable displacer agent from the second complex, thereby identifying the presence of the analyte.

Figure 15:
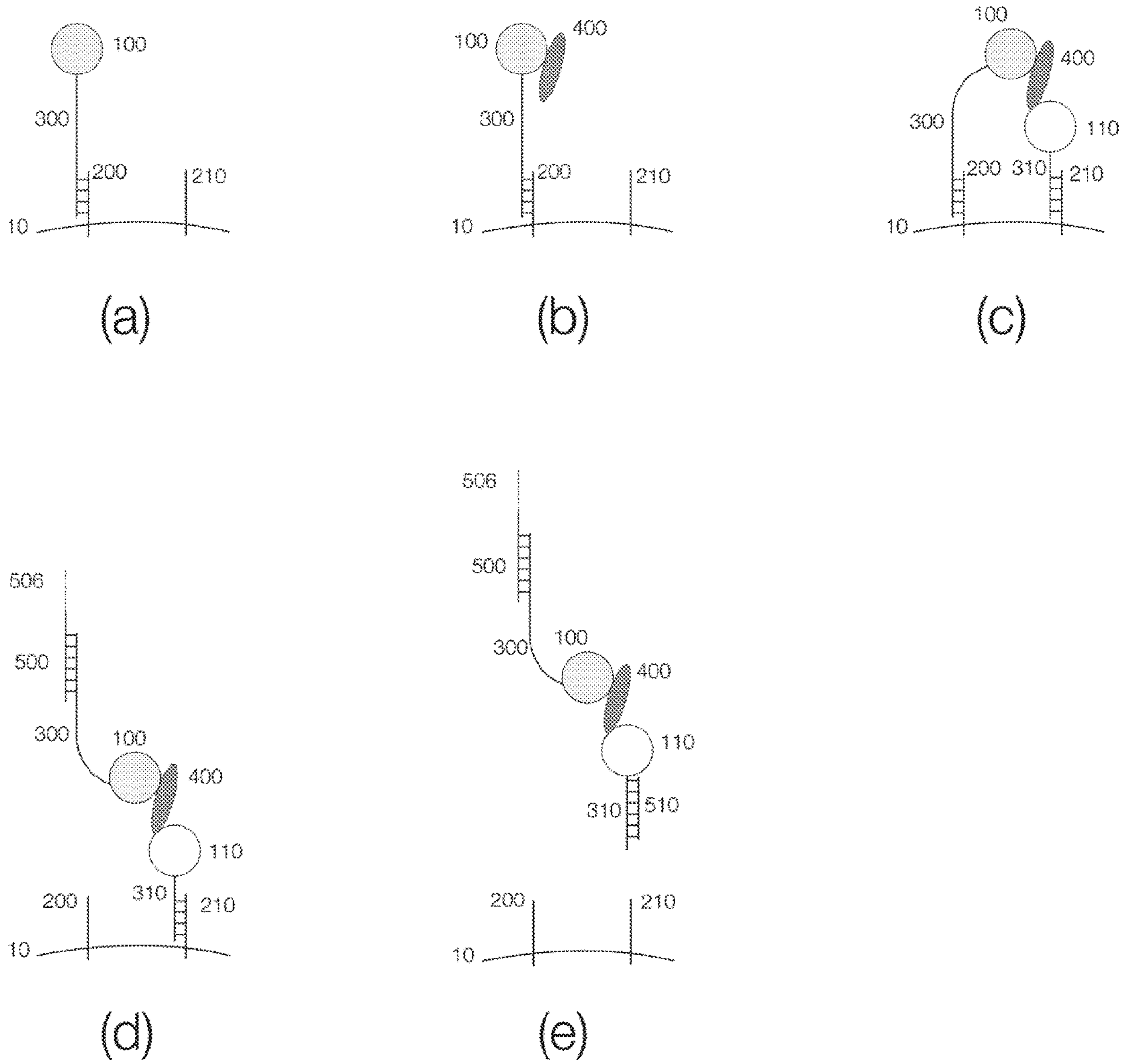
FIG. 15(*a*)-15(*e*) shows a schematic of one embodiment of a 1-plex pCLAMP with an additional analyte-dependent displacement reaction.

Exemplifying the compositions and methods described herein, FIG. 15 demonstrates a posterior colocalization-by-linkage assay composition that includes analyte-dependent displacement. As shown in FIG. 15*a*, a posterior colocalization-by-linkage assay composition is assembled on a microparticle support (10) and comprises (1) a first analyte-specific binder (100) that is conjugated to a first linker oligonucleotide (300) that is releasably attached to the support via a first anchor oligonucleotide (200). The composition is interfaced with an analyte-containing sample, and the analyte (400) forms a complex with the first analyte-specific binder (FIG. 15*b*). After optically washing the support, a second binder specific to the analyte (110), conjugated to a second linker oligonucleotide (310), can be introduced. The second linker oligo hybridizes to the second anchor oligo linked on to the same support, thereby securely linking the second binder to the support. If the analyte is present in the sample and has been captured by the first binder, then at least some of the second binders will bind to a second epitope on the analyte (FIG. 15*c*). A complex between an analyte and the detection and capture reagents is thereby generated. A detectably labeled first displacer reagent (500), labeled with an identifiable DNA sequence (506), is provided (FIG. 15*d*), and the detectably labeled first displacer reagent specifically binds to the first linker oligonucleotide, displacing the first analyte-specific binder from the first anchor oligonucleotide. Any displaced first analyte-specific binder that is not coupled to the support via the detection complex can be removed by washing. A second displacer reagent (510) is provided (FIG. 15*e*), and the second displacer reagent specifically binds to the second linker oligo, displacing the second analyte-specific binder from the second linker, thereby releasing the detection complex from the support. The released first linker oligonucleotide can then be processed, and/or the detectably labeled first displacer reagent can be analyzed as described herein, to identify the first analyte-specific binder and hence quantify the analyte.

Poly-CLAMP Detection Complexes

Multiplexing offers several distinct advantages over single-plex immunoassay, particularly the small sample volume and times required to obtain the same amount of information. Traditional singleplex immunoassay e.g. ELISA can be miniaturized to reduce sample volume requirements and can be run in parallel using microfluidic approach. However, the singleplex assay format bears fundamental limitations that the target sample need to be split for individual reaction and each of the reaction need to be individually processed. To address these limitations, multiplexing enables multiple analytes to be profiled simultaneously. Planar and bead-based assay are two commonly used formats to facilitate multiplexing. Barcoded (or encoded) microparticles, in particular, are often used in multiplexed suspension assays as they allow particles in a large mixture to be distinguished. The methods of barcoding include, but not limited to spectral, graphical, or chemical means.

As the number of analytes targeted in a multiplexed assay increases, the requirements on the number of arrays becomes prohibitive in terms of cost and complexity. For instance, a 10-plex assay requires 10 different bead sets or 10 microarray sets, whereas 1,000-plex assay necessitates 1,000 different bead sets or microarray sets. As such, the amount of material needed to perform high-plex assays becomes a significant limitation to efficiency and scale, and cost can scale linearly with the number of analytes targeted.

Additionally, an increased number of arrays necessitates a large assay volume which increases sample volume requirements and makes it difficult to miniaturize assays. For example, 5,000 bead sets at 100 beads per set is 0.5 million beads per well, which necessitates a larger volume of assay, at least 30-50 μL, which is higher than the volume capacity of a 1536-well plate. Similarly, for single-cell applications, single cells are either partitioned in a small well or a small droplet; in both cases, the assay volume is in the 1-10 pL range. The volume of a single cell can be as small as 0.1 pL and would also have to be diluted $>10^9$ folds to be analyzed in a large assay volume in order to be analyzed at high multiplexing levels. Such low-volume application as single cell analysis represents challenges for bead-based assays including CLAMP assays.

The compositions provided herein can be useful in the analysis of partitioned single cells or partitioned populations of cells. In particular, the compositions provided herein overcome deficiencies with CLA on microparticles (CLAMP). Namely, many CLAMP beads would have to be pooled together with a population of cells, or a single cell, to generate multiple analyte-specific readouts. For instance, measuring 10 proteins from a smaller population of cells or a single cell would require pooling 10 different sets of beads in with each population of cells or single cell, as required. Partitioning multiple single-plex CLAMPs into small partitions, especially into partitions encapsulating a single cell, is technically difficult and is likely to result in many encapsulations without all CLAMPs present. Likewise, it becomes difficult or impossible to encapsulate a sufficient number of CLAMP beads within the small volume within an encapsulated droplet. The polyCLAMP constructs provided herein enable a single microparticle support to generate multiple analyte-specific readouts, and hence as little as one polyCLAMP microparticle can be partitioned along with a population of cells, or a single cell. As such, polyCLAMP constructs are compatible with common cell encapsulation approaches, including microfluidics.

Provided herein are compositions and methods for the detection of multiple analytes using a single detection complex or multiple colocalization-by-linkage detection reagents coupled with a single support. Accordingly, provided herein are colocalization-by-linkage assay compositions for analysis of analytes in a sample. In some embodiments, the colocalization-by-linkage assay composition comprises: (a) a detection complex comprising (i) a support, (ii) a first capture reagent and a first detection reagent complexed with the support via a first anchoring element, and (iii) a second capture reagent and a second detection reagent complexed with the support via a second anchoring element; and (b) a first detectable displacer reagent and a second detectable displacer reagent, wherein the first detectable displacer reagent is configured to displace the first detection reagent from the first anchoring element, and the second detectable displacer reagent is configured to displace the second detection reagent from the second anchoring element. For example, also provided are colocalization-by-linkage assay compositions comprising a complex comprising a plurality of detection complexes (e.g. a capture reagent and detection reagent) coupled to a single support (e.g. a bead or microparticle), wherein the plurality comprises a first detection complex and a second detection complex. In some embodiments, the first and the second detection complexes each recognize a different analyte. By way of further example, any one of the of the colocalization-by-linkage assay compositions described herein can be configured to recognize two or more different analytes on a single support. This can be achieved by adding at least a second detection complex configured to recognize a second analyte, to the support. In such embodiments, the detection complexes can be configured to provide different readouts by differing the detection elements (e.g. a barcode sequence, primer binding sequence, displacer dependent binding sequences, etc.).

The use of displacer-dependent detection facilitates effective readouts and increased detection sensitivity. In some embodiments, the detection complex further comprises the first detectable displacer reagent after displacing the first detection reagent from the first anchoring element when a first analyte is coupled to the first capture reagent and the first detection reagent. In some embodiments, the detection complex further comprises the second detectable displacer reagent after displacing the second detection reagent from the second anchoring element when a second analyte is coupled to the second capture reagent and the second detection reagent. In some embodiments, the detection complex further comprises (1) the first detectable displacer reagent after displacing the first detection reagent from the first anchoring element when the first analyte is coupled to the first capture reagent and the first detection reagent, and (2) the second detectable displacer reagent after displacing the second detection reagent from the second anchoring element when a second analyte is coupled to the second capture reagent and the second detection reagent. In some embodiments, the detection complex does not comprise the first detectable displacer reagent after displacing the first detection reagent and when the first analyte is not coupled with one or both of the first capture reagent and first detection reagent. In some embodiments, the detection complex does not comprise the second detectable displacer reagent after displacing the second detection reagent and when the second analyte is not coupled with one or both of the second capture reagent and second detection reagent. In some embodiments, the detection complex does not comprise (1) the first detectable displacer reagent a after displacing the first detection reagent and when the first analyte is not coupled with one or both of the first capture reagent and first detection reagent, and (2) the second detectable displacer reagent after displacing the second detection reagent and when the second analyte is not coupled with one or both of the second capture reagent and second detection reagent.

In some embodiments, multiplexing and labeling can be simultaneously achieved by CLAMP reagents that use specific DNA sequences as barcodes, wherein specific sequence is used as the label or as barcodes for a specific analyte. For example, specific barcoding DNA sequence can be included in the hook strand, whereby after the detection-by-displacement, the hook strand from a singleplex or multiplex assay can be released from the solid support and read by methods including, but not limited to: hybridization-based microarrays, e.g. solid phase DNA chips and beads arrays; Single molecule methods, e.g, nanostring; and DNA sequencing methods, e.g. next generation sequencing (including Roche 454, Illumina HiSeq, Pacific Biosciences SMRT and the like) and single molecule sequencing (including Oxford nanopore platform and Pacific Biosciences SMRT platform and the like).

Provided herein is colocalization-by-linkage assay composition for analysis of analytes in a sample, the colocalization-by-linkage assay composition comprising:

(a) a detection complex comprising (i) a support, (ii) a first capture reagent and a first detection reagent complexed with the support, wherein the first capture reagent and first detection reagent are configured to simultaneously bind to the first analyte and (iii) a second capture reagent and a second detection reagent complexed with the support, wherein the second capture reagent and second detection reagent are configured to simultaneously bind to the second analyte;

(b) a first displacer reagent and a second displacer reagent, wherein the first displacer reagent is configured to displace the first and second detection reagents from the support, and the second displacer reagent is configured to displace the first and second capture reagents from the support.

The detection complex can utilize a number of configurations and elements used therein to achieve detection of an analyte in a sample. For example, an anchoring element that comprises or consists of an oligonucleotide can be used for generating microparticles with specific detection reagents through the use of complementary nucleic acid sequences of the oligonucleotides used in generating the detection complex. In some embodiments, the detection complex further comprises (iv) a first anchor element coupled with the support and (v) a second anchor element coupled with the support. In some embodiments, the first anchor element and second anchor element are a nucleic acid molecule. In some embodiments, first tethering element and second tethering element are a nucleic acid molecule. In some embodiments, the first anchoring element is coupled with the first tethering element. In some embodiments, the second anchoring element is coupled with the second tethering element. In some embodiments, the first anchoring element is coupled with the first tethering element, and the second anchoring element is coupled with the second tethering element. In some embodiments, the first detection reagent comprises a first detection hook element and the first capture reagent comprises a first capture hook element. In some embodiments, the first detection hook element and the first capture hook element are releasably coupled to the first anchoring element. In some embodiments, the first detection hook element and first capture hook element each consist of a nucleic acid molecule. In some embodiments, the first anchoring element comprises a first detection reagent anchoring sequence and the first detection hook element comprises a first detection linker sequence complementary to the first detection reagent anchoring sequence, and the first anchoring element comprises a first capture reagent anchoring sequence and the first capture hook element comprises a first capture linker sequence complementary to the first capture reagent anchoring sequence.

Displacer-dependent detection can achieve effective labeling and detection through interactions with a hook element, wherein any detection reagent not complexed with the support through an analyte-mediated complex is displaced from the detection complex. In some embodiments, the second detection reagent comprises a second detection hook element and the second capture reagent comprises a second capture hook element. In some embodiments, the second detection hook element and the second capture hook element are releasably coupled to the second anchoring element. In some embodiments, the second detection hook element and second capture hook element each consist of a nucleic acid molecule. In some embodiments, the second anchoring element comprises a second detection reagent anchoring sequence and the second detection hook element comprises a second detection linker sequence complementary to the second detection reagent anchoring sequence, and the second anchoring element comprises a second capture reagent anchoring sequence and the second capture hook element comprises a second capture linker sequence complementary to the second capture reagent anchoring sequence. In some embodiments, the first detection reagent comprises a first detection hook element and first capture reagent comprises a first capture hook element, and the second detection reagent comprises a second detection hook element and second capture reagent comprises a second capture hook element. In some embodiments, the first detection hook element and the first capture hook element are releasably coupled to the first anchoring element, and the second detection hook element and the second capture hook element are releasably coupled to the second anchoring element. In some embodiments, the first detectable displacer reagent is configured to couple with the first detection hook element, or a portion thereof, thereby decoupling the first detection hook element from the first anchoring element.

The displacer reagent can be highly specific for a hook element through the use of displacer reagents comprising oligonucleotides. Such oligonucleotides can also be used for further processing of information denoting the detection of an analyte. In some embodiments, the first detectable displacer reagent comprises a nucleic acid molecule. In some embodiments, the first detection hook element comprises an additional sequence adjacent to the first detection linker sequence and the detectable displacer reagent comprises a first detection displacer sequence complementary to the additional sequence and at least a portion of the first detection linker sequence. In some embodiments, the first detection displacer sequence has a melting temperature greater than that of the first detection anchoring sequence. In some embodiments, the second detectable displacer reagent is configured to couple with the second detection hook element, or a portion thereof, thereby decoupling the second detection hook element from the second anchoring element. In some embodiments, the second detectable displacer reagent comprises a nucleic acid molecule. In some embodiments, the second detection hook element comprises an additional sequence adjacent to the second detection linker sequence and the detectable displacer reagent comprises a second displacer sequence complementary to the additional sequence and at least a portion of the second detection linker sequence. In some embodiments, the second detection displacer sequence has a melting temperature greater than that of the second detection anchoring sequence.

Displacer-dependent detection can also comprise displacing a capture reagent, wherein the capture reagent comprises further information related to the detection of an analyte. For example, both a capture reagent and a detection reagent can each comprise an oligonucleotide. The oligonucleotides of a complex comprising a capture reagent, a detection reagent, and an analyte can be further processed to identify the capture reagent, the detection reagent, and the analyte. In some embodiments, the colocalization-by-linkage assay composition further comprises: (c) a third detectable displacer reagent and a fourth detectable displacer reagent, wherein the third detectable displacer reagent is configured to displace the first capture reagent from the first anchoring element, and the fourth detectable displacer reagent is configured to displace the second capture reagent from the second anchoring element. In some embodiments, the third detectable displacer reagent is configured to couple with the first capture hook element, or a portion thereof, thereby decoupling the first capture hook element from the first anchoring element. In some embodiments, the third detectable displacer reagent comprises a nucleic acid molecule. In some embodiments, the first capture hook element comprises an additional sequence adjacent to the first capture linker sequence and the third detectable displacer reagent comprises a first capture displacer sequence complementary to the additional sequence and at least a portion of the first capture linker sequence. In some embodiments, the first capture displacer sequence has a melting temperature greater than that of the first capture anchoring sequence. In some embodiments, the fourth detectable displacer reagent is configured to couple with the second capture hook element, or a portion thereof, thereby decoupling the second capture hook element from the second anchoring element. In some embodiments, the fourth detectable displacer reagent comprises a nucleic acid molecule. In some embodiments, the second capture hook element comprises an additional sequence adjacent to the second capture linker sequence and the fourth detectable displacer reagent comprises a second displacer sequence complementary to the additional sequence and at least a portion of the second capture linker sequence. In some embodiments, the second capture displacer sequence has a melting temperature greater than that of the second capture anchoring sequence. In some embodiments, the first capture reagent and the first detection reagent are a different antibody or antigen-binding fragment thereof and bind to a different epitope on a first analyte. In some embodiments, the second capture reagent and the second detection reagent are a different antibody or antigen-binding fragment thereof and bind to a different epitope on a second analyte.

Detection via the coupling of a detection or capture reagent with an analyte can be achieved by any number of binding-molecules known within the art. In some embodiments, the first detection reagent and the first capture reagent are selected from the group consisting of: an antibody or an antigen-binding fragment thereof, an aptamer, a modified aptamer, a somamer, an affimer, an antigen, a protein, a polypeptide, a multi-protein complex, an exosome, an oligonucleotide, a low molecular weight compound, and any combination thereof. In some embodiments, the second detection reagent and the second capture reagent are selected from the group consisting of: an antibody or an antigen-binding fragment thereof, an aptamer, a modified aptamer, a somamer, an affimer, an antigen, a protein, a polypeptide, a multi-protein complex, an exosome, an oligonucleotide, a low molecular weight compound, and any combination thereof.

Detection and capture reagents comprising oligonucleotides (e.g. a hook element) can be used to detect an analyte through the processing of the oligonucleotides corresponding to the detection and capture reagents. Exemplary oligonucleotide or nucleic acid processing includes amplification, ligation, and/or primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "TAQMAN™" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the disclosure are produced by PCRs. An amplification reaction can be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which can include, but not be limited to, buffering agents to maintain pH at a selected level during a reaction, salts, co-factors, scavengers, and the like.

Nucleic acid sequencing can be applied to identify oligonucleotide sequences that correspond to the capture and detection reagents. Nucleic acid sequencing technologies can derive the nucleic acids that they sequence from collections of cells obtained from tissue or other samples, such as biological fluids (e.g., blood, plasma, etc). The cells can be processed (e.g., all together in an ensemble approach) to extract the genetic material that represents an average of the population of cells, which can then be processed into sequencing ready DNA libraries that are configured for a given sequencing technology.

In some embodiments, the first detection reagent comprises a first detection hook element a nucleic acid sequence selected from the group consisting of a primer sequence, a barcode sequence, a unique molecular identifier sequence, a displacer sequence, a sequence configured to couple to a flow cell of a sequencer, and any combination thereof. In some embodiments, the first capture reagent comprises first capture hook element comprising a nucleic acid sequence selected from the group consisting of a primer sequence, a barcode sequence, a unique molecular identifier sequence, a displacer sequence, a sequence configured to couple to a flow cell of a sequencer, and any combination thereof. In some embodiments, the second detection reagent comprises a second detection hook element comprising a nucleic acid sequence selected from the group consisting of a primer sequence, a barcode sequence, a unique molecular identifier sequence, a displacer sequence, a sequence configured to couple to a flow cell of a sequencer, and any combination thereof. In some embodiments, the second capture reagent comprises a second capture hook element comprising a nucleic acid sequence selected from the group consisting of a primer sequence, a barcode sequence, a unique molecular identifier sequence, a displacer sequence, a sequence configured to couple to a flow cell of a sequencer, and any combination thereof.

In some embodiments, the second capture reagent comprises a cleavable second capture hook element. In some embodiments, the cleavable first capture hook element is photocleavable. In some embodiments, the cleavable first capture hook element is cleavable by an enzyme. In some embodiments, the enzyme is a nucleic acid restriction enzyme. In some embodiments, the cleavable first capture hook element is cleavable by a chemical stimulus.

In some embodiments, the first detectable displacer reagent, second detectable displacer reagent, third detectable displacer reagent, or fourth detectable displacer reagent comprises a detectable label selected from the group consisting of a fluorescent polymer, a biotin molecule, a fluorophore, an enzyme, a nucleic acid enzyme, a riboswitch, an enzyme substrate, a nucleic acid sequence, and any combination thereof.

In some embodiments, the support is a microparticle, a nanoparticle, a microbead, a nanobead, a magnetic bead, a well in a plate, an array, a microfluidic chip, a lateral flow strip, a slide, a flow cell, a porous polymer, or a hydrogel.

Also disclosed herein are methods of detecting analytes in a sample using the colocalization-by-linkage assay compositions described herein. Such methods comprise: (a) delivering a detection complex as to a sample comprising a plurality of analytes; (b) providing the first detectable displacer reagent and the second detectable displacer reagent, thereby displacing the first detection reagent from the first anchoring element, and the second detection reagent from the second anchoring element; and (c) detecting the presence of the first detectable displacer reagent and the second detectable displacer reagent. In some embodiments, the plurality of analytes comprises a first analyte, and wherein the first capture reagent and the first detection reagent couple with the first analyte.

In some embodiments, the detection complex comprises the first detectable displacer reagent after (b). In some embodiments, the plurality of analytes comprises a second analyte, and wherein the second capture reagent and the second detection reagent couple with the second analyte. In some embodiments, the detection complex comprises the second detectable displacer reagent after (b). In some embodiments, the method comprises further comprises prior to (b), removing analytes not coupled with said detection complex. In some embodiments, the method further comprises prior to (c), (i) removing a first detectable displacer reagent not complexed with the support and (ii) removing a second detectable displacer reagent not complexed with the support. In some embodiments, the method further comprises subsequent to (b), (i) displacing the first capture reagent and the second capture reagent from the support. In some embodiments, detecting the presence of the first detectable displacer reagent and the second detectable displacer reagent comprises using a sequencing reaction to detect the presence of a nucleic acid sequence corresponding to the first detectable displacer reagent or the second detectable displacer reagent. In some embodiments, detecting the presence of the first detectable displacer reagent and the second detectable displacer reagent comprises using fluorescent detection to detect a fluorescent label corresponding to the first detectable displacer reagent or the second detectable displacer reagent. In some embodiments, the sample is a biological sample. In some embodiments, the sample is a bodily fluid, a whole blood sample, a cell supernatant, an extract, a cell extract, a cell lysate, a tissue lysate, a solution comprising nucleic acid molecules, or a solution comprising proteins.

Colocalization-by-linkage compositions can also be engineered wherein a detection complex comprises a single support coupled with (1) a capture reagent that recognizes an analyte and (2) a first and a second detection reagent wherein the first and the second detection reagents couple with different regions or locations (e.g. epitopes) on the same analyte. Accordingly, such a composition is useful in the multiplexed profiling of epitopes on an analyte. Thus, provided herein are colocalization-by-linkage assay compositions for analysis of analytes in a sample, the colocalization-by-linkage assay composition comprising: (a) a detection complex comprising (i) a support, (ii) a capture reagent coupled with the support; (iii) a first detection reagent complexed with the support via a first anchoring element, and (iv) a second detection reagent complexed with the support via a second anchoring element; and (b) a first detectable displacer reagent and a second detectable displacer reagent, wherein the first detectable displacer reagent is configured to displace the first detection reagent from the first anchoring element, and the second detectable displacer reagent is configured to displace the second detection reagent from the second anchoring element. In some embodiments, the detection complex further comprises the first detectable displacer reagent after displacing the first detection reagent from the first anchoring element when a first analyte is coupled to the capture reagent and the first detection reagent. In some embodiments, the detection complex further comprises the second detectable displacer reagent after displacing the second detection reagent from the second anchoring element when a second analyte is coupled to the capture reagent and the second detection reagent. In some embodiments, the detection complex further comprises the first detectable displacer reagent after displacing the first detection reagent from the first anchoring element when the first analyte is coupled to the capture reagent and the first detection reagent, and the second detectable displacer reagent after displacing the second detection reagent from the second anchoring element when a second analyte is coupled to the capture reagent and the second detection reagent. In some embodiments, the detection complex does not comprise the first detectable displacer reagent after displacing the first detection reagent and when the first analyte is not coupled with one or both of the capture reagent and first detection reagent. In some embodiments, the detection complex does not comprise the second detectable displacer reagent after displacing the second detection reagent and when the second analyte is not coupled with one or both of the capture reagent and second detection reagent.

In some embodiments, the detection complex does not comprise (1) the first detectable displacer reagent a after displacing the first detection reagent and when the first analyte is not coupled with one or both of the capture reagent and first detection reagent, and (2) the second detectable displacer reagent after displacing the second detection reagent and when the second analyte is not coupled with one or both of the capture reagent and second detection reagent. In some embodiments, the detection complex further comprises (iv) a first anchor element coupled with the support and (v) a second anchor element coupled with the support.

In some embodiments, the first anchor element and second anchor element are a nucleic acid molecule. In some embodiments, the first tethering element and second tethering element are a nucleic acid molecule. In some embodiments, the first anchoring element is coupled with the first tethering element. In some embodiments, the second anchoring element is coupled with the second tethering element. In some embodiments, the first anchoring element is coupled with the first tethering element, and the second anchoring element is coupled with the second tethering element. In some embodiments, the first detection reagent comprises a first detection hook.

In some embodiments, the first detection hook element is releasably coupled to the first anchoring element. In some embodiments, the first detection hook element consists of a nucleic acid molecule. In some embodiments, the first anchoring element comprises a first detection reagent anchoring sequence and the first detection hook element comprises a first detection linker sequence complementary to the first detection reagent anchoring sequence. In some embodiments, the second detection reagent comprises a second detection hook element In some embodiments, the second detection hook element is releasably coupled to the second anchoring element In some embodiments, the second detection hook element consists of a nucleic acid molecule. In some embodiments, the second anchoring element comprises a second detection reagent anchoring sequence and the second detection hook element comprises a second detection linker sequence complementary to the second detection reagent anchoring sequence. In some embodiments, the first detection reagent comprises a first detection hook element, and the second detection reagent comprises a second detection hook element. In some embodiments, the first detection hook element is releasably coupled to the first anchoring element, and the second detection hook element is releasably coupled to the second anchoring element.

In some embodiments, the first detectable displacer reagent is configured to couple with the first detection hook element, or a portion thereof, thereby decoupling the first detection hook element from the first anchoring element. In some embodiments, the first detectable displacer reagent comprises a nucleic acid molecule. In some embodiments, the first detection hook element comprises an additional sequence adjacent to the first detection linker sequence and the detectable displacer reagent comprises a first detection displacer sequence complementary to the additional sequence and at least a portion of the first detection linker sequence. In some embodiments, the first detection displacer sequence has a melting temperature greater than that of the first detection anchoring sequence. In some embodiments, the second detectable displacer reagent is configured to couple with the second detection hook element, or a portion thereof, thereby decoupling the second detection hook element from the second anchoring element. In some embodiments, the second detectable displacer reagent comprises a nucleic acid molecule. In some embodiments, the second detection hook element comprises an additional sequence adjacent to the second detection linker sequence and the detectable displacer reagent comprises a second displacer sequence complementary to the additional sequence and at least a portion of the second detection linker sequence. In some embodiments, the second detection displacer sequence has a melting temperature greater than that of the second detection anchoring sequence.

In some embodiments, the capture reagent is selected from the group consisting of: an antibody or an antigen-binding fragment thereof, an aptamer, a modified aptamer, a somamer, an affimer, an antigen, a protein, a polypeptide, a multi-protein complex, an exosome, an oligonucleotide, a low molecular weight compound, and any combination thereof. In some embodiments, the first detection reagent comprises a first detection hook element a nucleic acid sequence selected from the group consisting of a primer sequence, a barcode sequence, a unique molecular identifier sequence, a displacer sequence, a sequence configured to couple to a flow cell of a sequencer, and any combination thereof.

In some embodiments, the first detection reagent and second detection reagent are selected from the group consisting of: an antibody or an antigen-binding fragment thereof, an aptamer, a modified aptamer, a somamer, an affimer, an antigen, a protein, a polypeptide, a multi-protein complex, an exosome, an oligonucleotide, a low molecular weight compound, and any combination thereof.

In some embodiments, the second detection reagent comprises a second detection hook element comprising a nucleic acid sequence selected from the group consisting of a primer sequence, a barcode sequence, a unique molecular identifier sequence, a displacer sequence, a sequence configured to couple to a flow cell of a sequencer, and any combination thereof.

In some embodiments, the second capture reagent comprises a second capture hook element comprising a nucleic acid sequence selected from the group consisting of a primer sequence, a barcode sequence, a unique molecular identifier sequence, a displacer sequence, a sequence configured to couple to a flow cell of a sequencer, and any combination thereof.

In some embodiments, the capture reagent and the first detection reagent are a different antibody or antigen-binding fragment thereof and bind to a different epitope on a first analyte. In some embodiments, the capture reagent and the second detection reagent are a different antibody or antigen-binding fragment thereof and bind to a different epitope on a second analyte. In some embodiments, the first detectable displacer reagent and second detectable displacer reagent comprises a detectable label selected from the group consisting of a fluorescent polymer, a biotin molecule, a fluorophore, an enzyme, a nucleic acid enzyme, a riboswitch, an enzyme substrate, a nucleic acid sequence, and any combination thereof.

In some embodiments, the support is a microparticle, a nanoparticle, a microbead, a nanobead, a magnetic bead, a well in a plate, an array, a microfluidic chip, a lateral flow strip, a slide, a flow cell, a porous polymer, or a hydrogel.

Further disclosed herein are methods of detecting analytes in a sample, using a detection complex comprising a single support coupled with (1) a capture reagent that recognizes an analyte and (2) a first and a second detection reagent wherein the first and the second detection reagents couple with different regions or locations (e.g. epitopes) on the same analyte, wherein the method comprises: (a) delivering the detection complex to a sample comprising a plurality of analytes; (b) providing the first detectable displacer reagent and the second detectable displacer reagent, thereby displacing the first detection reagent from the first anchoring element, and the second detection reagent from the second anchoring element; and (c) detecting the presence of the first detectable displacer reagent and the second detectable displacer reagent. FIG. 2 shows an exemplary method of multiplexed epitope profiling analysis, wherein a plurality of antibodies complexed with a support recognize different epitopes on an analyte in a biological sample. Unbound or detection reagents not in complex with the bead are displaced and removed. The hook elements consisting of an oligonucleotide can be processed in order to identify the detection reagent(s) coupled with an analyte.

In some embodiments, the plurality of analytes comprises a first analyte, and wherein the first capture reagent and the first detection reagent couple with the first analyte. In some embodiments, the detection complex comprises the first detectable displacer reagent after (b). In some embodiments, the plurality of analytes comprises a second analyte, and wherein the second capture reagent and the second detection reagent couple with the second analyte. In some embodiments, the detection complex comprises the second detectable displacer reagent after (b). In some embodiments, the method further comprises prior to (b), removing analytes not coupled with said detection complex. In some embodiments, the method further comprises prior to (c), (i) removing a first detectable displacer reagent not complexed with the support and (ii) removing a second detectable displacer reagent not complexed with the support. In some embodiments, the method further comprises subsequent to (b), (i) displacing the first capture reagent and the second capture reagent from the support.

In some embodiments, detecting the presence of the first detectable displacer reagent and the second detectable displacer reagent comprises using a sequencing reaction to detect the presence of a nucleic acid sequence corresponding to the first detectable displacer reagent or the second detectable displacer reagent. In some embodiments, detecting the presence of the first detectable displacer reagent and the second detectable displacer reagent comprises using fluorescent detection to detect a fluorescent label corresponding to the first detectable displacer reagent or the second detectable displacer reagent.

In some embodiments, the sample is a biological sample. In some embodiments, the sample is a bodily fluid, a whole blood sample, a cell supernatant, an extract, a cell extract, a cell lysate, a tissue lysate, a solution comprising nucleic acid molecules, or a solution comprising proteins.

Nucleic acid sequences can be used for the analysis of analytes and the conditions from which they were derived. Particularly, barcode nucleic acids and/or unique molecular identifier sequence. In some embodiments, the methods described herein further comprise subjecting the barcoded nucleic acid fragment to one or more reactions to generate a set of nucleic acid molecules for nucleic acid sequencing. In some embodiments, the one or more reactions comprise nucleic acid amplification that generates amplified products from the barcoded nucleic acid fragment. In some embodiments, the nucleic acid amplification adds functional sequences to the amplified products, wherein the functional sequences permit attachment of the amplified products to a flow cell of a sequencer for the nucleic acid sequencing. In some embodiments, the one or more reactions comprise ligating functional sequences to the barcoded nucleic acid fragment, or a derivative thereof, wherein the functional sequences permit attachment to a flow cell of a sequencer for the nucleic acid sequencing. In some embodiments, the methods further comprise ligating functional sequences to the amplified products, wherein the functional sequences permit attachment of the amplified products to a flow cell of a sequencer for the nucleic acid sequencing. In some embodiments, each bead of the plurality of beads comprises a plurality of barcode oligonucleotide molecules comprising a common barcode sequence that is different from barcode sequences in other beads of the plurality of beads. In some embodiments, each of the barcode oligonucleotide molecules comprise the common barcode sequence and a unique molecular sequence, wherein the common barcode sequence is constant across the nucleic acid barcode molecules, and wherein the unique molecular sequence varies across the nucleic acid barcode molecules.

FIG. 3 demonstrates exemplary barcoded elements of the compositions described herein. FIG. 3 also demonstrates an exemplary partitioning schema that allows for multiplexed analysis of oligos derived from a plurality of analytes and/or samples. Such methods can be used for the effective detection and multiplexing of analytes within a plurality of samples. Accordingly, disclosed are methods of analyzing analytes in a sample, the method comprising: (a) delivering a detection complex to a sample comprising a plurality of analytes, wherein the detection complex comprises a support coupled with a capture reagent and (i) a first detection reagent comprising a first oligonucleotide and complexed with the support via a first anchoring element, and (ii) a second detection reagent comprising a second oligonucleotide and complexed with the support via a second anchoring element; (b) decoupling the first detection reagent from the first anchoring element and the second detection reagent from the second anchoring element, thereby displacing any detection reagent not coupled with an analyte of the plurality of analytes and complexed with the support; and (c) detecting a first nucleic acid molecule corresponding to the first oligonucleotide and a second nucleic acid molecule corresponding to the second oligonucleotide.

The oligonucleotides can comprise nucleic acid sequences that facilitate the processing and identification of detection. In some embodiments, the first oligonucleotide and the second oligonucleotide comprise a barcode sequence, a primer binding sequence, a unique molecular identifier sequence, an adapter sequence, a sequence configured to couple to a flow cell of a sequencer, a displacer binding sequence, or any combination thereof. In some embodiments, one or both of the barcode sequence and unique molecular identifier sequence comprise a sequence that corresponds to a single experiment or sample among a plurality of experiments plurality of samples. In some embodiments, one or both of the barcode sequence and unique molecular identifier sequence comprise a sequence that corresponds to a sample in a partition. In some embodiments, (b) comprises providing a first detectable displacer reagent and a second detectable displacer reagent, wherein the first detectable displacer reagent is configured to displace the first detection reagent from the first anchoring element, and the second detectable displacer reagent is configured to displace the second detection reagent from the second anchoring element. In some embodiments, the first detectable displacer reagent and the second displacer reagent comprise an oligonucleotide. In some embodiments, one or both of the first detectable displacer reagent and the second displacer reagent comprise a barcode sequence, a primer binding sequence, a unique molecular identifier sequence, a sequence configured to couple to a flow cell of a sequence, or any combination thereof.

In some embodiments, prior to (b), the sample is removed from the detection complex and the detection complex is washed to remove any analytes of the plurality of analytes not complexed with the detection complex. In some embodiments, prior to (c), the sample is removed from the detection complex and the detection complex is washed to remove any analytes of the plurality of analytes not complexed with the detection complex.

The compositions as disclosed herein are useful in the method for the analysis of an analyte. In some embodiments, the detection complex further comprises a first capture reagent complexed with the support via a first anchoring element, and a second capture reagent detection reagent complexed with the support via a first anchoring element. In some embodiments, the detection complex further comprises a capture reagent coupled with the support. In some embodiments, the detection complex comprises a capture reagent. In some embodiments, the detection complex comprises one or more capture reagents. In addition to thermally cleavable bonds, disulfide bonds and UV sensitive bonds, other non-limiting examples of labile bonds that can be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., a DNAase, a DNAzyme, an RNAzyme, an aptazyme, a riboswitch)). In some embodiments, the capture reagent is releasably coupled with the detection complex. In some embodiments, the capture reagent is released by a stimulus. In some embodiments, the capture reagent is released by a photo stimulus. In some embodiments, the capture reagent is released by an enzyme, a DNAzyme, an RNAzyme, an aptazyme, and/or a riboswitch.

In some embodiments, the capture reagent comprises an oligonucleotide. In some embodiments, the oligonucleotide comprises a barcode sequence, a primer binding sequence, a unique molecular identifier sequence, a sequence configured to couple to a flow cell of a sequence, or any combination thereof.

In some embodiments, the support is a microparticle, a nanoparticle, a microbead, a nanobead, a magnetic bead, a well in a plate, an array, a microfluidic chip, a lateral flow strip, a slide, a flow cell, a porous polymer, or a hydrogel.

In some embodiments, the first detection reagent is configured to couple with a first analyte and second detection reagent is configured to couple with a second analyte. In some embodiments, the first analytes and the second analyte are a different analyte.

In some embodiments, the first detection reagent and second detection reagent are configured to couple with different regions of a single analyte.

In some embodiments, prior to (a), the method comprises partitioning the sample and the detection complex into a partition. In some embodiments, prior to (b), the method comprises partitioning the sample and the detection complex into a partition. In some embodiments, prior to (c), the method comprises partitioning the sample and the detection complex into a partition.

In some embodiments, the partition is a well. In some embodiments, the partition is a emulsion droplet. In some embodiments, the partition is an encapsulated droplet. In some embodiments, the well is among a plurality of wells. In some embodiments, the well among the plurality of wells corresponds to a specific barcode or adapter sequence. In some embodiments, the plurality of wells is configured to correspond to a specific barcode or adapter sequence, or a set of barcode or adapter sequences. In some embodiments, the specific barcode or adapter sequence encodes information corresponding to a specific sample or set of samples, a specific detection complex or set of detection complexes, and/or a specific experiment or set of experiments. In some embodiments, the barcode or adapter sequence encodes information corresponding to a sample index. In certain embodiments, the sample index encodes a sequence corresponding to a specific detection reagent, a specific sample, a specific set of samples, a specific detection reagent or set of detection reagents, a specific analyte or set of analytes.

In some embodiments, the sample is a biological sample. In some embodiments, the sample is a bodily fluid, a whole blood sample, a cell supernatant, an extract, a cell extract, a cell lysate, a tissue lysate, a solution comprising nucleic acid molecules, or a solution comprising proteins.

In some embodiments, before or after addition of displacer reagents, a single (or multiple) perturbing reagent is added to the CLAMP complexes, such as a perturbagen or protease or kinase. The reagent can disrupt the analytes and/or cause complexed detection reagents to release from the support-bound complex. The impact of the perturbing reagent(s) can be assessed via readout of the hook element or displacer element corresponding to the released detection reagents in the supernatant. Next, the complex can be washed, and the capture reagent decoupled from the support, thereby enabling the readout of the subsequently released complexes. The hook elements and/or displacer reagents can then be processed and sequenced or analyzed by qPCR or collector beads to identify the detection reagent(s) and analyte(s).

In some embodiments, the method is performed in a partition comprising cells, cell lysates, or a biological sample. The partitions can be pooled and combined with other partitions wherein the barcode sequences corresponding to the hook oligos and/or displacer oligos can be identified and used to identify a sample as coming from a particular partition.

Supports

The colocalization-by-linkage compositions and methods described herein generally utilize a support in the detection and/or quantification of an analyte. In certain instances, the term "support" refers to an immobilizing structure, surface or substrate, such as without limitation a microparticle, a nanoparticle, a well in a plate, a flow cell, a porous polymer, a bead, or a hydrogel. In some embodiments, the support is a microparticle. In some embodiments, the support is a nanoparticle. In some embodiments, the support is a well in a plate. In some embodiments, the support is a flow cell. In some embodiments, the support is a porous polymer. In some embodiments, the support is a bead. In some embodiments, the support is a hydrogel.

In certain instances, a "bead" generally refers to a particle (e.g. a microparticle). The bead can be a solid or semi-solid particle. The bead can be formed of a polymeric material. The bead can be magnetic or non-magnetic.

It should be understood that the support is not meant to be particularly limited, and any solid, semi-solid, gel or gel-like structure can be used. For example, a support can be an array, a bead (such as without limitation a polystyrene bead), the surface of a multi-well plate (such as a 96-well plate, a 384-well plate, etc.), the surface of a glass slide, a sequencing flow cell, a surface-plasmon-resonance flow cell, a hydrogel matrix, a microfluidic chip, a lateral flow strip, a glass surface, a plastic surface, a silicon surface, a ceramic surface, and the like. In some embodiments, the support is a bead or microparticle or nanoparticle, typically micron-sized or nano-sized, such as without limitation a polystyrene bead, a magnetic bead, a paramagnetic bead, a plastic bead, etc. In another embodiment, the support is a planar microarray.

In some embodiments, where the support is a microparticle (MP), certain advantages can be obtained. For example, in some embodiments the ability to rapidly read out a large number of MPs by flow cytometry can afford increased precision and sample throughput In addition, MPs can be functionalized in large batches and then stored, used, and read-out while in solution, which can reduce lot-to-lot variability and enable quantitative analysis (Tighe, P. J., et al., Proteomics-Clinical Applications 9, 406-422, 2015; Jani, I. V., et al., The Lancet 2, 243-250, 2002; Krishhan, V. V., Khan, I. H. & Luciw, P. a. Multiplexed microbead immunoassays by flow cytometry for molecular profiling: Basic concepts; Tighe, P., et al., Utility, reliability and reproducibility of immunoassay multiplex kits. Methods (San Diego, Calif.) 1-7 2013; Fu, Q., et al., Clinical applications 4, 271-84, 2010). Exemplary supports are further described in, U.S. Pre-Grant Publication No. US20200319173, which is herein incorporated by reference in its entirety.

In some embodiments, the bead can contain molecular precursors (e.g., monomers or polymers), which can form a polymer network via polymerization of the precursors. In some embodiments, a precursor can be an already polymerized species capable of undergoing further polymerization via, for example, a chemical cross-linkage. In some embodiments, a precursor comprises one or more of an acrylamide or a methacrylamide monomer, oligomer, or polymer. In some embodiments, the bead can comprise prepolymers, which are oligomers capable of further polymerization. For example, polyurethane beads can be prepared using prepolymers. In some embodiments, the bead can contain individual polymers that can be further polymerized together. In some embodiments, beads can be generated via polymerization of different precursors, such that they comprise mixed polymers, co-polymers, and/or block co-polymers.

In certain instances, a bead can comprise natural and/or synthetic materials. For example, a polymer can be a natural polymer or a synthetic polymer. In some embodiments, a bead comprises both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly (vinyl acetate), poly(vinyl alcohol), poly(vinyl chloride), poly(vinylidene dichloride), poly(vinylidene difluoride), poly(vinyl fluoride) and combinations (e.g., co-polymers) thereof. Beads can also be formed from materials other than polymers, including lipids, micelles, ceramics, glass-ceramics, material composites, metals, other inorganic materials, and others.

As will be appreciated, in some instances, polynucleotides and/or barcodes that are releasably, cleavable or reversibly attached to the beads described herein include polynucleotides and/or barcodes that are released or releasable through cleavage of a linkage between the polynucleotide and/or barcode molecule and the bead allowing the polynucleotides or barcodes to be accessed or accessible by other reagents, or both.

In addition to thermally cleavable bonds, disulfide bonds and UV sensitive bonds, other non-limiting examples of labile bonds that can be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase, e.g., a DNAase, a DNAzyme, an RNAzyme, an aptazyme, a riboswitch).

Beads can be of uniform size or heterogeneous size. In some embodiments, the diameter of a bead can be about 1 μm, 5 μm, 10 μm, 20 μm, 30 μm, 40 μm, 50 μm, 60 μm, 70 μm, 80 μm, 90 μm, 100 μm, 250 μm, 500 μm, or 1 mm. In some cases, a bead can have a diameter of at least about 1 μm, 5 μm, 10 μm, 20 μm, 30 μm, 40 μm, 50 μm, 60 μm, 70 μm, 80 μm, 90 μm, 100 μm, 250 μm, 500 μm, 1 mm, or more. In some cases, a bead can have a diameter of less than about 1 μm, 5 μm, 10 μm, 20 μm, 30 μm, 40 μm, 50 μm, 60 μm, 70 μm, 80 μm, 90 μm, 100 μm, 250 μm, 500 μm, or 1 mm. In some cases, a bead can have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In certain aspects, beads are provided as a population or plurality of beads having a relatively monodisperse size distribution. Where it can be desirable to provide relatively consistent amounts of reagents within partitions, maintaining relatively consistent bead characteristics, such as size, can contribute to the overall consistency.

In some embodiments, the microparticles are encoded so that, for example, a first microparticle can be differentiated from a second microparticle. In certain instances, the term "encoded microparticle" refers to a micron-sized microparticle that is encoded spectrally according to either the target analyte or the specific test that is to be performed in the assay. Exemplary encoded microparticles are further described in U.S. Pre-Grant Publication No. US20200319173 and U.S. Pre-Grant Publication No. US20190237166, which are herein incorporated by reference in their entirety.

Analytes

The colocalization-by-linkage compositions and methods described herein are useful in or for the detection and/or quantification of an analyte or analytes in a sample. In certain instances, the term "analyte" refers to a targeted biomolecule or biological cell of interest which is being identified, detected, measured and/or quantified. An analyte can be any biomolecule or biological cell which can be detected using the systems and methods provided herein, such as without limitation proteins, nucleic acids (DNAs, RNAs, etc.), antibodies, antigens, proteins, cells, chemicals, biomarkers, enzymes, polypeptides, amino acids, polymers, carbohydrates, multi-protein complexes, exosomes, oligonucleotides, low molecular weight compounds, and the like. Non-limiting examples of analytes include antibodies, antibody fragments (e.g., scFv, Fab, etc.), aptamers, modified aptamers, somamers, affimers, antigens, proteins, polypeptides, multi-protein complexes, exosomes, oligonucleotides, and low molecular weight compounds.

In certain instance, the analyte is within a sample. As used herein, a "sample" refers to any fluid or liquid sample which is being analyzed in order to detect and/or quantify an analyte. In some embodiments, a sample is a biological sample. Examples of samples include without limitation a bodily fluid, an extract, a solution containing proteins and/or DNA, a cell extract, a cell lysate, or a tissue lysate. Non-limiting examples of bodily fluids include urine, saliva, blood, serum, plasma, cerebrospinal fluid, tears, semen, sweat, pleural effusion, liquified fecal matter, and lacrimal gland secretion. The biological sample can be a nucleic acid sample or protein sample. The biological sample can be derived from another sample. The sample can be a tissue sample, such as a biopsy, core biopsy, needle aspirate, or fine needle aspirate. The sample can be a fluid sample, such as a blood sample, urine sample, or saliva sample. The sample can be a skin sample. The sample can be a cheek swap. The sample can be a plasma or serum sample. The sample can be a cell-free or cell free sample. A cell-free sample can include extracellular polynucleotides. The samples can also comprise or be derived from a single cell. Extracellular polynucleotides can be isolated from a bodily sample that can be selected from the group consisting of blood, plasma, serum, urine, saliva, mucosal excretions, sputum, stool and tears. Exemplary analytes and samples are further described in, U.S. Pre-Grant Publication No. US20200319173, which is herein incorporated by reference in its entirety.

In some embodiments, the sample or analytes are analyzed, detected, measured, or quantified within a partition. In certain instances, the term "partition" can be a verb or a noun. In certain instances, when used as a verb (e.g., "to partition," or "partitioning"), the term generally refers to the fractionation (subdivision) of a species or sample (e.g., a polynucleotide) between vessels that can be used to sequester one fraction (or subdivision) from another. Such vessels are referred to using the noun "partition." Partitioning can be performed, for example, using microfluidics, dilution, dispensing, and the like. A partition can be, for example, a well, a microwell, a hole, a droplet (e.g., a droplet in an emulsion), test tube, a spot, a capsule, or any other suitable container for sequestering one fraction of a sample from another.

Affinity Molecules

In general, the colocalization-by-linkage compositions and methods described herein utilize affinity molecules (e.g. an antibody) that specifically recognize and bind an analyte. In certain instances, the terms "affinity binder" (AB), "binding element", "affinity element", "binding reagent", "binder", and "reactant" are used interchangeably to mean any molecule capable of specifically recognizing a target analyte (e.g. via a non-covalent interaction). In some embodiments, affinity reagents include capture reagent (e.g. a first antibody) and a detection reagent (e.g. a second antibody). Examples of affinity binders (ABs) include without limitation immunoglobulin-G (IgG) antibodies (e.g., whole molecules or Fab fragments), aptamers, affimers, nanobodies, ankyrins, and single-chain variable fragments (scFvs). Exemplary affinity molecules are further described in, U.S. Pre-Grant Publication No. US20200319173, which is herein incorporated by reference in its entirety.

In some instances, the term "non-specific binding" refers to an unintended reaction between reagents and/or molecules within the sample, including but not limited to reaction between non-cognate antibodies and protein sticking through hydrophobic interactions. In some instances, As used herein, the term "cross-reactivity" is used to mean a particular case of non-specific binding or non-specific reaction in a multiplexed sandwich assay, wherein an unintended complex is formed that includes non-cognate affinity binders, e.g., as shown in FIG. 4.

In certain instances, the term "sandwich assay" is used to mean an analyte-targeting assay wherein two ABs (e.g. affinity reagents) simultaneously bind the target analyte of interest and can be used to detect and/or quantify it. In certain instances, the terms "multiplex sandwich assay", "multiplexed sandwich assay" and "MSA" are used interchangeably to mean a sandwich assay that targets multiple (e.g., two or more) analytes from the same sample and/or assay volume at the same time, multiple AB pairs (e.g. pairs of affinity reagents) being used in the assay system at the same time.

In certain instances, the terms "capture affinity binder", "cAB", "capture AB", "capture binder" and "capture reagent" interchangeably to refer to an AB (e.g. affinity reagent) that is attached to a support in a biomolecule complex and is not released from it. A capture AB (e.g. capture reagent) can be attached directly to a support (e.g., via a covalent bond, a biotin-streptavidin bond, a DNA oligonucleotide linker, or a polymer linker) or indirectly (e.g., via linkage to a tethering or an anchor strand, e.g., by conjugation or through a linker such as a capture strand). Non-limiting examples of capture reagents include antibodies, antibody fragments (e.g., scFv, Fab, etc.), aptamers, modified aptamers (such as slow off-rate modified aptamers or somamers), affimers, antigens, proteins, polypeptides, multi-protein complexes, exosomes, oligonucleotides, and low molecular weight compounds. In certain instances, the term "capture strand" refers to a linker (e.g., an oligonucleotide, a polymer, etc.) that links a capture reagent to an anchor element (and hence the support to which the anchor strand is attached).

As used herein, the terms "detection affinity binder", "dAB", "detection AB", "detection binder" and "detection reagent" are used interchangeably to refer to an AB (e.g. affinity reagent) in a biomolecule complex that is releasably attached to a support. The dAB (e.g. detection reagent) is generally used for signal transduction and assay signaling. In some embodiments of methods and systems provided herein, for example, the fraction of dAB (e.g. detection reagent) unbound to an analyte is released from the support such that no signal is produced in the absence of bound analyte. In some embodiments, the dAB (e.g. detection reagent) is bound to a label or means for signal transduction and assay signaling. Non-limiting examples of detection reagents include antibodies, antibody fragments (e.g., scFv, Fab, etc.), aptamers, modified aptamers, somamers, affimers, antigens, proteins, polypeptides, multi-protein complexes, exosomes, oligonucleotides, and low molecular weight compounds.

It should be understood that systems and methods provided herein can be used in virtually any type of sandwich assay wherein two sets of ABs are used. However, for simplicity, specific embodiments of the present disclosure are presented herein using whole-molecule Immunoglobulin-G antibodies (IgG) as ABs, which represents one of many possible embodiments. It should be understood that antibodies are not limited to whole-molecule IgG and that many different antibodies, antibody fragments, etc. can be used. Further, ABs are not limited to antibodies. Similarly, many different types of sandwich assays other than the specific ones described herein can be used.

Additional CLA Structural Elements and Oligonucleotides

Generally, the detection reagent and a capture reagent of a CLA composition are linked to the support via linker (e.g. a hook element anchored to an anchor element). In certain instances, as used herein, the term "anchor strand" or "anchor element" refers to a linker that attaches to an immobile point on a support. Non-limiting examples of anchor strands include polymers, such as polyethylene glycol (PEG), oligonucleotides (such as a single-stranded DNA oligonucleotide, a single-stranded RNA oligonucleotide, or a double-stranded DNA or RNA oligonucleotide, or a DNA-RNA hybrid), and oligosaccharides. In certain instances, the term "linked" or "coupled" refers to the association of two or more molecules. The linkage can be covalent or non-covalent. The linkage also can be genetic (i.e., recombinantly fused). Such linkages can be achieved using a wide variety of art recognized techniques, such as chemical conjugation In some embodiments, is an oligonucleotide. In some embodiments, an anchor strand can be greater than about 5 nucleotides in length, greater than about 10 nucleotides in length, greater than about 20, 30, 40, 50, 60, 70, 80, 90, 100, 120, 150 or even 200 nucleotides in length. In some cases, an anchor strand can be less than about 250 nucleotides in length, less than about 200, 180, 150, 120 100, 90, 80, 70, 60, 50, 40, or even 30 nucleotides in length.

In certain instances, the term "tethering strand" or "tethering element" can also refer to a linker that attaches to an immobile point on a support. Non-limiting examples of tethering strands include oligonucleotides (such as a single-stranded DNA oligonucleotide, a single-stranded RNA oligonucleotide, or a double-stranded DNA or RNA oligonucleotide, or a DNA-RNA hybrid).

In some embodiments, a tethering strand can be greater than about 5 nucleotides in length, greater than about 10 nucleotides in length, greater than about 20, 30, 40, 50, 60, 70, 80, 90, 100, 120, 150 or even 200 nucleotides in length. In some cases, a tethering strand can be less than about 250 nucleotides in length, less than about 200, 180, 150, 120 100, 90, 80, 70, 60, 50, 40, or even 30 nucleotides in length In certain instances, the term "hook strand" or "hook element" refers to a linker that links an affinity reagent (e.g. a detection reagent and/or a capture reagent) to a anchoring element or anchor strand and hence attaches it to a support. Generally, the hook strand is releasably attached releasably to the anchoring element or the anchor strand, e.g., in such a way that the attachment can be released. Generally, when the attachment between the hook strand and the anchor strand is released, the fraction of affinity reagent (e.g. a detection reagent and/or a capture reagent) linked to the hook strand that is not bound to a target analyte will be released from the anchoring element or anchor strand, and therefore also released from the support, such that no signal from the detection affinity reagent (e.g. a detection reagent and/or a capture reagent) can be detected on the support in the absence of the target analyte. In this way, signal is only detected when the target analyte is present and bound by the detection AB (e.g. detection reagent) and the capture AB (e.g. capture reagent).

In some embodiments, a hook strand can be greater than about 5 nucleotides in length, greater than about 10 nucleotides in length, greater than about 20, 30, 40, 50, 60, 70, 80, 90, 100, 120, 150 or even 200 nucleotides in length. In some cases, a hook strand can be less than about 250 nucleotides in length, less than about 200, 180, 150, 120 100, 90, 80, 70, 60, 50, 40, or even 30 nucleotides in length.

In certain instances, "polynucleotide" or "oligonucleotide" is used interchangeably and each means a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, wobble base pairing, or the like. As described in detail below, by "wobble base" is meant a nucleic acid base that can base pair with a first nucleotide base in a complementary nucleic acid strand but that, when employed as a template strand for nucleic acid synthesis, leads to the incorporation of a second, different nucleotide base into the synthesizing strand. Such monomers and their internucleosidic linkages can be naturally occurring or can be analogs thereof, e.g. naturally occurring or non-naturally occurring analogs. Non-naturally occurring analogs can include peptide nucleic acids (PNAs, e.g., as described in U.S. Pat. No. 5,539,082, incorporated herein by reference), locked nucleic acids (LNAs, e.g., as described in U.S. Pat. No. 6,670,461, incorporated herein by reference), phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions.

Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they can also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

In certain instances, the term "barcode" generally refers to a label, or identifier, that can be part of an analyte to convey information about the analyte. A barcode can be a tag attached to an analyte (e.g., nucleic acid molecule) or a combination of the tag in addition to an endogenous characteristic of the analyte (e.g., size of the analyte or end sequence(s)). The barcode can be unique. Barcodes can have a variety of different formats, for example, barcodes can include: polynucleotide barcodes; random nucleic acid and/or amino acid sequences; synthetic nucleic acid and/or amino acid sequences; and florescent or optically decodable chemical moieties. A barcode can be attached to an analyte in a reversible or irreversible manner. The barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads in real time. In some examples, the barcode is generated in a combinatorial manner. Any polynucleotide sequence described herein can comprise a barcode sequence and be used with methods, devices and systems of the present disclosure. The nucleic acid barcode sequences can include from 6 to about 20 or more nucleotides within the sequence of the oligonucleotides. In some embodiments, the length of a barcode sequence can be 6, 7, 8, 9, 10, 11, 12, 13, 14, 15, 16, 17, 18, 19, 20 nucleotides or longer. In some embodiments, the length of a barcode sequence can be at least 6, 7, 8, 9, 10, 11, 12, 13, 14, 15, 16, 17, 18, 19, 20 nucleotides or longer. In some embodiments, the length of a barcode sequence can be at most 6, 7, 8, 9, 10, 11, 12, 13, 14, 15, 16, 17, 18, 19, 20 nucleotides or shorter. These nucleotides can be completely contiguous, i.e., in a single stretch of adjacent nucleotides, or they can be separated into two or more separate subsequences that are separated by 1 or more nucleotides. In some embodiments, separated barcode subsequences can be from about 4 to about 16 nucleotides in length. In some embodiments, the barcode subsequence can be 4, 5, 6, 7, 8, 9, 10, 11, 12, 13, 14, 15, 16 nucleotides or longer. In some embodiments, the barcode subsequence can be at least 4, 5, 6, 7, 8, 9, 10, 11, 12, 13, 14, 15, 16 nucleotides or longer. In some embodiments, the barcode subsequence can be at most 4, 5, 6, 7, 8, 9, 10, 11, 12, 13, 14, 15, 16 nucleotides or shorter.

In some embodiments, where a label is on the hook strand and/or the detection reagent and is only activated or detectable after the release of the hook strand and/or the detection reagent from the anchoring element or the anchor strand, the signal is "release-dependent", as it will only be detectable after the release of the hook strand and/or the detection reagent from the anchoring element or the anchor strand. Similarly, in some embodiments, where the label is on a displacer agent hybridizing to the hook strand, the signal is "displacement-dependent".

The oligonucleotides described herein can, in some embodiments, be releasably attached to the support. In some embodiments, an oligonucleotide in directly attached to the support. In some embodiments, an oligonucleotide is indirectly linked or attached to a support. The oligonucleotides described herein can be releasably attached to the support. In some embodiments, an oligonucleotide is releasable attached to a support. In some embodiments, the application of a stimulus allows an oligonucleotide to dissociate or to be released from the support. Such stimulus can disrupt the microcapsule, an interaction that couples the oligonucleotide to the support. Such stimulus can include, for example, a thermal stimulus, photo-stimulus (e.g. photocleavage), chemical stimulus (e.g., change in pH or use of a reducing agent(s)), a mechanical stimulus, a radiation stimulus, a biological stimulus (e.g., enzyme), or any combination thereof. In some embodiments, the application of a displacer agent allows an oligonucleotide to dissociate or to be released from the support.

In certain instances, the term "displacer agent" refers to an agent that directly or indirectly causes or initiates release of the releasable linkage between the anchoring element or the anchor strand and the hook strand, thereby releasing the hook strand (and the detection AB (e.g. detection reagent) linked thereto) from the support. The mechanism used by the displacer agent is not particularly limited. For example, the displacer agent can directly or indirectly cause or initiate cleavage, displacement, or unbinding of the linkage between the anchoring element or the anchor strand and the hook strand; other mechanisms are possible and are also contemplated. In some embodiments, the hook strand is displaced from the anchoring element or the anchor strand using a DNA oligonucleotide that hybridizes to the hook strand and/or the anchoring element or the anchor strand. Examples of displacer agents include but are not limited to a displacement DNA oligonucleotide, a source of mono- or polychromatic light, a restriction enzyme, and a reducing agent such as dithiothreitol (DTT). In some embodiments, where photocleavable DNA segments are used, the displacer agent can be a light which effects release via a photocleavage reaction. In some embodiments, the displacer agent is labeled, e.g., with a dye, a fluorophore, a specific DNA sequence, an enzyme, a biotin moiety, and the like. When the displacer agent is labeled, it can serve the dual-function of releasing the hook strand and labelling it simultaneously.

In certain instances, the term "detection element" or "detectable element" includes an element, structure, or property that facilitates detection of a molecule comprising the detection element. In some embodiments, a detection element is a barcode sequence that identifies a molecule comprising the barcode sequence. For example, this would include an affinity molecule (e.g. detection reagent) comprising an antibody and a oligonucleotide linked thereto, wherein the oligonucleotide comprises a detection element. In some embodiments, the detection element comprises a barcode nucleic acid molecule, a protein binding sequence, a primer binding sequence, a unique molecular identifier sequence, a probe binding sequence, a displacer agent binding sequence, etc. In some embodiments, the detection element can be directly or indirectly detected by any number of techniques, for example, sequencing, PCR, qPCR, probe-based detection, fluorescent-based detection. In certain instances, the detection element can be included on any oligonucleotide used in a CLAMP assay.

In cases where the hook strand and anchor strand are DNA oligonucleotides, the displacing agent can be a heated buffer solution that melts the DNA duplex and releases the hook strand. Alternatively, the displacing agent can be another oligonucleotide which releases the hook strand via a toe-hold displacement reaction. The length of the toe-hold can be 1, 2, 3, 4, 5, 6, 7, 8, 9, 10, or more than 10 nucleotides. In some embodiments, the toe-hold measures 9 nucleotides in length. According to Zhang, D. Y. and Winfree, E., Journal of the American Chemical Society, vol. 131, issue 47, pp. 17303-17314, 2009, the displacement reaction rate increases with the length of the toe-hold region until about 9 nucleotides, beyond which additional nucleotides have no effect on the reaction rate.

In certain instances, the term "label" refers to any molecule or a portion of a molecule that generates a signal, can be targeted with a signal-generating molecule, or is otherwise detectable. Examples of labels include but are not limited to biotin, fluorophores, enzymes, enzyme substrates, and specific DNA sequences. An "inactive" or "undetectable" label refers to a label which is not active, is masked, or is otherwise undetectable, e.g., not capable of generating a detectable signal, such as without limitation a quenched fluorescent dye.

In certain instances, "linkers" and "strands" used in methods and systems provided herein are not particularly limited. Non-limiting examples of linkers and strands include DNA oligonucleotides (also referred to as DNA oligos), polymers, polysaccharides, and the like. DNA linkages can be covalent, such as conjugation between a hook strand oligo and a detection AB, or non-covalent, such as hybridization or base-stacking between two complementary DNA sequences. To allow formation of a capture AB (e.g. capture reagent)-antigen-detection AB (e.g. detection reagent) tertiary complex, the hook strand is designed to have a flexible, single-stranded portion. Displacement of a DNA linkage can be performed using several methods including but not limited to a toe-hold mediated DNA displacement reaction, enzymatic cleavage, and photo-activated cleavage. Specific DNA sequences can also be used as labels, which can be either directly targeted using a complementary sequence that is fluorescently labeled, can be used as amplification triggers or primers through a hybridization-chain reaction or a polymerase-chain reaction, and can be read-out via sequencing.

Exemplary CLA elements, as described above, are further described in, U.S. Pre-Grant Publication No. US20200319173, which is herein incorporated by reference in its entirety.

In certain instances, the term "Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer sites, such reaction comprising one or more repetitions of the following steps: (i) denaturing the target nucleic acid, (ii) annealing primers to the primer sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid can be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred μL, e.g. 200 μL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("TAQMAN™"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30:1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999) (two-color real-time PCR). Usually, distinct sets of primers are employed for each sequence being amplified.

In certain instances, the term "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that can be assayed separately or together with a target sequence. The reference sequence can be endogenous or exogenous to a sample or specimen, and in the latter case, can comprise one or more competitor templates. Typical endogenous reference sequences include segments of transcripts of the following genes: β-actin, GAPDH, β2-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

In certain instances, the term "primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but can alternatively be double-stranded. If double-stranded, the primer is usually first treated to separate its strands before being used to prepare extension products. This denaturation step is typically affected by heat, but can alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

In certain instances, the term "sequencing," as used herein, generally refers to methods and technologies for determining the sequence of nucleotide bases in one or more polynucleotides. The polynucleotides can be, for example, deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina, Pacific Biosciences, Oxford Nanopore, or Life Technologies (Ion Torrent). As an alternative, sequencing can be performed using nucleic acid amplification, polymerase chain reaction (PCR) (e.g., digital PCR, quantitative PCR, or real time PCR) or isothermal amplification. Such devices can provide a plurality of raw genetic data corresponding to the genetic information of a subject (e.g., human), as generated by the device from a sample provided by the subject. In some situations, systems and methods provided herein can be used with proteomic information.

It should be understood that this disclosure is not limited to specific devices, systems, methods, or uses or process steps, and as such they can vary.

In order to provide a clear and consistent understanding of the terms used in the present specification, a number of definitions are provided below. Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The use of the word “a” or “an” when used in conjunction with the term “comprising” in the claims and/or the specification can mean “one”, but it is also consistent with the meaning of “one or more”, “at least one”, and “one or more than one”. Similarly, the word “another” can mean at least a second or more.

As used in this specification and claim(s), the words “comprising” (and any form of comprising, such as “comprise” and “comprises”), “having” (and any form of having, such as “have” and “has”), “including” (and any form of including, such as “include” and “includes”) or “containing” (and any form of containing, such as “contain” and “contains”), are inclusive or open-ended and do not exclude additional, unrecited elements or process steps.

As used herein, the term “about” in the context of a given value or range refers to a value or range that is within 20%, preferably within 10%, and more preferably within 5% of the given value or range.

As used herein, the term “and/or” is to be taken as specific disclosure of each of the two specified features or components with or without the other. For example, “A and/or B” is to be taken as specific disclosure of each of (i) A, (ii) B and (iii) A and B, just as if each were set out individually herein.

EXAMPLES

The following examples are included for illustrative purposes only and are not intended to limit the scope of the disclosure.

Example 1: Fabrication of CLAMP Sensors for Multiplexed Detection of SARS-CoV-2 Antibodies In some embodiments, the multiplexed assay system was implemented on spectrally-encoded beads, wherein a one-pot bead barcoding strategy and automated decoding method can be used in methods and systems provided herein. Examples of such barcoding/decoding methods are described in U.S. patent application Ser. No. 16/153,071 and in Dagher, M. et al., Nature Nanotechnology, vol. 13, pp. 925-932, 2018, the contents of each of which are incorporated by reference herein in their entirety. Such methods use accurate models of fluorophore spectral overlap and multicolor Forster-resonance energy transfer (FRET).

In some embodiments of multiplexed serological assays measuring antibodies targeting several targets of a specific viral strain, for example SARS-CoV-2. Each of the Virus specific antigens and fragments including spike protein(S), nucleocapsid protein (N), envelope protein (E), spike protein S1/S2/RBS domains, are tethered to the surface of separate and barcoded magnetic particles. The same manufacturing workflows were used to build multiplex serological assay as described herein. Namely, in a first step, streptavidin beads at a concentration of 400 k/uL were incubated with biotinylated antigen and biotinylated anchor and/or capture oligos modified with different dyes to yield a distinguishable barcode. Each barcode, and antigen, were incubated in separate tubes at room temperature for one and half hours, followed by washing using 400 uL of 1×PBS, 0.1% tween20. The washing step was repeated three times to remove any excess biotinylation reagents. In a second step, the same antigen modified via conjugation to a hook oligo was added to the corresponding functionalized beads from the first step. The hook oligo was complementary to the anchor strand oligo and hybridized to it, resulting in the assembly of colocalized antigens. Each barcode and corresponding conjugate were incubated in separate tubes. Incubation in the second step was carried out at four degrees for ten hours, followed by washing using 400 uL of 1×PBS, 0.1% tween20. The washing step was repeated three times to remove any excess conjugates. The beads can be separately stored for use at a later time.

Example 2: Fabrication of pCLAMP Sensors for Multiplexed and Isotype Specific Detection of Sars-CoV-2 Antibodies In some embodiments, posterior co-localization by linkage assays microparticle (pCLAMP) assays can be fabricated to measure specific antibodies from a specific immunoglobulin class in multiplexed format. In the first step, streptavidin beads were co-coupled with biotinylated anchor oligos (anchor 1 and anchor 2) modified with different dyes to yield a distinguishable barcode. Two types of anchor strands were used here: Anchor 1 was complementary to the Hook Oligo conjugated to antigens and Anchor 2 was complementary to the Posterior Oligo conjugated to a secondary antibody targeting one immunoglobulin class, such as IgG, IgM and IgA. Anchor 1 and anchor 2 sequence can be contained in one or more oligo. Each barcode and antigen were fabricated in a separate tube. Each barcode, and antigen, were incubated in separate tubes at room temperature for 1.5 hours, followed by washing using 400 uL of 1×PBS, 0.1% tween20. The washing step was repeated three times to remove any excess biotinylation reagents. In a second step, the antigen conjugated to a hook oligo was added to the functionalized beads from the first step. The hook strand oligo was complementary to anchor 1 and hybridized to it, resulting in the assembly of antigen specific beads. Each barcode and corresponding conjugate were incubated in separate tubes. Incubation in the second step was carried out at four degrees for ten hours, followed by washing using 400 uL of 1×PBS, 0.1% tween20. The washing step was repeated three times to remove any excess conjugates. The beads can be separately stored for use at a later time.

Figure 11:
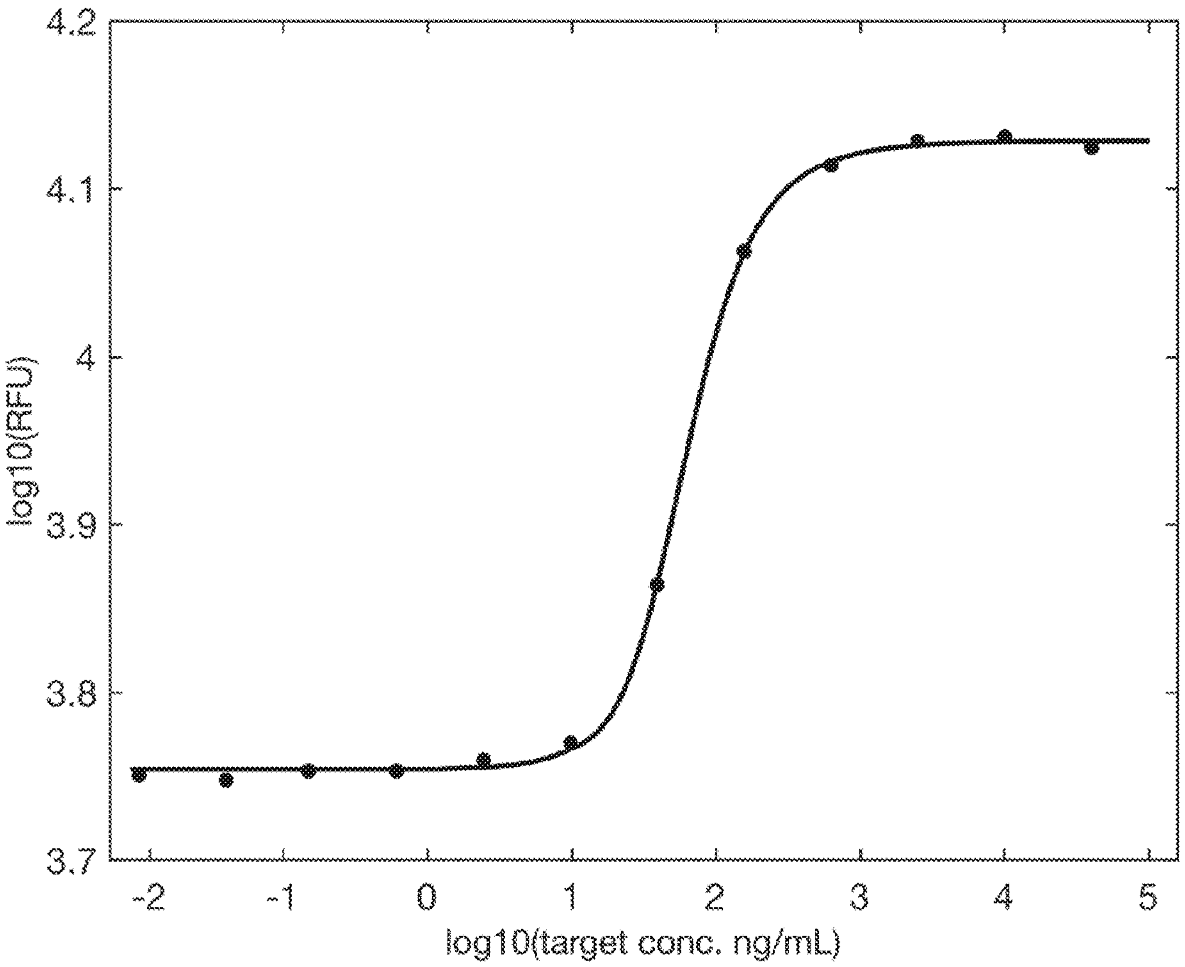
FIG. 11 shows the binding curve generated for a pCLAMP.

Example 3: Multiplexed and Iso-Type Specific Detection of SARS-CoV-2 Antibodies Using pCLAMP In a pCLAMP assay for SARS-CoV-2 antibodies, in some embodiments, 3 versions of anchor 2 (e.g. the DNA strand 'IMO-IgG' for anchoring IgG), each of which is specific for the hook element of an immunoglobulin-classifying antibody-DNA conjugate, were introduced on the surface of 3 different barcoded magnetic bead sets (fabricated using e.g. the strands 'pCLAMP-CO', 'pCLAMP-SO', and 'pCLAMP-BO'), alongside a hook oligo (e.g. the DNA strand 'pCLAMP-HO') conjugated to the SARS-CoV-2 Spike(S) protein (in this embodiment), thereby generating three different pCLAMP beads that can be combined afterwards. 25 uL of the combined magnetic beads were blocked and then incubated with 25 uL of plasma or serum samples, thereby enabling patient IgGs, IgMs, and/or IgAs to bind to the Spike antigen conjugated to the hook element on each barcode. The plate was incubated on an orbital plate shaker at 950 rpm for 3 hours at room temperature, followed by washing with 100 uL of 1×PBS, 0.1% Tween 20. The washing step was repeated three times. The beads were reconstituted into 30 uL of washing buffer after the washing steps. DNA-conjugated anti-human IgG (e.g. the DNA strand 'O-IgG'), DNA-conjugated anti-human IgM, and DNA-conjugated anti-human IgA antibodies were fabricated, each of which is conjugated to an oligonucleotide that is specific to one of the 3 versions of anchor 2 used in this embodiment. A 30 uL mixture of DNA-conjugated anti-human IgG, DNA-conjugated anti-human IgM and DNA-conjugated anti-human IgA was added to the beads for 2 hours with incubation at 950 rpm at room temperature, resulting in sandwich structures formed between the spike antigen, the SARS-CoV-2 specific IgG/IgM/IgAs patient antibodies, and the DNA-conjugated anti-human antibodies. Additionally, the DNA-conjugated anti-human antibodies hybridized to the corresponding anchor 2 elements on each microparticle. Each well was then washed 3 times with 100 uL of 1×PBS, 0.1% tween 20 and reconstituted into 30 uL after washing. 30 uL displacer oligo (DO) conjugated to Cy5 was then added (e.g. the DNA strand 'pCLAMP-DO'), followed by 30 min incubation on a plate shaker at 950 rpm at room temperature. As a result, the hook oligo which originally hybridized to the capture oligo were displaced from the surface and hybridized to DO-Cy5 oligo, yet remained bound to the beads through the SARS-CoV-2 specific IgG/IgM/IgAs patient antibodies and the anchor 2-hybridized DNA-conjugated anti-human IgG, DNA-conjugated anti-human IgM, and DNA-conjugated anti-human IgA antibodies. After displacement, 1×PBS, 0.1% tween 20 was used to wash the plate for 3 times before the cytometry readout. The resulting cytometry readout generated a standard binding curve with near zero background signal (FIG. 11).

The detection binders are releasably and flexibly linked to said support using a detachable linker called Hook Oligo that binds to a surface-bound Anchor oligo. importantly, neither the Hook Oligo nor the DB are detectably labeled. After contacting with the sample, analyte detection proceeds with the principle of release-dependent transduction (RDT), which relies on simultaneous labeling and displacement and of the hook oligo. The simultaneous labeling and displacement of HO is key to achieving a low-background detection whereby signal generation is codependent on the release of the detection binder and on the binding of the analyte to both a detection and a capture binder. In RDT, a positive signal occurs if and only if both of the following conditions are satisfied: (i) formation of a tertiary CB-analyte-DB complex, and (ii) release of the corresponding DB and/or hook strand from the anchor strand. Importantly, a non-released detection AB and/or hook strand will not contribute to the background signal While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 4: Poly-CLAMP Analysis Multiple Analytes in a Sample

Figure 12:
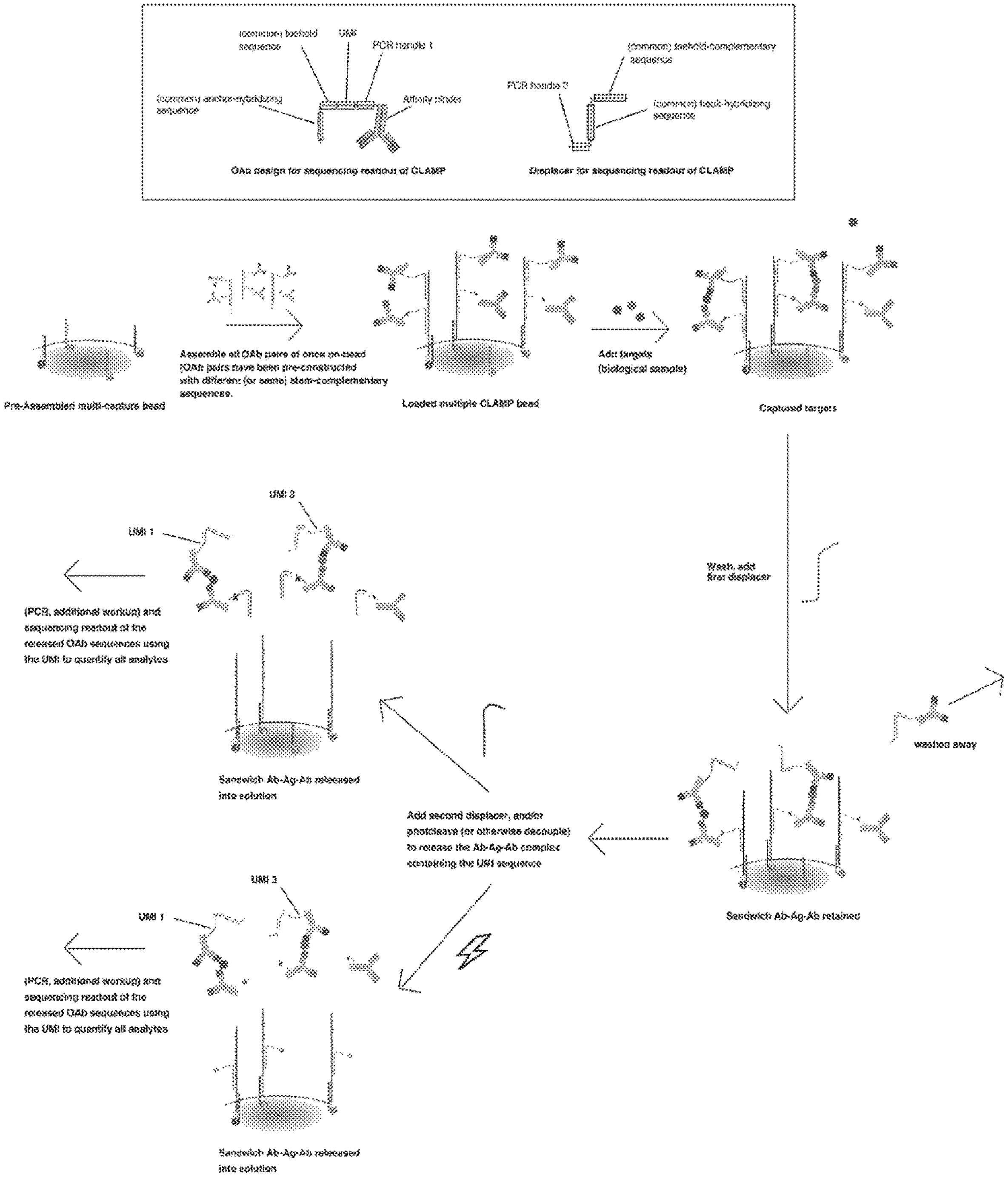
FIG. 12 shows a schematic of polyCLAMP for the detection of multiple analytes.

Exemplifying the compositions and methods described herein, FIG. 12 demonstrates a poly colocalization-by-linkage assay composition wherein a microparticle support comprises (1) a first detection and a first capture reagent, and (2) a second detection and a second capture reagent, and (3) a third detection and a third capture reagent. Each set of detection and capture reagents comprise a hook oligonucleotide comprising, in addition to the functional sequence, a barcode sequence comprising a unique molecular identifier (UMI), PCR primer site, a toe-hold sequence, and/or an anchor-hybridizing sequence. Each set of detection and capture reagents is specific for a different analyte yet they are coupled with a single microparticle support. In one embodiment, the poly-CLAMP beads can be assembled via hybridizing already pre-hybridized sets of detection and capture reagents, which were assembled through hybridization in solution with their respective anchor strands in a 1:1:1 stoichiometric ratio in PBS+300 mM NaCl+0.1% Tween20. Poly-CLAMP beads can also be assembled by hybridizing the pre-assembled multi-capture bead support with all of the capture and detection reagents at once in PBS+300 mM NaCl+0.1% Tween20, followed by washing. After assembly, the poly-CLAMP beads can be incubated with a sample comprising a plurality of analytes, such that a first complex between a first analyte and the first detection and first capture reagent is generated, and a second complex between a second analyte and the second detection and second capture reagent is generated. A plurality of detectable detection displacer reagents is then provided wherein the plurality comprises a first, second, and third detectable detection displacer that specifically binds the first, second, and third detector hook element, respectively, displacing each detection hook element from its anchoring element. In some embodiments, there is only 1 detectable detector displacer reagent and it is designed to bind to a common hook element shared across the 3 detection reagents. Any unbound detection reagent (e.g. the third detection reagent in FIG. 12) is displaced from the detection complex and removed by washing. A plurality of capture displacer reagents is then provided wherein the plurality comprises a first, second, and third capture displacer that specifically binds the first, second, and third capture hook element, respectively, displacing each capture hook element from its anchoring element. In some embodiments, there is only 1 capture displacer reagent and it is designed to bind to a common hook element shared across the 3 capture reagents.

Released detection hook elements (or other portions of the released complex) can then be processed and sequenced to identify the detection reagent and analyte. In some embodiments, the capture reagent can be displaced using a displacer oligo or cleaved through a chemical or enzymatic reaction. In some embodiments, a support-indexed anchor sequence is also displaced during the workflow and can be analyzed (see for example FIG. 3)

In some embodiments, the Poly-CLAMP is interfaced with a partition comprising cells, a single cell, cell supernatants, a single cell supernatant, cell lysates, a single cell lysate, or a biological sample. After sample incubation, the partitions can be pooled and combined with other partitions and further barcoded during the Poly-CLAMP assay, wherein the barcode sequences corresponding to the hook oligos and/or displacer oligos and/or support-indexed anchor oligo can be identified and used to identify an analyte and/or a sample as coming from a particular partition.

Example 5: Poly-CLAMP Analysis Multiple Epitope Analysis in a Sample

Figure 13:
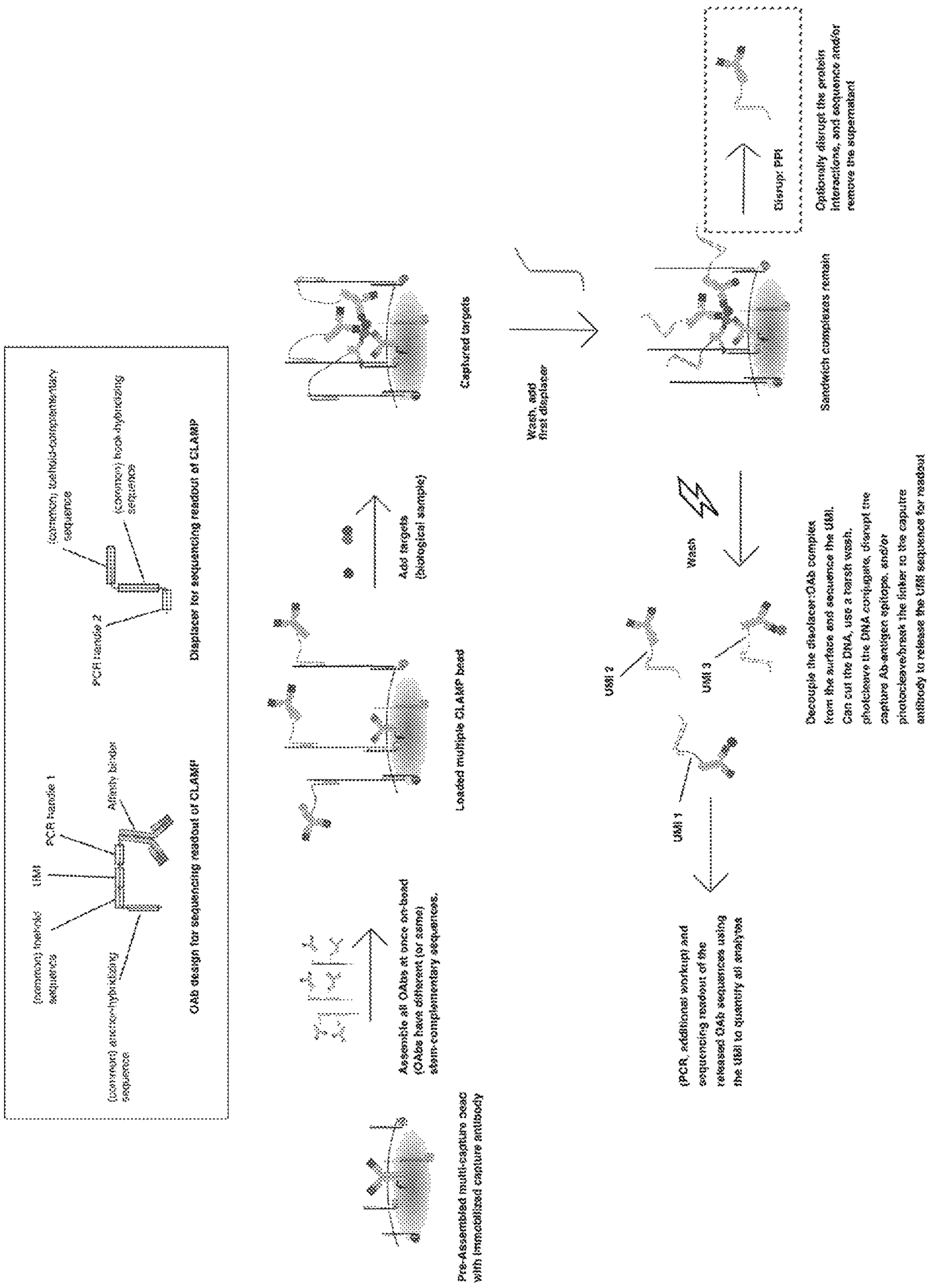
FIG. 13 shows a schematic of PTM-polyCLAMP for multiplexed epitope analysis of analytes.
Figure 14:
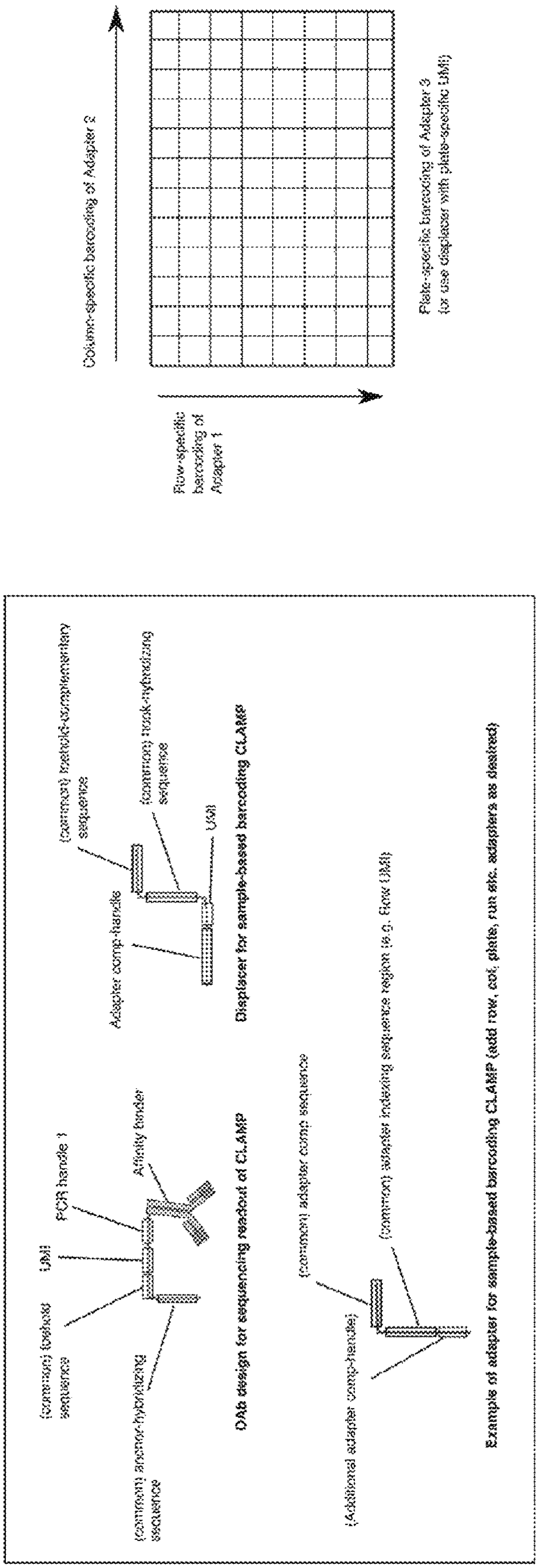
FIG. 14 shows a schematic of oligos comprising functional sequences and barcodes for the detection of analytes and schemes for partitioning a sample or samples.

Exemplifying the compositions and methods described herein, FIG. 13 demonstrates a colocalization-by-linkage assay composition wherein a microparticle support comprises a capture reagent and (1) a first detection reagent (2) a second detection reagent, and (3) a third detection reagent. Each detection reagent comprises a hook oligonucleotide comprising, in addition to the functional sequence, a barcode sequence comprising a unique molecular identifier (UMI), a PCR primer site, a toe-hold sequence, and/or an anchor-hybridizing sequence. Each detection reagent can be specific for a different analyte yet they are coupled with a single microparticle support. After incubation of the poly-CLAMP with a sample comprising a plurality of analytes, a first complex between a first analyte and the first detection reagent, the second detection reagent, the third detection reagent, and the capture reagent is generated. A plurality of displacer reagents is provided wherein the plurality comprises a first, second, and third detectable displacer that specifically binds the first, second, and third hook element, respectively, displacing each hook element from its anchoring element. In some embodiments, the displacer reagent is designed so that a single displacer oligonucleotide is capable of displacing all of the detection hook elements from the anchoring elements, for example using a conserved sequence across all detection hook elements. Any unbound detection reagents are displaced from the detection complex and removed via washing away. At this point, a perturbagen or other perturbing reagent can be added to interrogate whether e.g. any protein-protein interactions are disrupted in the analyte complex bound to the support. The hook elements and/or displacer reagents for any detection reagents that are removed from the support-bound analyte complex by the perturbing reagent (e.g. arising from a disrupted protein-protein interaction (PPI), see FIG. 13) can then be processed and sequenced or analyzed by qPCR or collector beads to identify the detection reagent(s) and analyte(s), and/or washed away from the support. A capture displacer agent is then provided, consisting of a UV light source in FIG. 13 which serves to cleave the photocleavable linker attaching the capture reagent to the support complex. Released detection hook elements (or other portions of the released complex) can then be processed and sequenced to identify the detection reagent and analyte. In some embodiments, the capture reagent can be displaced using a displacer oligo or cleaved through a chemical or enzymatic reaction.

In some embodiments, a support-indexed anchor sequence is also displaced during the workflow and can be analyzed (see for example FIG. 3). Optionally the detection hook element can be cleaved from the detection reagent prior to further processing and readout.

Example 6: Barcoding of Microparticles with Re-Partitioning for Multiplexed Readout Exemplifying the compositions and methods described herein, a plurality of microparticle supports containing capture and/or detector reagents (such as CLAMPs, capture antibodies, or a DNA sequence), each of which is optically decodable (stage 1 barcoding) are fabricated. The microparticle supports also contain additional single-stranded or partially single-stranded DNA sequences capable of hybridizing various barcoding strands used for stage 2 barcoding and stage 3 barcoding.

After each microparticle is fabricated, the plurality of microparticles can be pooled into as little as one partition, mixed, and then re-arrayed into multiple partitions, such as wells of a microtiter plate. Through this process each partition can contain a subset, or the entire plurality of microparticles.

Next, each partition can be interfaced with a sample containing unknown levels of the analyte(s) of interest. In addition, the wells can be barcoded through the addition of various ratiometric amounts of non-fluorescently-labeled and fluorescently-labeled barcoding strands, which can include fluorescently-labeled barcoding strands of multiple colors. Hybridization of these barcoding strands causes the microparticles in each partition to have different optically decodable stage 2 barcodes.

After a first washing step, the microparticles can be pooled into one partition and further analyzed (for example following the displacement protocol for a CLA assay). Here, the stage 2 barcode enables the identification of the sample corresponding to the microparticle, whereas the stage 1 barcode enables the identification of the initial microparticle components, i.e. the analyte measured.

Optionally, after the first washing step, the microparticles can again be pooled into one partition, mixed, and then re-arrayed into multiple partitions, such as wells of a microtiter plate. Through this process each partition can contain a subset, or the entire plurality of microparticles.

Each partition can then be interfaced with an additional reagent, such as a detection antibody, which optionally can be detectably labeled. Optionally, additional non-fluorescently-labeled and fluorescently-labeled barcoding strands can be added that barcode the microparticles in each partition based on the stage 3 barcode. In one embodiment, the additional reagent can consist of a DNA-conjugated antibody configured for a pCLAMP assay.

After a second washing step, the microparticles can be pooled into one partition and further analyzed (for example following the displacement protocol for a CLA assay of pCLAMP assay, and/or the second displacement or photo-release step of an addCLAMP assay). Here, the stage 3 barcode enables the identification of the additional reagent added, such as the detection antibody. In the case of a detectably labeled additional reagent added, the stage 3 barcode would enable the identification of the reagent generating the assay signal. As above, the stage 2 barcode enables the identification of the sample corresponding to the microparticle, whereas the stage 1 barcode enables the identification of the initial microparticle components.

Whereas optically decodable barcodes have been described, those skilled in the art will also recognize that DNA sequences capable of being ligated or otherwise coupled into a single DNA sequence would make the barcoding approach described here amenable to DNA-based readout of the final pool of microparticles following the CLA, pCLAMP, addCLAMP, and/or polyCLAMP assays described herein.

Example 7: Cy5-DO Readout of 1-Plex addCLAMP for Human GM-CSF

In some embodiments, a capture binder (cAB) conjugated to a UV-sensitive photocleavable biotin PEG linker and specific for human GM-CSF was introduced to a streptavidin-coated bead surface alongside biotinylated anchor and barcoding DNA strands, thereby creating barcoded microspheres containing an anchor oligo (e.g. DNA strand 'Capture-1' hybridized also with e.g. DNA strand 'Anchor-1') and a capture antibody. A releasable detection binder (dAB) conjugated to a hook oligo (e.g. DNA strand 'Hook-1_1') and specific for human GM-CSF was then hybridized to the anchor oligo on the bead surface. 20,000 GM-CSF-specific addCLAMP beads were blocked with 1% BSA for 1 hr, washed in 1×PBS, 0.1% Tween-20, and aliquoted into wells of a 96-well polypropylene plate. Each well of beads was incubated with known concentrations of recombinant human GM-CSF antigen in 1×PBS, resulting in sandwich structures formed between the antigen and both the capture antibody and the detection antibody. The plate was incubated on an orbital plate shaker at 950 rpm for 2 hours at room temperature, followed by washing with 1×PBS, 0.1% Tween-20. The washing step was repeated 3 times. The beads were reconstituted into 50 μL displacing buffer (1×PBS, 900 mM NaCl). An equal volume of displacing oligo (DO) conjugated to Cy5 (e.g. DNA strand 'DO-1_1_Cy5') in displacing buffer was added, followed by incubation on an orbital shaker at 950 rpm for 30 minutes at room temperature. As a result, the hook oligo which originally hybridized to the capture oligo was displaced from the surface and was hybridized to the DO-Cy5 oligo. After displacement, the plate was washed 4 times.

Figure 6:
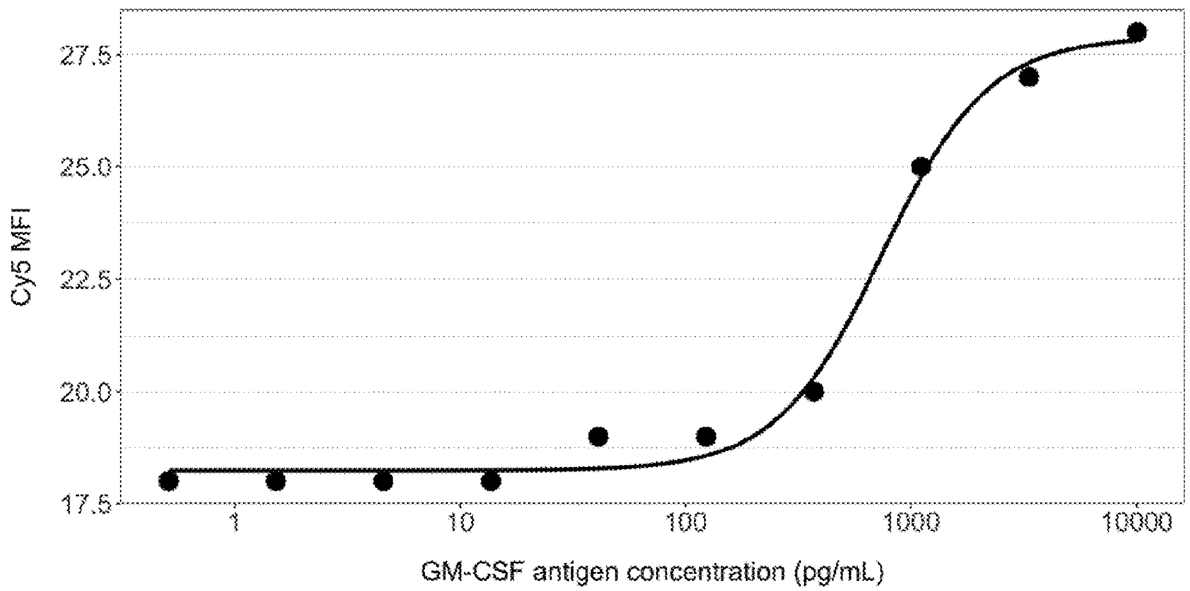
FIG. 6 shows the binding curves generated for a GM-CSF-specific addCLAMP based on readout of a Cy5-labeled detection displacer oligonucleotide on collector beads that hybridize to the detection hook oligonucleotide.

The plate was then irradiated with 365 nm UV light for 30 minutes at room temperature. As a result, cAB was released from the bead surface through photocleavage of its UV-sensitive biotin linker. Supernatants containing the released sandwich structures were isolated from the solid state beads and introduced into a new plate. 1000 collector beads were added to each well containing the released sandwich structures. The collector beads were designed with a surface containing an oligonucleotide (e.g. DNA strand 'Anchor_BHR-1_1') that is the reverse complement of a portion of the dAB hook oligo in a differing region from the DO-Cy5 oligo. Supernatants were incubated with collector beads for 3 hours, on an orbital plate shaker at 950 rpm at room temperature. As a result, sandwich structures were captured onto the bead surface. After capture, the collector beads were washed 3 times with washing buffer before cytometry readout of hybridized Cy5-DO, which generated a standard binding curve with near zero background signal (FIG. 6).

Example 8: BV-GAM Readout of 1-Plex addCLAMP for Human GM-CSF

In some embodiments, a capture binder (cAB) conjugated to a UV-sensitive photocleavable biotin PEG linker and specific for human GM-CSF was introduced to a streptavidin-coated bead surface alongside biotinylated anchor (e.g. DNA strand 'Capture-1' hybridized also with e.g. DNA strand 'Anchor-1') and barcoding DNA strands, thereby creating barcoded microspheres containing an anchor oligo and a capture antibody. A releasable detection binder (dAB) conjugated to a hook oligo (e.g. DNA strand 'Hook-1_1') and specific for human GM-CSF was then hybridized to the anchor oligo on the bead surface. 20,000 GM-CSF-specific addCLAMP beads were blocked with 1% BSA for 1 hr, washed in 1×PBS, 0.1% Tween-20, and aliquoted into wells of a 96-well polypropylene plate. Each well of beads was incubated with known concentrations of recombinant human GM-CSF antigen in 1×PBS, resulting in sandwich structures formed between the antigen and both the capture antibody and the detection antibody. The plate was incubated on an orbital plate shaker at 950 rpm for 2 hours at room temperature, followed by washing with 1×PBS, 0.1% Tween-20. The washing step was repeated 3 times. The beads were reconstituted into 50 μL displacing buffer (1×PBS, 900 mM NaCl). An equal volume of displacing oligo (DO) (e.g. DNA strand 'DO-1_1') in displacing buffer was added, followed by incubation on an orbital shaker at 950 rpm for 30 minutes at room temperature. As a result, the hook oligo which originally hybridized to the capture oligo was displaced from the surface and was hybridized to the DO oligo. After displacement, the plate was washed 4 times.

The plate was then irradiated with 365 nm UV light for 30 minutes at room temperature. As a result, cAB was released from the bead surface through photocleavage of its UV-sensitive biotin linker. Supernatants containing the released sandwich structures were isolated from the solid state beads and introduced into a new plate. 1000 collector beads were added to each well containing the released sandwich structures. The collector beads were designed with a surface containing an oligonucleotide (e.g. DNA strand 'Anchor_BHR-1_1') that is the reverse complement of a portion of the dAB hook oligo in a differing region from the DO oligo. Supernatants were incubated with collector beads for 3 hours, on an orbital plate shaker at 950 rpm at room temperature. As a result, sandwich structures were captured onto the bead surface. After capture, the collector beads were washed 3 times with washing buffer.

Figure 7:
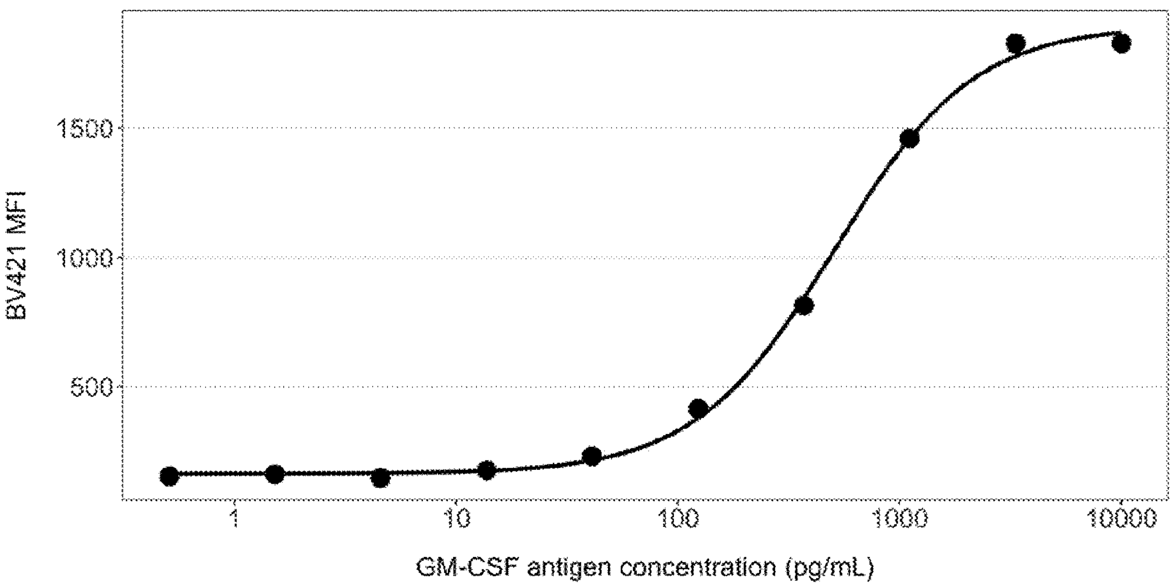
FIG. 7 shows the binding curves generated for a GM-CSF-specific addCLAMP based on readout of a BV-421-labeled anti-mouse antibody used to label sandwich complexes bound to collector beads that hybridize to the detection hook oligonucleotide.

The beads were then exchanged into 30 μL 1×PBS 0.05% Tween-20, 300 mM NaCl. An equal volume of anti-mouse IgG secondary antibody conjugated to BV421 dye was incubated with the collector beads. The incubation plate was kept on an orbital shaker at 950 rpm for 30 minutes at room temperature. As a result mouse-derived dAB was bound by anti-mouse IgG antibody labelled with BV421. After staining, the incubation plate was washed 3 times before cytometry readout of bound secondary antibody-BV421, which generated a standard binding curve with low background signal (FIG. 7).

Example 9: QPCR Readout of 1-Plex addCLAMP for Human GM-CSF

In some embodiments, a capture binder (cAB) conjugated to a UV-sensitive photocleavable biotin PEG linker and specific for human GM-CSF was introduced to a streptavidin-coated bead surface alongside biotinylated DNA strands, thereby creating barcoded microspheres containing an anchor oligo (e.g. DNA strand 'Capture-1' hybridized also with e.g. DNA strand 'Anchor-1') and a capture antibody. A releasable detection binder (dAB) conjugated to a hook oligo (e.g. DNA strand 'Hook-1_1') and specific for human GM-CSF was then hybridized to the anchor oligo on the bead surface. 20,000 GM-CSF-specific addCLAMP beads were blocked with 1% BSA for 1 hr, washed in 1×PBS, 0.1% Tween-20, and aliquoted into wells of a 96-well polypropylene plate. Each well of beads was incubated with known concentrations of recombinant human GM-CSF antigen in 1×PBS, resulting in sandwich structures formed between the antigen and both the capture antibody and the detection antibody. The plate was incubated on an orbital plate shaker at 950 rpm for 2 hours at room temperature, followed by washing with 1×PBS, 0.1% Tween-20. The washing step was repeated 3 times. The beads were reconstituted into 50 μL displacing buffer (1×PBS, 900 mM NaCl). An equal volume of displacing oligo (DO) (e.g. DNA strand 'DO-1_1') in displacing buffer was added, followed by incubation on an orbital shaker at 950 rpm for 30 minutes at room temperature. As a result, the hook oligo which originally hybridized to the capture oligo was displaced from the surface and was hybridized to the DO oligo. After displacement, the plate was washed 4 times.

Figure 8:
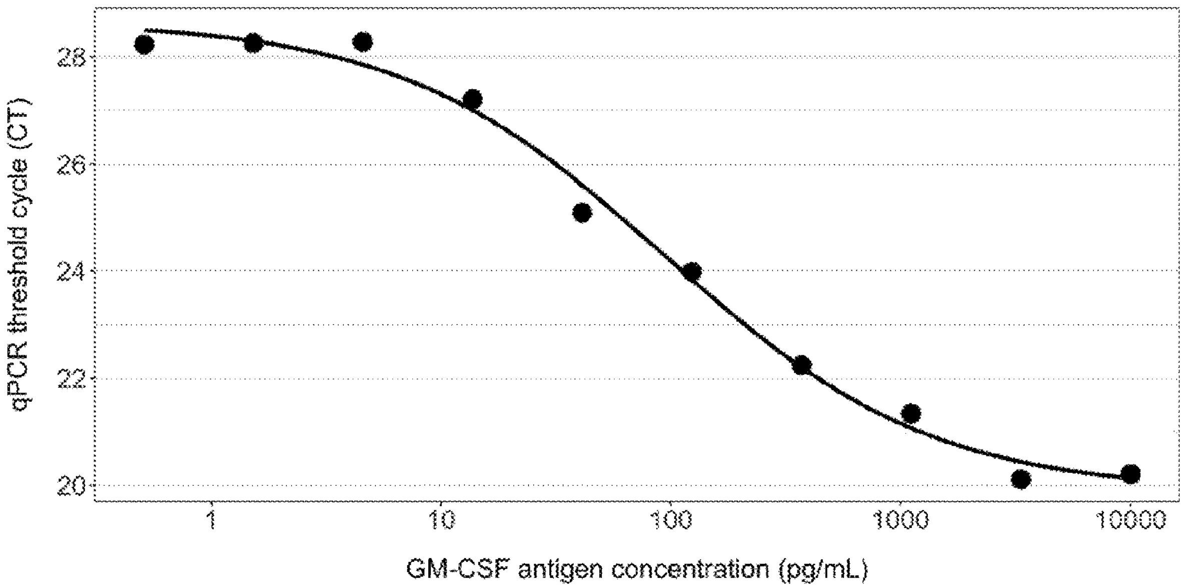
FIG. 8 shows the binding curves generated for a GM-CSF-specific addCLAMP based on qPCR readout of released sandwich complexes after sample incubation, washing, displacement of detection reagent hook oligonucleotides, washing, and UV cleavage and release of the capture antibody from the support.
Figure 9:
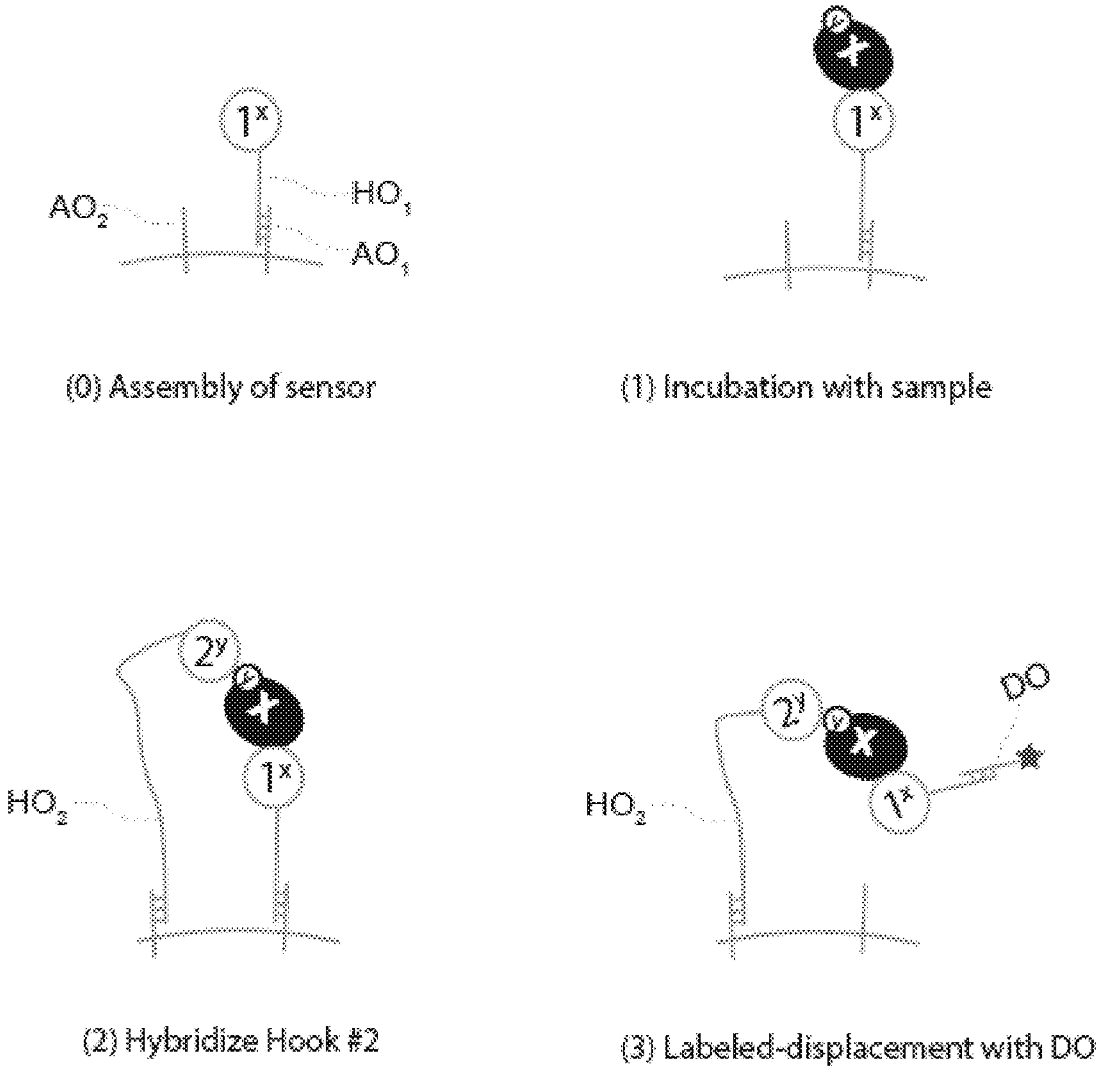
FIG. 9 shows a schematic of the posterior co-localization by linkage assays microparticle (pCLAMP) method for the detection of an analyte X with a common epitope Y.
Figure 10:
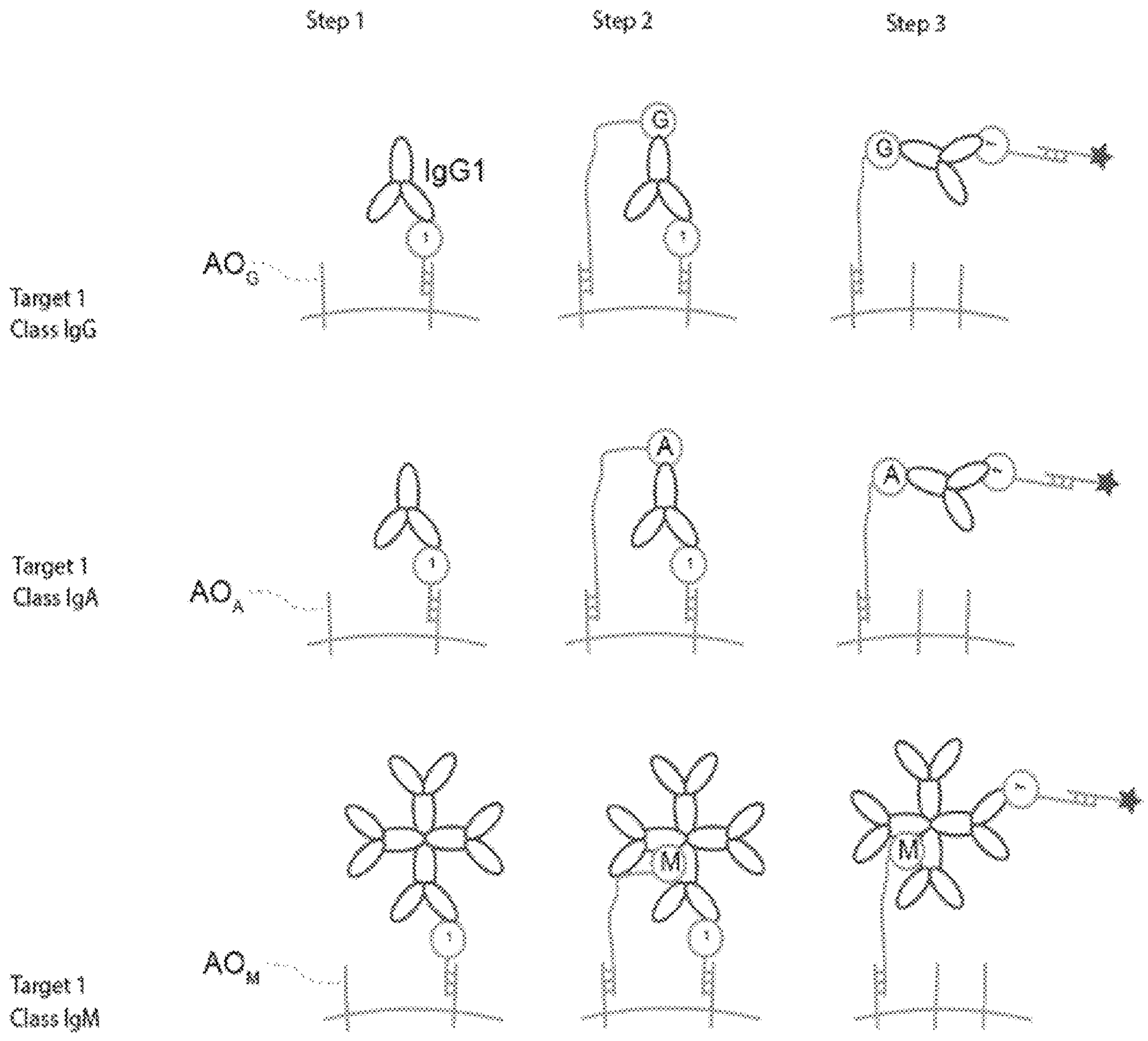
FIG. 10 shows a schematic of the posterior co-localization by linkage assays microparticle (pCLAMP) method for the multiplexed detection of iso-type specific and antigen-specific antibodies.

The plate was then irradiated with 365 nm UV light for 30 minutes at room temperature. As a result, cAB was released from the bead surface through photocleavage of its UV-sensitive biotin linker. Supernatant containing released sandwich structures was isolated from solid state beads, and diluted 5-fold in nuclease-free water. Diluted samples were combined with 1× PowerTrack SYBR Green quantitative polymerase chain reaction (qPCR) mastermix, and 100 nM forward and reverse primers (e.g. DNA strand 'Primer-1_1-For' and DNA strand 'PrNorm-Uni-Rev') specific to the detection antibody hook oligo. A total volume of 10 μL of prepared samples were run on a real-time PCR thermocycler for 40 denature-anneal-extension cycles to amplify hook oligo product using a melting temperature of 95° C. and an annealing temperature of 50° C. Optionally, primers with added 5' flaps (e.g. DNA strand 'PrLnTa-1_1-For' and DNA strand 'PrLnTa-Uni-Rev') can be used to increase the signal: background ratio of the qpCR assay. Fluorescence was detected during each qPCR cycle, and the calculated threshold cycle (CT) values were used to generate a standard curve for the GM-CSF antigen with high sensitivity (<10 pg/mL) (FIG. 8).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein can be employed in practicing the disclosure. It is intended that the following claims define the scope of the disclosure and that methods and structures within the scope of these claims and their equivalents be covered thereby.

SEQUENCES

| SEQ ID NO | SEQUENCE | NOTE |
|---|---|---|
| 1 | /5Biosg/TTTTTTTTTGTGGCGGCGGTGGCCTGTATCTGTGCT TGCCTG | IMO-IgG |
| 2 | /5ThioMC6-D/TTTTTTTTTTCAGGCAAGCACAGATACAGGC | 0-IgG |
| 3 | /5Biosg/TTTTTTTTTGTGGCGGCGGTGATTGGTTATTGAGAG TTTATG | pCLAMP-CO |
| 4 | /5Biosg/TTTTTTTTTGTGGCGGCGGTG | pCLAMP-SO |
| 5 | CACCGCCGCCACAAAAAAAAA/3Cy3SP/ | pCLAMP-BO |
| 6 | /5ThioMC6-D/TTTTTTACTTTTCAACCACCACTCAACCATATTCAAAGCTTA CGATGCCGACTCATTCGCCATAAACTCTCAATAACCAAT | pCLAMP-HO |
| 7 | /5Cy5/AGAGGTTTAATAGTGTATAGATTGGTTATTGAGAGTT TATGGCGAATGAG | pCLAMP-DO: |
| 8 | /5Biosg/TTTTTTTTTGTGGCGGCGGTGGTGGTTGGTGGTGG TAGGTGG | Capture-1 |
| 9 | /5Biosg/TTTTTTTTTGTGGCGGCGGTGAGGTGGAGAGGAGA AGGAGGT | Capture-2 |
| 10 | ACTATCATTACATCTAACAACTTTTTACTCTCTACACAAACTAT CTCTTTTTCCACCTACCACCACCAACCAC | Anchor-1 |
| 11 | CTATTACTTATACATCAATCTTTTTTCAATCTAATCATCATTCA CACTTTTTACCTCCTTCTCCTCTCCACCT | Anchor-2 |
| 12 | GTTGTTAGATGTAATGATAGTTGTTGTTGATTTTTGTATTTGT TTGTATTTGCAAGTTAAAAGATCTTTTGAAGTTTTTTT/3ThioMC3-D/ | Hook-1_1 |
| 13 | GAGATAGTTTGTGTAGAGAGTAGTAAGTAGTTTTTTTTTT/3ThioMC3-D/ | Hook-1_2 |
| 14 | AGATTGATGTATAAGTAATAGTGTGGTGTATTTTTGTATTTG TTTGTATTTGCAAGTTAAAAGATCTTTTGAAGTTTTTTT/3ThioMC3-D/ | Hook-2_1 |

-continued

| SEQUENCES | | |
|---|---|---|
| SEQ ID NO | SEQUENCE | NOTE |
| 15 | GTGTGAATGATGATTAGATTGGAAAGTGAGTTTTTTTTTT/3ThioMC3-D/ | Hook-2_2 |
| 16 | 5Cy5/TCAACAACAACTATCATTACATCTAACAAC | DO-1_1_Cy5 |
| 17 | TCAACAACAACTATCATTACATCTAACAAC | DO-1_1 |
| 18 | CTACTTACTACTCTCTACACAAACTATCTC | DO-1_2 |
| 19 | TACACCACACTATTACTTATACATCAATCT | DO-2_1 |
| 20 | CTCACTTTCCAATCTAATCATCATTCACAC | DO-2_2 |
| 21 | GTTGTTAGATGTAATGATAGTTGTTG | Primer-1_1-For |
| 22 | AGATTGATGTATAAGTAATAGTGTGG | Primer-2_1-For |
| 23 | /56-FAM/TTGAGATAGTTTGTGT | QC_FAM-Anchor-1 |
| 24 | /56-FAM/TTGTGTGAATGATGAT | QC_FAM-Anchor-2 |
| 25 | /56-FAM/AAAAATCAACAACA | QC_FAM-OAb-1_1 |
| 26 | /56-FAM/AAAAACTACTTACT | QC_FAM-OAb-1_2 |
| 27 | /56-FAM/AAAAATACACCACA | QC_FAM-OAb-2_1 |
| 28 | /56-FAM/AAAAACTCACTTTC | QC_FAM-OAb-2_2 |
| 29 | ACTATCATTACATCTAACAACTTTTTCCACCTACCACCACCAACCAC | Anchor-1_1-Only |
| 30 | ACTCTCTACACAAACTATCTCTTTTTCCACCTACCACCACCAACCAC | Anchor-1_2-Only |
| 31 | CTATTACTTATACATCAATCTTTTTTACCTCCTTCTCCTCTCCACCT | Anchor-2_1-Only |
| 32 | CAATCTAATCATCATTCACACTTTTTACCTCCTTCTCCTCTCCACCT | Anchor-2_2-Only |
| 33 | GAGATAGTTTGTGTAGAGAGTAGTAAGTAGTTTTT/iSpPC/TTTTT/3ThioMC3-D/ | PhoClv-Hook-1_2 |
| 34 | GTGTGAATGATGATTAGATTGGAAAGTGAGTTTTT/iSpPC/TTTTT/3ThioMC3-D/ | PhoClv-Hook-2_2 |
| 35 | GTTGTTAGATGTAATGATAGTTGTTGTTGATTTTTGTATTTGTTTGTATTTGCAAGTTAAAAGATCTTTTGAAGTTTTTTT | qPCR_CTRL-1 |
| 36 | AGATTGATGTATAAGTAATAGTGTGGTGTATTTTTGTATTTGTTTGTATTTGCAAGTTAAAAGATCTTTTGAAGTTTTTTT | qPCR_CTRL-2 |
| 37 | /5ThioMC6-D/TTTTTTACTTTTCAACCACCACTCAACCATATTCAAAGCTTACGATGCCGACTCATTCGCCATAAACTCTCAATAACCAAT | Thiol-HO |
| 38 | TTTTTTACTTTTCAACCACCACTC | Primer-HO-For |
| 39 | ATTGGTTATTGAGAGTTTATGGCG | Primer-HO-Rev |
| 40 | AACTTCAAAAGATCTTTTAACTTGC | PrNorm-Uni-Rev |
| 41 | AAAAACAAAAACAAAAAAACTTCAAAAGATCTTTTAACTTGC | PrLnTa-Uni-Rev |
| 42 | TAAAACAAAATCGTTGTTAGATGTAATGATAGTTGTTG | PrLnTa-1_1-For |
| 43 | TAAAACAAAATCAGATTGATGTATAAGTAATAGTGTGG | PrLnTa-2_1-For |
| 44 | AACTTCAAAAGATCTTTTAACTTGCAAATACTTTTTCCACCTACCACCACCAACCAC | Anchor_BHR-1_1 |

The invention claimed is:

1. A method of processing an analyte for the detection of the analyte, the method comprising:

(a) contacting a sample comprising the analyte with a microparticle comprising:

(i) a capture antibody releasably coupled to the microparticle via a releasable linker, wherein the capture antibody binds to the analyte; and (ii) a detection antibody releasably coupled to the microparticle via a releasable oligonucleotide, wherein the detection antibody binds to the analyte, and wherein the releasable oligonucleotide comprises a nucleic acid sequence, thereby generating an analyte bound complex comprising the analyte bound to both the capture antibody and the detection antibody;

(b) providing a displacer oligonucleotide configured to hybridize to the releasable oligonucleotide and decouple the releasable oligonucleotide from the microparticle, thereby decoupling the releasable oligonucleotide from the microparticle and maintaining coupling of the releasable linker to the microparticle, thereby displacing the detection antibody from the microparticle;

(c) subsequent to (b), releasing the analyte bound complex in a solution by decoupling the releasable linker from the microparticle due at least in part to displacement of the capture antibody from the microparticle, wherein the analyte bound complex in the solution comprises the nucleic acid sequence; and (d) subsequent to (c), detecting the nucleic acid sequence in the solution to identify the analyte as being present in the analyte bound complex, wherein detecting comprises sequencing the nucleic acid sequence, performing a nucleic acid amplification reaction, or coupling the nucleic acid sequence to a labeled probe.

2. The method of claim 1, wherein (c), decoupling comprises providing a stimulus that decouples the capture antibody from the microparticle.

3. The method of claim 2, wherein the stimulus is photo-stimulus.

4. The method of claim 1, wherein the releasable linker comprises a labile bond.

5. The method of claim 1, wherein the releasable linker comprises an oligonucleotide.

6. The method of claim 1, wherein the releasable linker comprises a polyethylene glycol linker.

7. The method of claim 2, wherein the stimulus is a thermal stimulus, photo-stimulus, chemical stimulus, a mechanical stimulus, a radiation stimulus, a biological stimulus, or any combination thereof.

8. The method of claim 1, wherein the analyte is an antibody molecule.

9. The method of claim 1, wherein the analyte is an antigen, an antibody, an affimer, an aptamer, a modified aptamer, a somamer, an antibody fragment, a protein, a polypeptide, a multi-protein complex, an exosome, an oligonucleotide, a hormone, a modified oligonucleotide, or a low molecular weight compound.

10. The method of claim 1, wherein the detection antibody is a specific for an immunoglobulin.

11. The method of claim 10, wherein the immunoglobulin is specific for an immunoglobulin class IgG, IgM, IgA, IgD, or IgE.

12. The method of claim 1, wherein the detection antibody comprises a protein A, protein G, or protein M.

13. The method of claim 1, wherein the analyte is a protein comprising a posttranslational modification.

14. The method of claim 13, wherein the posttranslational modification comprises phosphorylation, glycosylation, ubiquitination, nitrosylation, methylation, acetylation, lipidation or proteolysis.

15. The method of claim 13, wherein the detection antibody is specific for the posttranslational modification or the protein comprising the posttranslational modification.

16. The method of claim 1, wherein the sample comprises a biological sample.

17. The method of claim 16, wherein the biological sample comprises a bodily fluid, an extract, a solution containing proteins and/or DNA, a cell extract, a cell lysate, a single cell lysate, or a tissue lysate.

18. The method of claim 1, wherein the displacer oligonucleotide is labeled with Cy3.

19. The method of claim 1, wherein the displacer oligonucleotide is labeled with Cy5.

20. The method of claim 1, wherein the nucleic acid amplification reaction comprises PCR.

* * * * *

SEQUENCE LISTING

<160> NUMBER OF SEQ ID NOS: 44

<210> SEQ ID NO 1
<211> LENGTH: 42
<212> TYPE: DNA
<213> ORGANISM: Artificial Sequence
<220> FEATURE:
<223> OTHER INFORMATION: Synthetic construct

<400> SEQUENCE: 1 ttttttttg tggcggcggt ggcctgtatc tgtgcttgcc tg 42

<210> SEQ ID NO 2
<211> LENGTH: 31
<212> TYPE: DNA
<213> ORGANISM: Artificial Sequence
<220> FEATURE:
<223> OTHER INFORMATION: Synthetic construct

<400> SEQUENCE: 2
tttttttttt caggcaagca cagatacagg c 31

<210> SEQ ID NO 3
<211> LENGTH: 42
<212> TYPE: DNA
<213> ORGANISM: Artificial Sequence
<220> FEATURE:
<223> OTHER INFORMATION: Synthetic construct

<400> SEQUENCE: 3 ttttttttg tggcggcggt gattggttat tgagagttta tg 42

<210> SEQ ID NO 4
<211> LENGTH: 21
<212> TYPE: DNA
<213> ORGANISM: Artificial Sequence
<220> FEATURE:
<223> OTHER INFORMATION: Synthetic construct

<400> SEQUENCE: 4 ttttttttg tggcggcggt g 21

<210> SEQ ID NO 5
<211> LENGTH: 21
<212> TYPE: DNA
<213> ORGANISM: Artificial Sequence
<220> FEATURE:
<223> OTHER INFORMATION: Synthetic construct

<400> SEQUENCE: 5
caccgccgcc acaaaaaaaa a 21

<210> SEQ ID NO 6
<211> LENGTH: 81
<212> TYPE: DNA
<213> ORGANISM: Artificial Sequence
<220> FEATURE:
<223> OTHER INFORMATION: Synthetic construct

<400> SEQUENCE: 6 tttttactt ttcaaccacc actcaaccat attcaaagct tacgatgccg actcattcgc 60
cataaactct caataaccaa t 81

<210> SEQ ID NO 7
<211> LENGTH: 50

<212> TYPE: DNA
<213> ORGANISM: Artificial Sequence
<220> FEATURE:
<223> OTHER INFORMATION: Synthetic construct

<400> SEQUENCE: 7
agaggtttaa tagtgtatag attggttatt gagagtttat ggcgaatgag 50

<210> SEQ ID NO 8
<211> LENGTH: 42
<212> TYPE: DNA
<213> ORGANISM: Artificial Sequence
<220> FEATURE:
<223> OTHER INFORMATION: Synthetic construct

<400> SEQUENCE: 8
tttttttttg tggcggcggt ggtggttggt ggtggtaggt gg 42

<210> SEQ ID NO 9
<211> LENGTH: 42
<212> TYPE: DNA
<213> ORGANISM: Artificial Sequence
<220> FEATURE:
<223> OTHER INFORMATION: Synthetic construct

<400> SEQUENCE: 9
tttttttttg tggcggcggt gaggtggaga ggagaaggag gt 42

<210> SEQ ID NO 10
<211> LENGTH: 73
<212> TYPE: DNA
<213> ORGANISM: Artificial Sequence
<220> FEATURE:
<223> OTHER INFORMATION: Synthetic construct

<400> SEQUENCE: 10
actatcatta catctaacaa ctttttactc tctacacaaa ctatctcttt ttccacctac 60
caccaccaac cac 73

<210> SEQ ID NO 11
<211> LENGTH: 73
<212> TYPE: DNA
<213> ORGANISM: Artificial Sequence
<220> FEATURE:
<223> OTHER INFORMATION: Synthetic construct

<400> SEQUENCE: 11
ctattactta tacatcaatc ttttttcaat ctaatcatca ttcacacttt ttacctcctt 60
ctcctctcca cct 73

<210> SEQ ID NO 12
<211> LENGTH: 84
<212> TYPE: DNA
<213> ORGANISM: Artificial Sequence
<220> FEATURE:
<223> OTHER INFORMATION: Synthetic construct

<400> SEQUENCE: 12
gttgttagat gtaatgatag ttgttgttga ttttttgtat ttgtttgtat ttgcaagtta 60
aaagatcttt ttgaagtttt tttt 84

<210> SEQ ID NO 13
<211> LENGTH: 40
<212> TYPE: DNA

<213> ORGANISM: Artificial Sequence
<220> FEATURE:
<223> OTHER INFORMATION: Synthetic construct

<400> SEQUENCE: 13
gagatagttt gtgtagagag tagtaagtag ttttttttt 40

<210> SEQ ID NO 14
<211> LENGTH: 82
<212> TYPE: DNA
<213> ORGANISM: Artificial Sequence
<220> FEATURE:
<223> OTHER INFORMATION: Synthetic construct

<400> SEQUENCE: 14
agattgatgt ataagtaata gtgtggtgta ttttttgtat ttgtttgtat ttgcaagtta 60
aaagatcttt tgaagttttt tt 82

<210> SEQ ID NO 15
<211> LENGTH: 40
<212> TYPE: DNA
<213> ORGANISM: Artificial Sequence
<220> FEATURE:
<223> OTHER INFORMATION: Synthetic construct

<400> SEQUENCE: 15
gtgtgaatga tgattagatt ggaaagtgag ttttttttt 40

<210> SEQ ID NO 16
<211> LENGTH: 30
<212> TYPE: DNA
<213> ORGANISM: Artificial Sequence
<220> FEATURE:
<223> OTHER INFORMATION: Synthetic construct

<400> SEQUENCE: 16
tcaacaacaa ctatcattac atctaacaac 30

<210> SEQ ID NO 17
<211> LENGTH: 30
<212> TYPE: DNA
<213> ORGANISM: Artificial Sequence
<220> FEATURE:
<223> OTHER INFORMATION: Synthetic construct

<400> SEQUENCE: 17
tcaacaacaa ctatcattac atctaacaac 30

<210> SEQ ID NO 18
<211> LENGTH: 30
<212> TYPE: DNA
<213> ORGANISM: Artificial Sequence
<220> FEATURE:
<223> OTHER INFORMATION: Synthetic construct

<400> SEQUENCE: 18
ctacttacta ctctctacac aaactatctc 30

<210> SEQ ID NO 19
<211> LENGTH: 30
<212> TYPE: DNA
<213> ORGANISM: Artificial Sequence
<220> FEATURE:
<223> OTHER INFORMATION: Synthetic construct

<400> SEQUENCE: 19
tacaccacac tattacttat acatcaatct 30

<210> SEQ ID NO 20
<211> LENGTH: 30
<212> TYPE: DNA
<213> ORGANISM: Artificial Sequence
<220> FEATURE:
<223> OTHER INFORMATION: Synthetic construct

<400> SEQUENCE: 20
ctcactttcc aatctaatca tcattcacac 30

<210> SEQ ID NO 21
<211> LENGTH: 26
<212> TYPE: DNA
<213> ORGANISM: Artificial Sequence
<220> FEATURE:
<223> OTHER INFORMATION: Synthetic construct

<400> SEQUENCE: 21
gttgttagat gtaatgatag ttgttg 26

<210> SEQ ID NO 22
<211> LENGTH: 26
<212> TYPE: DNA
<213> ORGANISM: Artificial Sequence
<220> FEATURE:
<223> OTHER INFORMATION: Synthetic construct

<400> SEQUENCE: 22
agattgatgt ataagtaata gtgtgg 26

<210> SEQ ID NO 23
<211> LENGTH: 15
<212> TYPE: DNA
<213> ORGANISM: Artificial Sequence
<220> FEATURE:
<223> OTHER INFORMATION: Synthetic construct

<400> SEQUENCE: 23
tgagatagtt tgtgt 15

<210> SEQ ID NO 24
<211> LENGTH: 15
<212> TYPE: DNA
<213> ORGANISM: Artificial Sequence
<220> FEATURE:
<223> OTHER INFORMATION: Synthetic construct

<400> SEQUENCE: 24
tgtgtgaatg atgat 15

<210> SEQ ID NO 25
<211> LENGTH: 14
<212> TYPE: DNA
<213> ORGANISM: Artificial Sequence
<220> FEATURE:
<223> OTHER INFORMATION: Synthetic construct

<400> SEQUENCE: 25
aaaaatcaac aaca 14

<210> SEQ ID NO 26

<211> LENGTH: 14
<212> TYPE: DNA
<213> ORGANISM: Artificial Sequence
<220> FEATURE:
<223> OTHER INFORMATION: Synthetic construct

<400> SEQUENCE: 26
aaaaactact tact 14

<210> SEQ ID NO 27
<211> LENGTH: 14
<212> TYPE: DNA
<213> ORGANISM: Artificial Sequence
<220> FEATURE:
<223> OTHER INFORMATION: Synthetic construct

<400> SEQUENCE: 27
aaaaatacac caca 14

<210> SEQ ID NO 28
<211> LENGTH: 14
<212> TYPE: DNA
<213> ORGANISM: Artificial Sequence
<220> FEATURE:
<223> OTHER INFORMATION: Synthetic construct

<400> SEQUENCE: 28
aaaaactcac tttc 14

<210> SEQ ID NO 29
<211> LENGTH: 47
<212> TYPE: DNA
<213> ORGANISM: Artificial Sequence
<220> FEATURE:
<223> OTHER INFORMATION: Synthetic construct

<400> SEQUENCE: 29
actatcatta catctaacaa ctttttccac ctaccaccac caaccac 47

<210> SEQ ID NO 30
<211> LENGTH: 47
<212> TYPE: DNA
<213> ORGANISM: Artificial Sequence
<220> FEATURE:
<223> OTHER INFORMATION: Synthetic construct

<400> SEQUENCE: 30
actctctaca caaactatct ctttttccac ctaccaccac caaccac 47

<210> SEQ ID NO 31
<211> LENGTH: 47
<212> TYPE: DNA
<213> ORGANISM: Artificial Sequence
<220> FEATURE:
<223> OTHER INFORMATION: Synthetic construct

<400> SEQUENCE: 31
ctattactta tacatcaatc ttttttacct ccttctcctc tccacct 47

<210> SEQ ID NO 32
<211> LENGTH: 47
<212> TYPE: DNA
<213> ORGANISM: Artificial Sequence
<220> FEATURE:
<223> OTHER INFORMATION: Synthetic construct

<400> SEQUENCE: 32
caatctaatc atcattcaca ctttttacct ccttctcctc tccacct 47

<210> SEQ ID NO 33
<211> LENGTH: 40
<212> TYPE: DNA
<213> ORGANISM: Artificial Sequence
<220> FEATURE:
<223> OTHER INFORMATION: Synthetic construct

<400> SEQUENCE: 33
gagatagttt gtgtagagag tagtaagtag tttttttttt 40

<210> SEQ ID NO 34
<211> LENGTH: 40
<212> TYPE: DNA
<213> ORGANISM: Artificial Sequence
<220> FEATURE:
<223> OTHER INFORMATION: Synthetic construct

<400> SEQUENCE: 34
gtgtgaatga tgattagatt ggaaagtgag tttttttttt 40

<210> SEQ ID NO 35
<211> LENGTH: 81
<212> TYPE: DNA
<213> ORGANISM: Artificial Sequence
<220> FEATURE:
<223> OTHER INFORMATION: Synthetic construct

<400> SEQUENCE: 35
gttgttagat gtaatgatag ttgttgttga tttttgtatt tgtttgtatt tgcaagttaa 60
aagatctttt gaagtttttt t 81

<210> SEQ ID NO 36
<211> LENGTH: 81
<212> TYPE: DNA
<213> ORGANISM: Artificial Sequence
<220> FEATURE:
<223> OTHER INFORMATION: Synthetic construct

<400> SEQUENCE: 36
agattgatgt ataagtaata gtgtggtgta tttttgtatt tgtttgtatt tgcaagttaa 60
aagatctttt gaagtttttt t 81

<210> SEQ ID NO 37
<211> LENGTH: 81
<212> TYPE: DNA
<213> ORGANISM: Artificial Sequence
<220> FEATURE:
<223> OTHER INFORMATION: Synthetic construct

<400> SEQUENCE: 37
ttttttactt ttcaaccacc actcaaccat attcaaagct tacgatgccg actcattcgc 60
cataaactct caataaccaa t 81

<210> SEQ ID NO 38
<211> LENGTH: 24
<212> TYPE: DNA
<213> ORGANISM: Artificial Sequence
<220> FEATURE:
<223> OTHER INFORMATION: Synthetic construct

<400> SEQUENCE: 38 tttttactt ttcaaccacc actc 24

<210> SEQ ID NO 39
<211> LENGTH: 24
<212> TYPE: DNA
<213> ORGANISM: Artificial Sequence
<220> FEATURE:
<223> OTHER INFORMATION: Synthetic construct

<400> SEQUENCE: 39
attggttatt gagagtttat ggcg 24

<210> SEQ ID NO 40
<211> LENGTH: 25
<212> TYPE: DNA
<213> ORGANISM: Artificial Sequence
<220> FEATURE:
<223> OTHER INFORMATION: Synthetic construct

<400> SEQUENCE: 40
aacttcaaaa gatcttttaa cttgc 25

<210> SEQ ID NO 41
<211> LENGTH: 42
<212> TYPE: DNA
<213> ORGANISM: Artificial Sequence
<220> FEATURE:
<223> OTHER INFORMATION: Synthetic construct

<400> SEQUENCE: 41
aaaaacaaaa acaaaaaaac ttcaaaagat cttttaactt gc 42

<210> SEQ ID NO 42
<211> LENGTH: 38
<212> TYPE: DNA
<213> ORGANISM: Artificial Sequence
<220> FEATURE:
<223> OTHER INFORMATION: Synthetic construct

<400> SEQUENCE: 42
taaaacaaaa tcgttgttag atgtaatgat agttgttg 38

<210> SEQ ID NO 43
<211> LENGTH: 38
<212> TYPE: DNA
<213> ORGANISM: Artificial Sequence
<220> FEATURE:
<223> OTHER INFORMATION: Synthetic construct

<400> SEQUENCE: 43
taaaacaaaa tcagattgat gtataagtaa tagtgtgg 38

<210> SEQ ID NO 44
<211> LENGTH: 57
<212> TYPE: DNA
<213> ORGANISM: Artificial Sequence
<220> FEATURE:
<223> OTHER INFORMATION: Synthetic construct

<400> SEQUENCE: 44
aacttcaaaa gatcttttaa cttgcaaata ctttttccac ctaccaccac caaccac 57